(12) United States Patent
Ueno et al.

(10) Patent No.: US 12,421,627 B2
(45) Date of Patent: Sep. 23, 2025

(54) PEPTIDE-NUCLEIC ACID COMPLEX

(71) Applicant: KAWASAKI INSTITUTE OF INDUSTRIAL PROMOTION, Kanagawa (JP)

(72) Inventors: Shingo Ueno, Kawasaki (JP); Takanori Ichiki, Kawasaki (JP)

(73) Assignee: KAWASAKI INSTITUTE OF INDUSTRIAL PROMOTION, Kanagawa (JP)

( * ) Notice: Subject to any disclaimer, the term of this patent is extended or adjusted under 35 U.S.C. 154(b) by 1176 days.

(21) Appl. No.: 17/291,964

(22) PCT Filed: Nov. 7, 2019

(86) PCT No.: PCT/JP2019/043640
§ 371 (c)(1),
(2) Date: May 6, 2021

(87) PCT Pub. No.: WO2020/095985
PCT Pub. Date: May 14, 2020

(65) Prior Publication Data
US 2022/0010032 A1    Jan. 13, 2022

(30) Foreign Application Priority Data
Nov. 7, 2018  (JP) .................................. 2018-209874

(51) Int. Cl.
*C40B 40/08*    (2006.01)
(52) U.S. Cl.
CPC .................... *C40B 40/08* (2013.01)
(58) Field of Classification Search
None
See application file for complete search history.

(56) References Cited

U.S. PATENT DOCUMENTS

| 9,631,218 B2 | 4/2017 | Tsourkas et al. |
| 2006/0003347 A1 | 1/2006 | Griffiths et al. |

(Continued)

FOREIGN PATENT DOCUMENTS

| CA | 3056756 A1 | 9/2018 |
| JP | 2006211984 A | 8/2006 |

(Continued)

OTHER PUBLICATIONS

International Search Report issued in PCT Patent Application No. PCT/JP2019/043640 mailed Feb. 4, 2020.

(Continued)

*Primary Examiner* — Christian C Boesen
(74) *Attorney, Agent, or Firm* — MARSHALL, GERSTEIN & BORUN LLP

(57) ABSTRACT

There is provided a method for producing a peptide-nucleic acid complex containing a peptide and a nucleic acid encoding the peptide. The method for producing a peptide-nucleic acid complex includes a step of preparing a nucleic acid to which a transpeptidase N-terminal substrate motif has been added, the nucleic acid containing a first coding sequence encoding a peptide, a second coding sequence encoding a transpeptidase, and a third coding sequence encoding a transpeptidase recognition motif; a step of synthesizing a chimeric protein containing a domain of the peptide, a domain of the transpeptidase, and the transpeptidase recognition motif, from the nucleic acid to which the transpeptidase N-terminal substrate motif has been added, using a cell-free protein synthesis system; and a step of forming the peptide-nucleic acid complex by means of the transpeptidase domain.

11 Claims, 15 Drawing Sheets

Specification includes a Sequence Listing.

(56) References Cited

U.S. PATENT DOCUMENTS

| | | | |
|---|---|---|---|
| 2016/0137720 A1 | 5/2016 | Song et al. | |
| 2016/0279257 A1* | 9/2016 | Koussa | A61K 47/65 |
| 2016/0298109 A1 | 10/2016 | Ogg et al. | |
| 2016/0341727 A1 | 11/2016 | Ogg et al. | |

FOREIGN PATENT DOCUMENTS

| | | |
|---|---|---|
| JP | 2006-521922 A | 9/2006 |
| JP | 4318721 B2 | 8/2009 |
| JP | 2009178067 A | 8/2009 |
| JP | 2016-519118 A | 6/2016 |
| JP | 2016-523978 A | 8/2016 |
| JP | 2018-15013 A | 2/2018 |
| WO | WO-2004/087308 A1 | 10/2004 |
| WO | WO-2004/087803 A1 | 10/2004 |
| WO | WO-2005/001086 A1 | 1/2005 |
| WO | WO-2005/051976 A2 | 6/2005 |
| WO | WO-2010/011944 A2 | 1/2010 |
| WO | WO-2015/006626 A1 | 1/2015 |
| WO | WO-2018/168999 A1 | 9/2018 |

OTHER PUBLICATIONS

Nemoto et al., "In vitro virus: Bonding of mRNA bearing puromycin at the 3'-terminal end to the C-terminal end of its encoded protein on the ribosome in vitro," *FEBS Letters 414*, pp. 405-408 (1997).

Yamaguchi, J. et al., "cDNA display: a novel screening method for functional disulfide-rich peptides by solid-phase synthesis and stabilization of mRNA-protein fusions," *Nucleic Acids Research*, vol. 37, No. 16 (2009).

Diamante, L. et al., "In vitro affinity screening of protein and peptide binders by megavalent bead surface display," *Protein Engineering, Design & Selection*, vol. 26, No. 10, pp. 713-724 (2013).

Mankowska, S. et al., "A Shorter Route to Antibody Binders via Quantitative in vitro Bead-Display Screening and Consensus Analysis," *Scientific Reports* (2016).

Pritz, S. et al., "Synthesis of Biologically Active Peptide Nucleic Acid-Peptide Conjugates by Sortase-Mediated Ligation," *J. Org. Chem.*, pp. 3909-3912 (2007).

Gan, R. et al., "Microbeads Display of Proteins Using Emulsion PCR and Cell-Free Protein Synthesis," *Biotechnol. Prog.*, pp. 1107-1114 (2008).

Gan, R. et al., "Directed evolution of angiotensin II-inhibiting peptides using a microbead display," *Journal of Science and Bioengineering*, vol. 109, No. 4 pp. 411-417 (2010).

Sepp, A. et al., "Microbead display by in vitro compartmentalization: selection for binding using flow cytometry," *FEBS Letters*, pp. 455-458 (2002).

Griffiths, A. et al., "Directed evolution of an extremely fast phosphotriesterase by in vitro compartmentalization," *The EMBO Journal*, vol. 22, No. 1, pp. 24-35 (2003).

Zhu, B. et al., "Ultra-High-Throughput Screening of an In Vitro-Synthesized Horseradish Peroxidase Displayed on Microbeads Using Cell Sorter," *PLOS one* (2015).

Kojima, T. et al., "Immobilization of proteins onto microbeads using a DNA binding tag for enzymatic assays," *Journal of Bioscience and Bioengineering*, vol. 121, No. 2, pp. 147-153 (2016).

Huang, L. et al., "Linking genotype to phenotype on beads: high throughput selection of peptides with biological function," *Scientific Reports* (2013).

Lee K., et al., "On-bead expression of recombinant proteins in an agarose gel matrix coated on a glass slide," The Royal Society of Chemistry, *Lab Chip*, vol. 12, No. 9 (2012).

Koussa, M., et al., "Protocol for sortase-mediated constructions of DNA-protein hybrids and functional nanostructures," *Methods*, pp. 134-141 (2014).

Gogoi, K., et al., "A versatile method for the preparation of conjugates of peptides with DNA/PNA/analog by employing chemoselective click reaction in water," *Nucleic Acids Research*, vol. 35, No. 21 (2007).

Brown, S. et al., "Conjugation of an oligonucleotide to Tat, a cell-penetrating peptide, via click chemistry," *Tetrahedron Letters*, pp. 5032-5034 (2010).

Warden-Rothman, R., et al., "Sortase-Tag Expressed Protein Ligation: Combining Protein Purification and Site-Specific Bioconjugation into a Single Step," *Analytical Chemistry*, pp. 11090-11097 (2013).

Piotukh, K. et al., "Directed Evolution of Sortase A Mutants with Altered Substrate Selectivity Profiles," *Journal of the American Chemical Society*, pp. 17536-17539 (2011).

Mao, H. "A self-cleavable sortase fusion for one-step purification of free recombinant proteins," *Protein Expression and Purification*, pp. 253-263 (2004).

* cited by examiner

PEPTIDE-NUCLEIC ACID COMPLEX

TECHNICAL FIELD

The present invention relates to a peptide-nucleic acid complex. Further, the present invention relates to an immobilized carrier on which a peptide-nucleic acid complex has been immobilized and a peptide array having a reaction chamber containing the immobilized carrier. In addition, the present invention also relates to a method for producing a peptide-nucleic acid complex, a nucleic acid that can be used in the producing method, and a kit.

Priority is claimed on Japanese Patent Application No. 2018-209874, filed on Nov. 7, 2018, the content of which is incorporated herein by reference.

BACKGROUND ART

A novel functional peptide is expected to contribute to various biological applications in fields such as pharmaceutical drugs, detergents, food processing, reagents for research and development, and clinical analysis, and further in the fields of bioenergy and biosensors.

The mainstream methods for acquiring a novel functional peptide have been peptide engineering methods in which designing is carried out by human knowledge based on the structural information of the peptide. However, it is necessary to carry out screening more efficiently than in the conventional method in order to acquire more useful peptides, and thus evolutionary molecular engineering methods in which random modification of peptides in molecular structure and selection of the peptides is performed repeatedly are expected.

The cDNA display method, which is one of the evolutionary molecular engineering methods, is a genotype-phenotype matching method and a nucleic acid linker links between a peptide (a phenotype), an mRNA encoding the peptide, and a reverse-transcribed cDNA (a genotype). Since a structure of an mRNA/cDNA-peptide linked body is very stable, it has become possible to carry out screening in various environments by using the corresponding nucleic acid linker.

As a method for linking a peptide and a polynucleotide encoding the peptide, a method in which a puromycin linker is used is known (see Patent Document 1). Puromycin is a peptide synthesis inhibitor having a structure similar to the 3' terminal of an aminoacyl-tRNA and covalently bonds specifically to the C-terminal of a peptide elongating on the ribosome under predetermined conditions.

A method of constructing a library of mRNA/cDNA-linker-peptide complexes using a puromycin linker and carrying out a screening for a useful protein has the following series of steps.

First, a linker having puromycin is linked to an mRNA, a peptide is synthesized from mRNA using a cell-free translation system, and a complex (an mRNA-linker-peptide complex) in which the synthesized peptide and the mRNA encoding the peptide are bonded via puromycin is generated (see Non Patent Document 1).

Next, a library of these mRNA-linker-peptide complexes are produced, and the produced mRNA-linker-peptide complexes are subsequently reverse-transcribed by a reverse transcriptase to synthesize cDNA, whereby a library of mRNA/cDNA-linker-peptide complexes are produced.

Next, using this library of mRNA/cDNA-linker-peptide complexes, a peptide having a desired function is selected, and the base sequence of the cDNA in the selected mRNA/cDNA-linker-peptide complex is analyzed to identify the peptide (see Non Patent Document 2).

A peptide array in which the above library of mRNA/cDNA-linker-peptide complexes is immobilized on a substrate is important as a tool for acquiring a functional protein or a functional peptide in a short period of time by comprehensive analysis.

In addition, as a method for producing a cDNA-peptide complex, a method in which a SNAP tag fusion peptide is synthesized in a cell-free manner from a benzylguanine-modified DNA, and the cDNA and the peptide are bonded via a covalent bonding between benzylguanine and the SNAP tag is also known (Non Patent Documents 3 and 4).

However, the method using a puromycin linker has a problem in that the preparation of the puromycin linker is complicated.

In addition, in the method using a benzylguanine-modified DNA, DNA is linked to a protein via a SNAP tag of 20 kDa, and thus the three-dimensional structure and the function of the presented protein may be impaired.

CITATION LIST

Patent Document

[Patent Document 1]
Japanese Patent No. 4318721

Non Patent Documents

[Non Patent Document 1]
Nemoto N et al., In vitro virus: bonding of mRNA bearing puromycin at the 3'-terminal end to the C-terminal end of its encoded protein on the ribosome in vitro. FEBS Lett. 1997 Sep. 8; 414 (2): 405 to 408.
[Non Patent Document 2]
Yamaguchi J et al., cDNA display: a novel screening method for functional disulfide-rich peptides by solid-phase synthesis and stabilization of mRNA-protein fusions. Nucleic Acids Res. 2009 September; 37 (16): e108.
[Non Patent Document 3]
Diamante L et al., In vitro affinity screening of protein and peptide binders by megavalent bead surface display. Protein Eng Des Sel. 2013 October; 26 (10): 713 to 724.
[Non Patent Document 4]
Mankowska S A et al., A Shorter Route to Antibody Binders via Quantitative in vitro Bead-Display Screening and Consensus Analysis. Sci Rep. 2016 Nov. 7; 6: 36391.

SUMMARY OF INVENTION

The present invention has been made in consideration of the above circumstances, and an object of the present invention is to provide a novel method for producing a peptide-nucleic acid complex, a peptide-nucleic acid complex produced by the producing method, and a nucleic acid that can be used in the producing method, and a kit.

The present invention includes the following aspects.

[1] A method for producing a peptide-nucleic acid complex containing a peptide and a nucleic acid encoding the peptide, the method including (A1) a step of preparing a nucleic acid to which a transpeptidase N-terminal substrate motif has been added, the nucleic acid containing a first coding sequence encoding the peptide, a second coding sequence encoding a transpeptidase, and a third coding sequence encoding a transpeptidase recognition motif; (B1) a step of synthesizing a chimeric protein containing a domain of the peptide, a domain of the transpeptidase, and the transpeptidase recognition motif, from the nucleic acid to which the transpeptidase N-terminal substrate motif has been added, using a cell-free protein synthesis system; and (C1) a step of forming the peptide-nucleic acid complex through a transpeptidation reaction by the transpeptidase domain.

[2] The method for producing a peptide-nucleic acid complex according to [1], in which the first coding sequence, the third coding sequence, and the second coding sequence are arranged in order from a 5' side to a 3' side in the nucleic acid.

[3] The method for producing a peptide-nucleic acid complex according to [1], in which the second coding sequence, the first coding sequence, and the third coding sequence are arranged in order from a 5' side to a 3' side in the nucleic acid.

[4] The method for producing a peptide-nucleic acid complex according to [1], in which the first coding sequence, the second coding sequence, and the third coding sequence are arranged in order from a 5' side to a 3' side in the nucleic acid.

[5] The method for producing a peptide-nucleic acid complex according to any one of [1] to [4], in which the nucleic acid to which the transpeptidase N-terminal substrate motif has been added is immobilized on a solid phase carrier.

[6] A method for producing a peptide-nucleic acid complex containing a peptide and a nucleic acid encoding the peptide, the method including (A2) a step of preparing a nucleic acid to which a transpeptidase recognition motif has been added, the nucleic acid containing a first coding sequence encoding a peptide, a second coding sequence encoding a transpeptidase, and a third coding sequence encoding a transpeptidase N-terminal substrate motif; (B2) a step of synthesizing a chimeric protein containing a domain of the peptide, a domain of the transpeptidase, and the transpeptidase N-terminal substrate motif, from the nucleic acid to which the transpeptidase recognition motif has been added, using a cell-free protein synthesis system; and (C2) a step of forming the peptide-nucleic acid complex through a transpeptidation reaction by the transpeptidase domain.

[7] The method for producing a peptide-nucleic acid complex according to [6], in which the third coding sequence, the first coding sequence, and the second coding sequence are arranged in order from a 5' side to a 3' side in the nucleic acid.

[8] The method for producing a peptide-nucleic acid complex according to [6], in which the third coding sequence, the second coding sequence, and the first coding sequence are arranged in order from a 5' side to a 3' side in the nucleic acid.

[9] The method for producing a peptide-nucleic acid complex according to any one of [6] to [8], in which the nucleic acid further contains a fourth coding sequence encoding a protease recognition motif, the fourth coding sequence being adjacent to a 5' terminal of the third coding sequence and the protease having an activity of cleaving a bond between the protease recognition motif and a transpeptidase N-terminal substrate motif, the method further including (D2) a step of cleaving the bond between the protease recognition motif and the transpeptidase N-terminal substrate motif using the protease, after the step (B2) and before the step (C2).

[10] The method for producing a peptide-nucleic acid complex according to any one of [6] to [9], in which the nucleic acid to which the transpeptidase recognition motif has been added is immobilized on a solid phase carrier.

[11] A peptide-nucleic acid complex containing (a) a peptide; (b) a nucleic acid containing a coding sequence of the peptide; and (c) a sequence generated by bonding a transpeptidase recognition motif and a transpeptidase N-terminal substrate motif through a transpeptidation reaction by the transpeptidase, the sequence of (c) being located between the peptide of (a) and the nucleic acid of (b).

[12] The nucleic acid-peptide complex according to [11], in which the nucleic acid of (b) contains a first coding sequence encoding the peptide of (a), a second coding sequence encoding the transpeptidase, and a third coding sequence encoding the transpeptidase recognition motif or the transpeptidase N-terminal substrate motif.

[13] The nucleic acid-peptide complex according to [12], in which the third coding sequence is a sequence encoding the transpeptidase recognition motif, and the first coding sequence, the third coding sequence, and the second coding sequence are arranged in order from a 5' side to a 3' side in the nucleic acid of (b).

[14] The nucleic acid-peptide complex according to [12], in which the third coding sequence is a sequence encoding the transpeptidase recognition motif, and the second coding sequence, the first coding sequence, and the third coding sequence are arranged in order from a 5' side to a 3' side in the nucleic acid of (b).

[15] The nucleic acid-peptide complex according to [12], in which the third coding sequence is a sequence encoding the transpeptidase recognition motif, and the first coding sequence, the second coding sequence, and the third coding sequence are arranged in order from a 5' side to a 3' side in the nucleic acid of (b).

[16] The nucleic acid-peptide complex according to [12], in which the third coding sequence is a sequence encoding the transpeptidase N-terminal substrate motif, and the third coding sequence, the first coding sequence, and the second coding sequence are arranged in order from a 5' side to a 3' side in the nucleic acid of (b).

[17] The nucleic acid-peptide complex according to [12], in which the third coding sequence is a sequence encoding the transpeptidase N-terminal substrate motif, and the third coding sequence, the second coding sequence, and the first coding sequence are arranged in order from a 5' side to a 3' side in the nucleic acid of (b).

[18] The nucleic acid-peptide complex according to [16] or [17], in which the nucleic acid of (b) further contains a fourth coding sequence encoding a protease recognition motif, the fourth coding sequence being adjacent to a 5' terminal of the third coding sequence, and the protease has an activity of cleaving a bond between the protease recognition motif and the transpeptidase N-terminal substrate motif.

[19] A solid phase carrier on which the peptide-nucleic acid complex according to any one of [11] to [18] has been immobilized.

[20] A peptide array containing a reaction chamber containing the solid phase carrier according to [19].

[21] The peptide array according to [20], in which each reaction chamber contains one kind of the peptide-nucleic acid complex.

[22] A nucleic acid to which a transpeptidase N-terminal substrate motif has been added, the nucleic acid containing a first coding sequence encoding a peptide; a second coding sequence encoding the transpeptidase; and a third coding sequence encoding a transpeptidase recognition motif.

[23] The nucleic acid according to [22], in which the first coding sequence, the third coding sequence, and the second coding sequence are arranged in order from a 5' side to a 3' side.

[24] The nucleic acid according to [22], in which the second coding sequence, the first coding sequence, and the third coding sequence are arranged in order from a 5' side to a 3' side.

[25] The nucleic acid according to [22], in which the first coding sequence, the second coding sequence, and the third coding sequence are arranged in order from a 5' side to a 3' side in the nucleic acid.

[26] A nucleic acid to which a transpeptidase recognition motif has been added, the nucleic acid containing a first coding sequence encoding a peptide; a second coding sequence encoding the transpeptidase; and a third coding sequence encoding a transpeptidase N-terminal substrate motif.

[27] The nucleic acid according to [26], in which the third coding sequence, the first coding sequence, and the second coding sequence are arranged in order from a 5' side to a 3' side.

[28] The nucleic acid according to [26], in which the third coding sequence, the second coding sequence, and the first coding sequence are arranged in order from a 5' side to a 3' side.

[29] The nucleic according to any one of [26] or [28], in which the nucleic acid further contains a fourth coding sequence encoding a protease recognition motif, the fourth coding sequence being adjacent to a 5' terminal of the third coding sequence, and the protease has an activity of cleaving a bond between the protease recognition motif and the transpeptidase N-terminal substrate motif.

[30] A solid phase carrier on which the nucleic acid according to any one of [22] to [29] has been immobilized.

[31] A kit for preparing a peptide-nucleic acid complex, the kit containing the following (a) to (d);
   (a) a nucleic acid which contains a first coding sequence encoding any peptide or a cloning site into which a nucleic acid fragment containing the first coding sequence can be inserted, a second coding sequence encoding a transpeptidase, and a third coding sequence encoding a transpeptidase recognition motif,
   (b) a primer set with which a region in the nucleic acid of (a), the region including the first coding sequence or the cloning site, the second coding sequence, and the third coding sequence, can be amplified and in which the transpeptidase N-terminal substrate motif is added to any one of a forward primer or a reverse primer,
   (c) a nucleic acid amplification reagent, and
   (d) a cell-free protein synthesis reaction solution.

[32] The kit for preparing a peptide-nucleic acid complex according to [31], in which the first coding sequence or the cloning site, the third coding sequence, and the second coding sequence are arranged in order from a 5' side to a 3' side in the nucleic acid of (a).

[33] The kit for preparing a peptide-nucleic acid complex according to [31], in which the second coding sequence, the first coding sequence or the cloning site, and the third coding sequence are arranged in order from a 5' side to a 3' side in the nucleic acid of (a).

[34] The kit for preparing a peptide-nucleic acid complex according to [31], in which the first coding sequence or the cloning site, the second coding sequence, and the third coding sequence are arranged in order from a 5' side to a 3' side in the nucleic acid of (a).

[35] A kit for preparing a peptide-nucleic acid complex, the kit containing the following (a) to (d);
   (a) a nucleic acid which contains a first coding sequence encoding any peptide or a cloning site into which a nucleic acid fragment containing the first coding sequence can be inserted, a second coding sequence encoding the transpeptidase, and a third coding sequence encoding a transpeptidase N-terminal substrate motif,
   (b) a primer set with which a region in the nucleic acid of (a), the region including the first coding sequence or the cloning site, the second coding sequence, and the third coding sequence, can be amplified and in which a transpeptidase recognition motif is added to any one of a forward primer or a reverse primer,
   (c) a nucleic acid amplification reagent, and
   (d) a cell-free protein synthesis reaction solution.

[36] The kit for preparing a peptide-nucleic acid complex according to [35], in which the third coding sequence, the first coding sequence or the cloning site, and the second coding sequence are arranged in order from a 5' side to a 3' side in the nucleic acid of (a).

[37] The kit for preparing a peptide-nucleic acid complex according to [35], in which the third coding sequence, the second coding sequence, and the first coding sequence or the cloning site are arranged in order from a 5' side to a 3' side in the nucleic acid of (a).

[38] The kit for preparing a peptide-nucleic acid complex according to any one of [35] to [37], in which the nucleic acid of (a) further contains a fourth coding sequence encoding a protease recognition motif, the fourth coding sequence being adjacent to a 5' terminal of the third coding sequence, and the protease has an activity of cleaving a bond between the protease recognition motif and the transpeptidase N-terminal substrate motif.

According to the present invention, a novel producing method for producing a peptide-nucleic acid complex, a peptide-nucleic acid complex produced by the producing method, a nucleic acid that can be used for the producing method, and a kit are provided.

DETAILED DESCRIPTION OF EMBODIMENTS

Figure 1A:
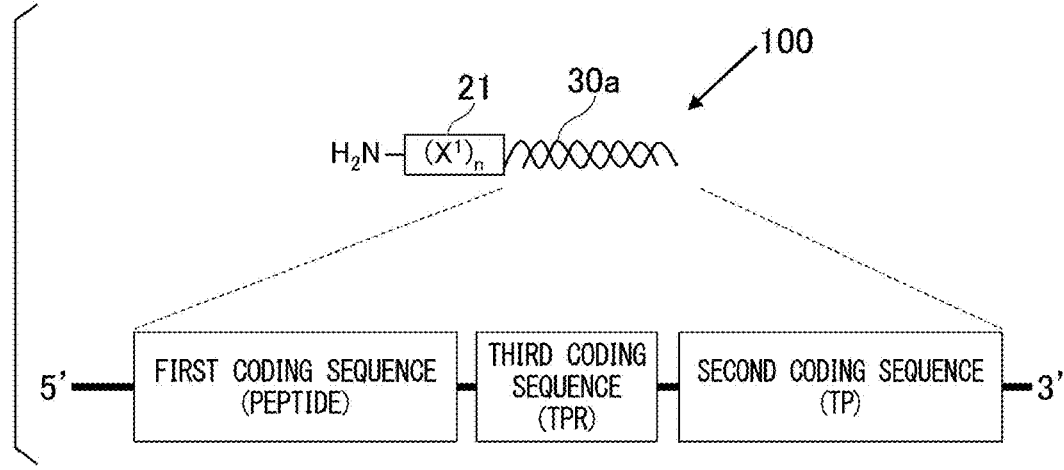
FIG. 1A is a schematic diagram showing an example of a step (A1) in a method for producing a peptide-nucleic acid complex according to the first embodiment of the present invention. An example of a nucleic acid to which a transpeptidase N-terminal substrate motif has been added is shown.

In the present specification, the terms "polynucleotide" and "nucleic acid" are used interchangeably and mean a nucleotide polymer in which nucleotides are bonded by a phosphodiester bond. The "polynucleotide" or "nucleic acid" may be DNA or RNA, or may be composed of a combination of DNA and RNA. In addition, the "polynucleotide" and "nucleic acid" may be a polymer of natural nucleotides, may be a polymer of natural nucleotides and unnatural nucleotides (an analog of a natural nucleotide or a nucleotide (for example, a phosphorothioate skeleton) in which at least one moiety of a base moiety, a sugar moiety, and a phosphate moiety of a natural nucleotide is modified), or may be a polymer of an unnatural nucleotide.

In the present specification, a base sequence of the "polynucleotide" or "nucleic acid" is described with a generally accepted one-letter code unless otherwise specified. In the present specification, a base sequence of the "polynucleotide" or "nucleic acid" is described from the 5' side to the 3' side unless otherwise specified.

In the present specification, nucleotide residues constituting the "polynucleotide" or "nucleic acid" may be simply described as adenine, thymine, cytosine, guanine, uracil, and the like, or may be described with one-letter codes thereof.

In the present specification, the term "gene" means a polynucleotide containing at least one open reading frame encoding a specific protein. The gene can contain both an exon and an intron.

In the present specification, the terms "polypeptide", "peptide", and "protein" are used interchangeably and mean a polymer of amino acids bonded by an amide bond. The "polypeptide", "peptide", or "protein" may be a polymer of natural amino acids, may be a polymer of natural amino acids and unnatural amino acids (a chemical analog, a modified derivative, or the like of a natural amino acid), or may be a polymer of unnatural amino acids.

In the present specification, an amino acid sequence of the "polypeptide", "peptide", or "protein" is described with a generally accepted one-letter code or three-letter code unless otherwise specified. In the present specification, the amino acid sequence of the "polypeptide", "peptide", or "protein" is described from the N-terminal side to the C-terminal side unless otherwise specified.

In the present specification, in a case where a substitution mutation in an amino acid sequence is indicated, the substitution mutation may be indicated by the one-letter notation of the original amino acid, followed by a 1 to 4 digit number indicating the position number, and then the one-letter notation of the amino acid with which the original amino acid is substituted. For example, in a case where there is a mutation in which proline (P) is substituted with serine (S) at the position of the amino acid number 94, this mutation is indicated as "P94S", the meaning of which is the same as the "substitution of Pro with Ser at the position of the amino acid number 94".

In the present specification, the term "transpeptidase" means an enzyme that can catalyze the cleavage of a peptide bond and form a novel peptide bond, directly or via a plurality of reaction intermediates. The transpeptidase has catalytic activity of recognizing a transpeptidase recognition motif having a specific amino acid sequence, cleaving a peptide bond in the transpeptidase recognition motif, and being capable of forming a novel peptide bond between the C-terminal of the cleaved transpeptidase recognition motif and the N-terminal of the transpeptidase N-terminal substrate motif having a specific amino acid sequence. Preferred examples of the transpeptidase include sortase and buterase.

In the present specification, the term "sortase" means a group of enzymes of a group of prokaryotes, which have transpeptidase activity, and variants thereof. The sortase has catalytic activity of recognizing a sortase recognition motif having a specific amino acid sequence, cleaving a peptide bond in the sortase recognition motif, and being capable of forming a novel peptide bond between the C-terminal of the cleaved sortase recognition motif and the N-terminal of a sortase N-terminal substrate motif having a specific amino acid sequence.

Enzymes identified as the "sortase" have been isolated from various Gram-positive bacteria. In nature, these enzymes catalyze the cell wall sorting reaction. In the cell wall sorting reaction, a surface protein having a sortase recognition motif is cleaved and the C-terminal of the cleaved protein is covalently bonded to a pentaglycine crosslink of peptidoglycan. Examples of the Gram-positive bacteria having a sortase include the genus *Actinomyces*, the genus *Bacillus*, the genus *Bifidobacterium*, the genus *Cellulomonas*, the genus *Clostridium*, the genus *Corynebacterium*, the genus *Micrococcus*, the genus *Mycobacterium*, the genus *Nocardia*, the genus *Staphylococcus*, the genus *Streptococcus*, and the genus *Streptomyces*. The sortases are classified into four classes of A, B, C, and D, based on the sequence alignment and phylogenetic tree analysis of 61 sortases derived from Gram-positive bacterial genomes (Dramsi S, Trieu-Cuot P, Bierne H, Sorting sortases: a nomenclature proposal for the various sortases of Gram-positive bacteria. Res Microbiol. 156 (3): 289 to 297, 2005). These classes of sortases also correspond to the following sub-families classified by Comfort and Clubb; Class A (sub-family 1), Class B (sub-family 2), Class C (sub-family 3), and Class D (sub-families 4 and 5) (Comfort D, Clubb R T. A comparative genome analysis identifies distinct sorting pathways in Gram-positive bacteria. Infect Immun. 72 (5): 2710 to 2722, 2004). The reference documents described above disclose a large number of sortases and recognition motifs.

In the present specification, the term "buterase" means an enzyme isolated from *Clitoria ternatea* (Nguyen G K et al., Nat Protoc. 2016 October; 11 (10): 1977 to 1988, and Published Japanese Translation No. 2017-515468 of the PCT International Publication), which has transpeptidase activity, a homolog thereof (including an ortholog and a paralog), or a variant thereof.

In the present specification, the term "transpeptidase recognition motif" means a region having a specific amino acid sequence that is recognized by a transpeptidase. The transpeptidase recognition motif is recognized by a transpeptidase and a peptide bond in the motif is cleaved. The transpeptidase recognition motif may differ depending on the kind of transpeptidase. In the present specification, a transpeptidase recognition motif for a sortase is also described as a sortase recognition motif. In the present specification, a transpeptidase recognition motif for a buterase is also described as a buterase recognition motif.

In the present specification, the term "transpeptidase N-terminal substrate motif" means an N-terminal region located at the N-terminal of a peptide and having a specific amino acid sequence that is subjected to transpeptidation reaction by a transpeptidase. A peptide having the transpeptidase N-terminal substrate motif is bonded to the C-terminal of the transpeptidase recognition motif after being cleaved by a transpeptidase, by the catalytic action of transpeptidase.

In the present specification, the phrase "adjacent to the 5' terminal" or "adjacent to the 3' terminal" means a state where a base sequence of interest is linked to the 5' terminal or 3' terminal of a base sequence without the interposition of other nucleotide residues. That is, in the case where "a sequence B is adjacent to the 5' terminal of a sequence A", the 5' terminal of the sequence A and the 3' terminal of the sequence B are directly linked with no other sequence intervening. Similarly, in the present specification, the phrase "adjacent to the N-terminal" or "adjacent to the C-terminal" means a state where an amino acid sequence of interest is linked to the N-terminal or C-terminal of an amino acid sequence without the interposition of other amino acid residues.

In the present specification, the phrase "located on the 5' side" or "located on the 3' side" means a state where a base sequence of interest is located on the 5' side or 3' side of a base sequence with the interposition of other nucleotide residues or without the interposition of other nucleotide residues. That is, in the case where "a sequence B is located on the 5' side of a sequence A", the sequence B and the sequence A are arranged in order from the 5' side to the 3' side, and other nucleotide residues may be or may not be interposed between the sequence A and the sequence B. In a case where other nucleotide residues are interposed between the sequence A and the sequence B, the number and kinds of the nucleotide residues interposed are not limited, and for example, a spacer coding sequence, a protein coding sequence, another ORF, or the like may be interposed. Similarly, in the present specification, the phrase "located on the N-terminal side" or "located on the C-terminal side" means a state where an amino acid sequence of interest is located on the N-terminal side or C-terminal side of an amino acid sequence with the interposition of other amino acid residues or without the interposition of other amino acid residues.

In the present specification, the phrase "functionally linked" that is used for a polynucleotide or a nucleic acid means a state where a first base sequence is located sufficiently close to a second base sequence and thus the first base sequence can have an influence on a region which is under the regulation of the second base sequence or the second base sequence. For example, a description that a polynucleotide or nucleic acid is functionally linked to the promoter means that the polynucleotide or the nucleic acid is linked to be expressed under the regulation of the promoter.

In the present specification, the phrase "a protein can be expressed" that is used for a polypeptide or a nucleic acid refers to a state where the protein can be synthesized from the polynucleotide or the nucleic acid in a case where a cell-free protein synthesis system is applied to the polynucleotide or the nucleic acid.

In the present specification, the term "silent mutation" refers to a genetic mutation in which an amino acid sequence of an encoded protein does not change.

In the present specification, the sequence identity (or homology) between amino acid sequences is determined by juxtaposing two amino acid sequences so that the corresponding amino acids thereof match as much as possible while inserting a gap in the portion corresponding to an insertion and a deletion and obtaining a proportion of the matched amino acids to the total amino acid sequence from which gaps of the obtained alignment have been excluded. The sequence identity between amino acid sequences can be determined by using various types of homology search software known in the art. For example, the value of sequence identity between amino acid sequences can be obtained by calculation based on the alignment obtained by the known homology search software BLASTP.

In the present specification, the term "chimeric protein" means a protein that includes two or more peptides of different origins.

In the present specification, the term "primer set" means a set of primers that is used to amplify a target nucleic acid in a nucleic acid amplification reaction. In a case where the nucleic acid amplification reaction is carried out by PCR, the primer set includes a forward primer and a reverse primer. "Forward primer" means a primer that anneals to an antisense strand of a template nucleic acid, and "reverse primer" means a primer that anneals to a sense strand of the template nucleic acid.

Hereinafter, embodiments of the present invention will be described in detail with reference to the drawings as necessary. In the drawings, the same or corresponding parts are designated by the same or corresponding reference numerals, and the description thereof will not be duplicated. Dimensional ratios in the figures may be exaggerated for description and thus may not necessarily match actual dimensional ratios.

<Method for Producing Peptide-Nucleic Acid Complex>

<<First Aspect>>

In one embodiment, the present invention provides a method for producing a peptide-nucleic acid complex containing a peptide and a nucleic acid encoding the peptide. The producing method includes (A1) a step of preparing a nucleic acid to which a transpeptidase N-terminal substrate motif has been added, the nucleic acid containing a first coding sequence encoding the peptide, a second coding sequence encoding a transpeptidase, and a third coding sequence encoding a transpeptidase recognition motif; (B1) a step of synthesizing a chimeric protein containing a domain of the peptide, a domain of the transpeptidase, and the transpeptidase recognition motif, from the nucleic acid to which the transpeptidase N-terminal substrate motif has been added, using a cell-free protein synthesis system; and (C1) a step of forming the peptide-nucleic acid complex through a transpeptidation reaction by the transpeptidase domain of the chimeric protein.

First Embodiment

An outline of the first embodiment of the producing method according to the present aspect will be described with reference to FIGS. 1A to 1C.

First, a nucleic acid 100 (hereinafter, may be referred to as an "NS-added nucleic acid 100") to which a transpeptidase N-terminal substrate motif 21 has been added is prepared (FIG. 1A; step (A1)). The NS-added nucleic acid 100 contains a first coding sequence encoding any peptide; a second coding sequence encoding a transpeptidase; and a third coding sequence encoding a transpeptidase recognition motif. In the NS-added nucleic acid 100, the first coding sequence, the third coding sequence, and the second coding sequence are arranged in order from the 5' side to the 3' side. Further, in the NS-added nucleic acid 100, these coding sequences are arranged so that a chimeric protein, which contains a domain of the peptide translated from the first coding sequence, a domain of the transpeptidase translated from the second coding sequence, and the transpeptidase recognition motif translated from the third coding sequence, can be expressed.

Figure 1B:
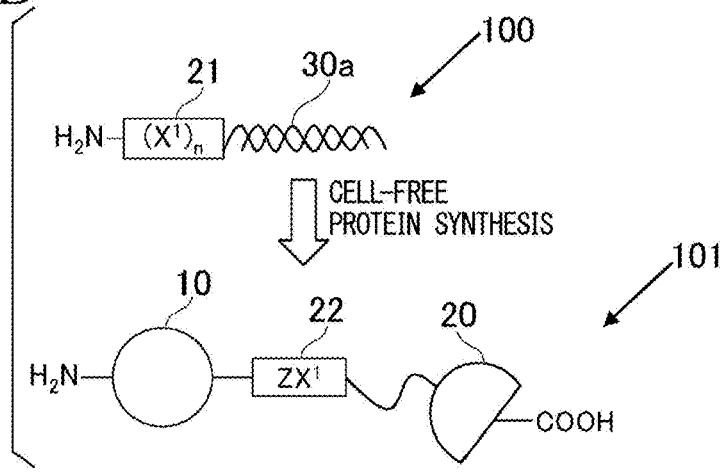
FIG. 1B is a schematic diagram showing an example of a step (B1) in the method for producing a peptide-nucleic acid complex according to the first embodiment of the present invention.

Next, a chimeric protein 101 is synthesized from the NS-added nucleic acid 100 using a cell-free protein synthesis system (FIG. 1B; step (B1)). The chimeric protein 101 contains a domain of a peptide 10, a transpeptidase recognition motif 22, and a domain of a transpeptidase 20. In the chimeric protein 101, the transpeptidase recognition motif 22 is located on the C-terminal side of the domain of the peptide 10. In the chimeric protein 101, the peptide 10, the transpeptidase recognition motif 22, and the transpeptidase 20 are arranged in order from the N-terminal side to the C-terminal side.

Figure 1C:
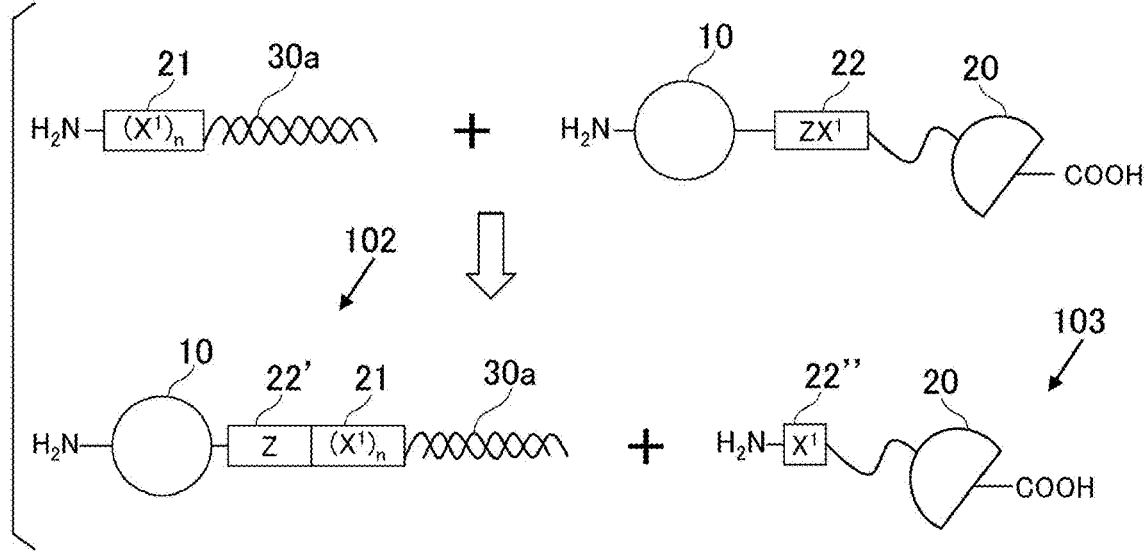
FIG. 1C is a schematic diagram showing an example of a step (C1) in the method for producing a peptide-nucleic acid complex according to the first embodiment of the present invention.

Next, the peptide-nucleic acid complex 102 is formed through a transpeptidation reaction by the domain of the transpeptidase 20 of the chimeric protein 101 (FIG. 1C; step (C1)). In this manner, a peptide-nucleic acid complex can be produced.

Hereinafter, each step of the producing method of this embodiment will be described.

[Step (A1)]

The step (A1) is a step of preparing a nucleic acid to which a transpeptidase N-terminal substrate motif has been added, the nucleic acid containing a first coding sequence encoding a peptide, a second coding sequence encoding a transpeptidase, and a third coding sequence encoding a transpeptidase recognition motif.

(Transpeptidase)

The transpeptidase is not particularly limited; however, a sortase is preferable. The sortase can be used without particular limitation, as long as it can recognize and cleave a sortase recognition motif and bond the N-terminal of a sortase N-terminal substrate motif to the C-terminal of the cleaved sortase recognition motif. Known sortases include a sortase A, a sortase B, a sortase C, and a sortase D. Any one of these sortases can be used in the producing method of this embodiment. The base sequences and amino acid sequences of these sortases are available from known databases such as GenBank.

Examples of the N-terminal substrate motif for a sortase include one or more glycines $((G)_n)$ and one or more alanines $((A)_n)$ (n is an integer of 1 or more). Among them, the N-terminal substrate motif for a sortase is preferably one or more glycines. The number of glycine residues in the N-terminal substrate motif is preferably 1 to 10, more preferably 1 to 8, and still more preferably 1 to 6 or 1 to 5.

The sortase A may be, for example, derived from *Staphylococcus aureus* (*S. aureus*) or *Streptococcus pyogenes* (*S. pyrogenes*). For example, the sequence of the sortase A of *Staphylococcus aureus* is available in NCBI RefSeq Acc. No. NP_187332.1; or GenBank Acc. No. AAD48437.

The recognition motif for the sortase A may include, for example, an amino acid sequence of $X^A P X^B X^C$ or $X^A P X^B X^C G$. In the above, $X^A$ is leucine, isoleucine, valine or methionine; $X^B$ is any amino acid; $X^C$ is threonine, serine or alanine; P is proline; and G is glycine. In a preferred embodiment, $X^A$ is leucine; $X^C$ is threonine; and $X^B$ may be aspartate, glutamate, alanine, glutamine, lysine, or methionine. Specific examples of the recognition motif for the sortase A include LPXTG (SEQ ID NO: 1) (LPATG (SEQ ID NO: 2), LPNTG (SEQ ID NO: 3), or the like), LPXAG (SEQ ID NO: 4) (LPNAG (SEQ ID NO: 5) or the like), LPXTA (SEQ ID NO: 6) (LPNTA (SEQ ID NO: 7) or the like), LGXTG (SEQ ID NO: 8) (LGATG (SEQ ID NO: 9) or the like), and IPXTG (SEQ ID NO: 10) (IPNTG (SEQ ID NO: 11), IPETG (SEQ ID NO: 12), or the like) (X represents any amino acid). Among these, the recognition motif for the sortase A is preferably LPXTG (SEQ ID NO: 1).

The sortase A is not limited to the wild-type protein and may be a variant as long as the variant has transpeptidase activity. For example, a variant of the sortase A of *Staphylococcus aureus* may contain His at the position 120, Cys at the position 184, and Arg at the position 197, and the recognition motif therefor may be TLXTC (SEQ ID NO: 13). The variant of the sortase A may be composed of an amino acid sequence having a sequence identity of 80% or more (for example, 85% or more, 90% or more, 91% or more, 92% or more, 93% or more, 94% or more, 95% or more, 96% or more, 97% or more, 98% or more, or 99% or more) with respect to the amino acid sequence of the wild-type sortase A or the amino acid sequence of the catalytic domain of the wild-type sortase A and having transpeptidase activity. Alternatively, the variant of the sortase A may be composed of an amino acid sequence in which one or some amino acids (for example, 2 to 15 amino acids: 2 amino acids, 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, or 15 amino acids) are deleted, substituted, added or inserted with respect to the amino acid sequence of the wild-type sortase A, and has transpeptidase activity.

For example, a variant of the sortase A of *Staphylococcus aureus* has been found (Chen, I., et al., PNAS 108 (28): 11399 to 11404, 2011), where the variant of the sortase A has a maximally 140-fold increased bonding activity to the LPETG (SEQ ID NO: 14) motif as compared with the wild-type sortase A of *Staphylococcus aureus*, and such a sortase A may be used. For example, the variant of the sortase A may be a variant having at least one mutation in the wild-type sortase A of *Staphylococcus aureus*, the mutation selected from the group consisting of P94S or P94R, E106G, F122Y, K154R, D160N, D165A, G174S, K190E, and K196T. Among them, the variant of the sortase A preferably has at least one mutation selected from the group consisting of P94S or P94R, D160N, D165A, G174S, and K196T and more preferably has all of these mutations.

Further, the sortase A may have a modified recognition motif. For example, Piotukh et al. (J Am Chem Soc. 2011 Nov. 9; 133 (44): 17536 to 17539) describes a variant of the sortase A whose recognition motif is XPXTG (SEQ ID NO: 15). Dorr et al. (Proc Natl Acad Sci US A. 2014 Sep. 16; 111 (37): 13343 to 13348) describes a variant of the sortase A whose recognition motif is LAXTG (SEQ ID NO: 16) or LPXSG (SEQ ID NO: 17). The transpeptidase that is used in the producing method of the present embodiment may be selected from these variants of the sortase A.

The sortase B may be, for example, derived from *Staphylococcus aureus* (*S. aureus*), *Bacillus anthracis* (*B. anthracis*), or *Listeria monocytogenes* (*L. monocytogenes*).

The recognition motif for the sortase B may include an amino acid sequence of $NPX^A TX^B$. In the above, $X^A$ is glutamine or lysine; $X^B$ is asparagine or glycine; N is asparagine; P is proline; and T is threonine. Specific examples of the recognition motif for the sortase B include NPQTN (SEQ ID NO: 18), NPKTG (SEQ ID NO: 19), NSKTA (SEQ ID NO: 20), NPQTG (SEQ ID NO: 21), NAKTN (SEQ ID NO: 22), and NPQSS (SEQ ID NO: 23).

LPXTG (SEQ ID NO: 1) may be used for the sortase C as a recognition motif. The sortase C is presumed to recognize a motif having a common sequence NA-[E/A/S/H]-TG (SEQ ID NO: 24) (Comfort D and Clubb R T. Infect Immun., 72 (5): 2710 to 2722, 2004).

The sortase D may be derived from the genus *Streptomyces*, the genus *Corynebacterium, Tropheryma whipplei, Thermobifida fusca*, or *Bifidobacterium longum*. Examples of the recognition motif for the sortase D include LPXTA (SEQ ID NO: 6) and LAXTG (SEQ ID NO: 16).

Barnett and Scott (Barnett, T C and Scott, J R, Journal of Bacteriology, Vol. 184, No. 8, p. 2181 to 2191, 2002) describes a sortase recognizing a recognition motif of QVPTGV (SEQ ID NO: 25).

The sortase may be a sortase of a Gram-negative bacterium, for example, *Colwellia psychrerythraea, Microbulbifer degradans, Bradyrhizobium japonicum, Shewanella oneidensis*, or *Shewanella putrefaciens*. These may recognize a recognition motif of LP[Q/K]T[A/S]T.

In addition, the sortase may be a sortase derived from archaea (for example, a methanogenic bacterium such as *Methanobacterium* thermoautotrophicum).

The transpeptidase may be a buterase. The buterase can be used without particular limitation, as long as it can recognize and cleave a buterase recognition motif and bond the N-terminal of a buterase N-terminal substrate motif to the C-terminal of the cleaved buterase recognition motif. As a known buterase, a buterase 1 is known (Nguyen G K et al., Nat Protoc. 2016 October; 11 (10): 1977 to 1988, and Published Japanese Translation No. 2017-515468 of the PCT International Publication). The sequence of the buterase 1 is available in GenBank Acc. No. KF918345.

Examples of the N-terminal substrate motif for a buterase include $X^E X^F$. In the above, $X^E$ is any amino acid; and $X^F$ is leucine, isoleucine, valine, or cysteine. The recognition motif for a buterase may be, for example, a motif including an amino acid sequence of $X^D HV$. In the above, $X^D$ is asparagine or aspartic acid; H is histidine; and V is valine.

The buterase is not limited to the wild-type protein and may be a variant as long as the variant has transpeptidase activity. The variant of the buterase may be one which is composed of an amino acid sequence having a sequence identity of 80% or more (for example, 85% or more, 90% or more, 91% or more, 92% or more, 93% or more, 94% or more, 95% or more, 96% or more, 97% or more, 98% or more, or 99% or more) with respect to the amino acid sequence of the wild-type buterase or the catalytic domain thereof and has transpeptidase activity. Alternatively, the variant of the buterase may be one which is composed of an amino acid sequence in which one or some amino acids (for example, 2 to 15 amino acids: 2 amino acids, 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, or 15 amino acids) are deleted, substituted, added, or inserted with respect to the amino acid sequence of the wild-type buterase, and has transpeptidase activity.

Among these, the transpeptidase is preferably a sortase or a buterase, more preferably the sortase A (including a wild type and a modified type) or the buterase 1 (including a wild type and a modified type), and still more preferably the sortase A.

(Nucleic Acid to which Transpeptidase N-Terminal Substrate Motif has been Added: NS-Added Nucleic Acid)

An NS-added nucleic acid is a nucleic acid to which a transpeptidase N-terminal substrate motif has been added to any one of the 5' terminal and the 3' terminal. In the NS-added nucleic acid 100 shown in FIG. 1A, the transpeptidase N-terminal substrate motif 21 is added to the 5' terminal of a nucleic acid 30a. In FIG. 1A, the transpeptidase N-terminal substrate motif 21 is exemplified as a peptide having an amino acid sequence of $(X^1)_n$ (n is 1 or more). In a case where the transpeptidase is sortase, the above $X^1$ is preferably glycine or alanine and more preferably glycine. In a case where the transpeptidase is the buterase 1, the transpeptidase N-terminal substrate motif 21 may be represented by $X^E X^F$ ($X^E$ is any amino acid, and $X^F$ is leucine, isoleucine, valine, or cysteine).

The NS-added nucleic acid 100 contains a first coding sequence encoding any peptide; a second coding sequence encoding a transpeptidase; and a third coding sequence encoding a transpeptidase recognition motif.

The peptide encoded by the first coding sequence is not particularly limited and may be any peptide. Examples of the peptide include a physiologically active peptide and a functional peptide; however, the examples are not limited thereto. Examples of the physiologically active peptide and the functional peptide include an enzyme, an enzyme inhibitory molecule, an enzyme activating molecule, a hormone, a receptor, a cytokine, an antibody, an antigen, an aptamer, a fluorescent protein, an adjuvant, a toxin, a ligand, an adhesive peptide, a chelate-formable peptide, a membrane-permeable peptide, a dominant-negative peptide, and an antibacterial peptide; however the examples are not limited thereto. The first coding sequence may be a sequence of a wild-type gene, a sequence of a modified gene, or a sequence having a silent mutation as long as the first coding sequence encodes the target peptide 10.

The first coding sequence may be derived from a mixture of a plurality of kinds of DNA such as a DNA library. The first coding sequence may be, for example, derived from a mutant DNA library. Examples of the mutant DNA library include a library obtained by using the error-prone PCR, a library obtained by using the gene assembly mutagenesis, a library obtained by using the random insertion and deletion mutagenesis, a library obtained by using the DNA shuffling, a library obtained by using the family shuffling, a library obtained by using the staggered extension process in vitro recombination, an ITCHY hybrid protein library, a SCRATCHY hybrid protein library, a library obtained by using the sequence homology-independent protein recombination, and a library obtained by using the mixture base synthesis with the phosphoramidite method.

The second coding sequence may be a sequence of a wild-type gene, a sequence of a modified gene, or a sequence having a silent mutation as long as the encodes the transpeptidase 20 encodes the transpeptidase 20.

The third coding sequence may be a sequence of a wild-type gene, a sequence of a modified gene, or a sequence having a silent mutation as long as the third sequence encodes the transpeptidase recognition motif 22.

In the NS-added nucleic acid 100, the first coding sequence, the third coding sequence, and the second coding sequence are arranged in order from the 5' side to the 3' side (see FIG. 1 (A)). In addition, in the NS-added nucleic acid 100, these sequences are arranged so that a chimeric protein, which is the chimeric protein 101 that contains a domain of the peptide 10 translated from the first coding sequence, a domain of the transpeptidase 20 translated from the second coding sequence, and a transpeptidase recognition motif 22 translated from the third coding sequence and in which the transpeptidase recognition motif 22 is located on the C-terminal side of the domain of peptide 10, can be expressed (see FIG. 1B). That is, the first coding sequence, the third coding sequence, and the second coding sequence are linked in-frame in order from the 5' side to the 3' side in one ORF with or without the interposition of any base sequence.

The NS-added nucleic acid 100 may have another base sequence in addition to the first coding sequence, the second coding sequence, and the third coding sequence. Examples of the other base sequence include a regulatory sequence that regulates transcription and/or translation of an ORF containing the first coding sequence, the second coding sequence, and the third coding sequence. Examples of such a regulatory sequence include a promoter, a terminator, a transcription-promoting sequence, a translation-promoting sequence, and a Shine-Dalgarno sequence. As the regulatory sequence, a regulatory sequence capable of regulating transcription and/or translation of the ORF can be appropriately selected depending on a cell-free protein synthesis system that is used in the step (B1) that will be described later.

Examples of the promoter include a T7 promoter, an SP6 promoter, and a T3 promoter. The ORF is preferably linked functionally to the promoter to be expressed under the regulation of the promoter.

The NS-added nucleic acid 100 may have a sequence which encodes any spacer between the first coding sequence and the third coding sequence or/and between the third coding sequence and the second coding sequence. For example, the NS-added nucleic acid 100 may have a sequence which encodes any spacer between the second coding sequence and the third coding sequence. In a case where a spacer is contained, the transpeptidase 20 is easily bonded to the transpeptidase recognition motif 22 in the chimeric protein 101 which has been expressed from the NS-added nucleic acid 100.

The method for adding the transpeptidase N-terminal substrate motif 21 to the nucleic acid 30a is not particularly limited, and a known method can be used. For example, a nucleic acid 30a can be amplified by PCR or the like using a primer to which the transpeptidase N-terminal substrate motif 21 has been added, and thus the nucleic acid 30a to which the transpeptidase N-terminal substrate motif 21 has been added (the NS-added nucleic acid 100) can be obtained.

The transpeptidase N-terminal substrate motif 21 may be added to any one of the forward primer or the reverse primer. For example, the transpeptidase N-terminal substrate motif 21 may be added to the 5' terminal of the forward primer, or the transpeptidase N-terminal substrate motif 21 may be added to the 5' terminal of the reverse primer.

The method for adding the transpeptidase N-terminal substrate motif 21 to the primer is not particularly limited, and a known method can be used. For example, various methods used in click chemistry can be used. Examples of such a method include a method by a Huisgen reaction (a combination of a nucleic acid-azide and a peptide-alkyne may be used, or a combination of a nucleic acid-alkyne and a peptide-azide may be used); and a method in which copper-free cyclooctyne, DBCO, BARAC, or the like is used.

Further, the bonding method is not limited to a method used in click chemistry, and the transpeptidase N-terminal substrate motif 21 may be bonded to the nucleic acid 30a using an activator, a cross-linking agent, or the like via an amino group, a carboxyl group, a thiol group, or the like. Further, a nucleophilic substitution reaction using bromine or iodine, a reaction between an aldehyde/ketone and a hydrazide, a reaction between a propargyl ester and an amino group, a photo-crosslinking reaction, or the like may be used.

Further, the transpeptidase N-terminal substrate motif 21 may be added to the nucleic acid 30a by a method of bonding the transpeptidase N-terminal substrate motif 21 to the terminal functional group of the nucleic acid 30a. For example, after amplifying the nucleic acid 30a by the PCR method or the like, the transpeptidase N-terminal substrate motif 21 may be added to the terminal of the nucleic acid 30a. As a method for adding the transpeptidase N-terminal substrate motif 21, the same method as the method described above can be used.

The NS-added nucleic acid 100 prepared in this step may be immobilized on a solid phase carrier. The solid phase carrier is not particularly limited, and examples thereof include a bead (a magnetic bead, a gold nanoparticle, an agarose bead, a plastic bead, or the like) and a micro well plate. Among them, the solid phase carrier is preferably a magnetic bead since the magnetic bead can be easily recovered and arranged at any position.

The method for immobilizing the nucleic acid on the solid phase carrier is not particularly limited, and a known method can be used. For example, methods such as a method of utilizing an avidin-biotin binding; a method in which a nucleic acid is modified with a functional group such as an amino group, a formyl group, or an SH group, and a solid phase carrier subjected to a surface treatment with a silane coupling agent having an amino group, a formyl group, an epoxy group, or the like is used; and a method of using gold-thiol binding can be used. Among them, a method of utilizing an avidin-biotin binding is suitably used.

In a case where the nucleic acid 30a is amplified by the PCR method, a primer set in which one primer has been immobilized on a solid phase carrier may be used so that the amplified nucleic acid 30a has been immobilized on the solid phase carrier. For example, in a case where the transpeptidase N-terminal substrate motif 21 is added to the 5' terminal of the forward primer, the 5' terminal of the reverse primer can be immobilized on a solid phase carrier. Alternatively, in a case where the transpeptidase N-terminal substrate motif 21 is added to the 5' terminal of the reverse primer, the 5' terminal of the forward primer can be immobilized on a solid phase carrier. As a method for immobilizing the primer on the solid phase carrier, the same method as the method described above can be used.

(Emulsion PCR)

The PCR may be emulsion PCR. For example, in a case where the nucleic acid 30a is amplified by a PCR method using a primer set in which one primer has been immobilized on a bead, the emulsion PCR can be performed. The emulsion PCR is a method in which one bead on which one molecule of a template nucleic acid or a primer has been immobilized is compartmentalized in an emulsion, and PCR is performed in the emulsion using the primer. In a case where one primer is immobilized on a bead, each bead is compartmentalized in one emulsion, PCR is performed in the emulsion, and thus one kind of nucleic acid can be amplified and immobilized on the surface of the bead. In addition, in a case where the primer is not immobilized on the bead, one molecule of a template nucleic acid may be compartmentalized in one emulsion, and then PCR may be performed in the emulsion. This makes it possible to amplify the same kind of nucleic acid in the emulsion.

The kind of emulsion used in the emulsion PCR is not particularly limited; however, it is preferable to use a water-in-oil (W/O) type emulsion because it is easily prepared and the subsequent operations are simplified. The emulsion may be prepared by a conventional method. For example, an oily component and an emulsifying agent are mixed with an aqueous component containing the nucleic acid 30a, a primer set immobilized on a bead, and a reagent necessary for nucleic acid amplification such as a DNA polymerase, and the mixture is stirred, whereby a W/O type emulsion can be obtained. This makes it possible to compartmentalize one molecule of nucleic acid 30a and one bead in one emulsion particle. For the preparation of the emulsion, for example, stirring treatment (use of a magnetic stirring bar, a propeller type system, or the like), homogenization (use of a homogenizer, a mortar, or the like), ultrasonic treatment (use of a sonicator or the like) can be used.

The size of the emulsion particle is not particularly limited as long as the emulsion particle can enclose one molecule of nucleic acid 30a and one bead. The average particle size of the emulsion particles is, for example, preferably 1 µm to 100 µm, more preferably 5 µm to 50 µm, and particularly preferably 10 µm to 30 µm. In a case where the primer is not immobilized on the bead, the average particle size of the emulsion particles may be a size required for enclosing one molecule of a template nucleic acid, and the sized can be, for example, 1 nm or more, 10 nm or more, or 50 nm or more. The upper limit of the average particle size can be, for example, 100 µm or less, 50 µm or less, or 30 µm or less, as described above.

The number of emulsion particles is calculated by dividing the volume of the aqueous component by the volume of one emulsion. Accordingly, in order to prepare a W/O type emulsion so that an average of one molecule or fewer of a template nucleic acid is contained in one emulsion, the nucleic acid 30a is prepared so that the number thereof is equal to or less than the total number of emulsions.

Examples of the emulsifying agent used for preparing the emulsion include ABIL (registered trademark) WE09, ABIL (registered trademark) WS08, and ABIL (registered trademark) EM90, which are manufactured by Goldschmidt AG. As the oily component used for preparing the emulsion, mineral oil is generally used.

After the emulsion PCR, the emulsion may be destroyed to recover the bead on which the NS-added nucleic acid 100 has been immobilized. After recovery, the bead may be washed with an appropriate wash buffer or the like. Similarly, even in a case where the NS-added nucleic acid 100 is not immobilized on the bead, the emulsion may be destroyed, and the NS-added nucleic acid 100 may be recovered.

In the producing method of this embodiment, since one kind of NS-added nucleic acid 100 per one bead is presented, the NS-added nucleic acid 100 is preferably prepared by the emulsion PCR using a primer immobilized on the bead.

However, the method for presenting one kind of NS-added nucleic acid 100 per one bead is not limited to the emulsion PCR. For example, a method in which one molecule of nucleic acid 30a and one bead are compartmentalized in one reaction chamber and a PCR reaction is carried out may be used.

[Step (B1)]

The step (B1) is a step of synthesizing a chimeric protein containing a domain of the peptide, a domain of the transpeptidase, and the transpeptidase recognition motif, from the nucleic acid to which the transpeptidase N-terminal substrate motif has been added, using a cell-free protein synthesis system.

(Chimeric Protein)

The chimeric protein 101 is a protein that is transcribed and translated from the nucleic acid 30a. The chimeric protein 101 contains the domain of the peptide 10, the domain of the transpeptidase 20, and the transpeptidase recognition motif 22. In the chimeric protein 101, the domain of the peptide 10, the transpeptidase recognition motif 22, and the domain of the transpeptidase 20 are arranged in order from the N-terminal side to the C-terminal side.

In FIG. 1B, the transpeptidase recognition motif 22 is exemplified as a peptide having an amino acid sequence of $ZX^1$ (Z represents a sequence obtained by excluding the C-terminal amino acid residue from the transpeptidase recognition motif, and $X^1$ represents the C-terminal amino acid residue in the transpeptidase recognition motif). In a case where the transpeptidase is sortase, the above $X^1$ is preferably glycine or alanine and more preferably glycine. Examples of Z include a sequence obtained by removing the C-terminal amino acid residue from the sequence exemplified as the above-described sortase recognition motif. Specific examples thereof include LPXT (SEQ ID NO: 31) (LPAT (SEQ ID NO: 32), LPNT (SEQ ID NO: 33), or the like), LPXA (SEQ ID NO: 34) (LPNA (SEQ ID NO: 35) or the like), LPXT (SEQ ID NO: 36) (LPNT (SEQ ID NO: 37) or the like), LGXT (SEQ ID NO: 38) (LGAT (SEQ ID NO: 39) or the like), and IPXT (SEQ ID NO: 40) (IPNT (SEQ ID NO: 41), IPET (SEQ ID NO: 42), or the like) (X represents any amino acid). In a case where the transpeptidase is a buterase, the transpeptidase recognition motif 22 may be represented by $X^DHV$ ($X^D$ is asparagine or aspartic acid; H is histidine; and V is valine).

(Cell-Free Protein Synthesis System)

The chimeric protein 101 is synthesized from the NS-added nucleic acid 100 using a cell-free protein synthesis system.

The cell-free protein synthesis system is a system in which an mRNA or a protein, which is encoded from a nucleic acid (a DNA or an mRNA) that is a template, can be synthesized in vitro, instead of using living cells, by using ribosomes derived from living cells (or obtained by a genetic engineering method), transcription factors, translation factors, or the like. In the cell-free protein synthesis system, a cell extract obtained from a cell disruption solution by carrying out purification as necessary is generally used. The cell extract generally contains ribosomes, various factors such as initiation factors, tRNAs, and various enzymes such as RNA polymerases and aminoacyl tRNA synthases, which are required for protein synthesis. In a case where protein synthesis is carried out, other substances necessary for protein synthesis such as various amino acids, energy sources such as ATP and GTP, and creatine phosphate are added to the cell extract. In addition, ribosomes, various factors, and/or various enzymes, which are separately prepared, may be supplemented as necessary.

Examples of the widely used cell-free protein synthesis system include an *Escherichia coli* S30 extract system (a prokaryotic cell system), a wheat germ extract system (a eukaryotic cell system), and a rabbit reticulocyte lysate system (a eukaryotic cell system). Reagents required for these cell-free protein synthesis systems are commercially available as kits and thus can be easily used.

The cell-free protein synthesis system may be a transcription and translation system in which each molecule (factor) required for protein synthesis is reconstituted (for example, Shimizu, Y. et al.: Nature Biotech., 19, 751 to 755, 2001). In the reconstituted cell-free protein synthesis system, a protein synthesis system is reconstituted in vitro using 31 kinds of factors, which are amplified from the *Escherichia coli* genome, consisting of 3 kinds of initiation factors that constitute the bacterial protein synthesis system, 3 kinds of elongation factors, 4 kinds of factors involved in termination, 20 kinds of aminoacyl tRNA synthases each of which binds the corresponding amino acid to the corresponding tRNA, and one methionyl-tRNA formyltransferase.

The synthesis of the chimeric protein 101 from the NS-added nucleic acid 100 using the cell-free protein synthesis system may be carried out in an emulsion. In a case where the NS-added nucleic acid 100 is immobilized on a bead, one bead can be compartmentalized in one emulsion particle. In a case where one kind of NS-added nucleic acid 100 per one bead is presented in the step (A1), it is possible to cause the one kind of NS-added nucleic acid 100 and the chimeric protein 101 synthesized from the NS-added nucleic acid 100 to coexist in one emulsion particle.

Even in a case where the NS-added nucleic acid 100 is not immobilized on the bead, one molecule of the NS-added nucleic acid 100 may be compartmentalized in one emulsion particle, and then the chimeric protein 101 may be synthesized in the emulsion by the cell-free protein synthesis system. Also in this case, it is possible to cause the one kind of NS-added nucleic acid 100 and the chimeric protein 101 synthesized from the NS-added nucleic acid 100 to coexist in one emulsion particle.

The method for preparing the emulsion, the size of the emulsion particles, and the like can be the same as those exemplified in the above "[Step (A1)]".

In the producing method of this embodiment, since one kind of NS-added nucleic acid 100 and the chimeric protein 101 synthesized from the nucleic acid are caused to coexist in one compartment, it is preferable to perform cell-free protein synthesis in the emulsion.

However, the method of causing one kind of NS-added nucleic acid 100 and the chimeric protein 101 synthesized from the nucleic acid to coexist in one compartment is not limited to the cell-free protein synthesis in the emulsion. For example, a method in which one bead presenting one kind of NS-added nucleic acid 100 is compartmentalized in one reaction chamber and the cell-free protein synthesis is carried out may be used.

[Step (C1)]

The step (C1) is a step of forming a peptide-nucleic acid complex through a transpeptidation reaction by the transpeptidase domain of the chimeric protein synthesized in the step (B1).

In the step (B1), the chimeric protein 101 synthesized from the NS-added nucleic acid 100 contains the domain of the transpeptidase 20 and the transpeptidase recognition motif 22. As a result, the transpeptidase recognition motif 22 in the chimeric protein 101 is recognized by the domain of the transpeptidase 20, cleaved at a predetermined position in the motif, and divided into a sequence 22' and a sequence 22", and the C-terminal of the sequence 22' is linked to a cysteine residue in the domain of the transpeptidase 20 by a thioester bond. As a result, a protein A contains the domain of the peptide 10, and the sequence 22' and a transpeptidation reaction product 103 which contains the transpeptidase 20 and the sequence 22" are linked by a thioester bond.

Next, through the transpeptidation reaction, the N-terminal of the transpeptidase N-terminal substrate motif 21 of the NS-added nucleic acid 100 is bonded to the C-terminal of the sequence 22' in the protein A. As a result, the peptide-nucleic acid complex 102 containing the peptide 10 and the nucleic acid 30a encoding the peptide is formed. At the same time, the transpeptidation reaction product 103 is formed.

In the example of FIG. 1C, the transpeptidase recognition motif 22 is represented as a sequence consisting of $ZX^1$ as in FIG. 1B. The transpeptidase N-terminal substrate motif 21 is represented by $(X^1)n$.

First, the peptide bond between Z and $X^1$ is cleaved by the transpeptidase activity of the domain of the transpeptidase 20 in the chimeric protein 101. As a result, the transpeptidase recognition motif 22 is divided into the sequence 22' and the sequence 22". The sequence 22" is a sequence consisting of Z, and the sequence 22" is a sequence consisting of $X^1$. Next, a novel peptide bond is formed between the C-terminal amino acid residue of the sequence 22' and the N-terminal amino acid $X^1$ of the transpeptidase N-terminal substrate motif 21 of the NS-added nucleic acid 100. As a result, the peptide-nucleic acid complex 102 and the transpeptidation reaction product 103 are generated.

In a case where the transpeptidase is a buterase, the transpeptidase recognition motif 22 may be represented by $X^D HV$ ($X^D$ is asparagine or aspartic acid; H is histidine; and V is valine). In a case where the transpeptidase is the buterase 1, the transpeptidase N-terminal substrate motif 21 may be represented by $X^E X^F$ ($X^E$ is any amino acid, and $X^F$ is leucine, isoleucine, valine, or cysteine).

In this case, first, the peptide bond between $X^D$ and H is cleaved by the transpeptidase activity of the domain of the transpeptidase 20 in the chimeric protein 101. As a result, the transpeptidase recognition motif 22 is divided into $X^D$ (corresponding to the above sequence 22') and HV (corresponding to the above sequence 22"). Next, a novel peptide bond is formed between the C-terminal amino acid residue ($X^D$) of the cleaved transpeptidase recognition motif 22 and the N-terminal amino acid sequence $X^E X^F$ of the transpeptidase N-terminal substrate motif 21 of the NS-added nucleic acid 100. As a result, the peptide-nucleic acid complex 102 and the transpeptidation reaction product 103 are generated.

The peptide-nucleic acid complex 102 obtained by this step contains (a) the peptide 10; (b) a sequence generated by bonding the transpeptidase recognition motif 22 and the transpeptidase N-terminal substrate motif 21 through the transpeptidation reaction by a transpeptidase; and (c) the nucleic acid 30a encoding the peptide 10. Further, the sequence of (b) is located between the peptide 10 and the nucleic acid 30a.

In the present specification, "sequence generated by bonding a transpeptidase recognition motif and a transpeptidase N-terminal substrate motif" (hereinafter, may be referred to as a "TPR-NS sequence") means a sequence generated by bonding the N-terminal of the transpeptidase N-terminal substrate motif to the C-terminal of the sequence generated by cleaving the transpeptidase recognition motif by transpeptidase. In the example of FIG. 1C, the TPR-NS sequence is a sequence represented by $Z(X^1)_n$.

In a case where the transpeptidase is a sortase, the TPR-NS sequence generally contains the same sequence as the transpeptidase recognition motif. Accordingly, examples of the TPR-NS sequence include the sequence described above as the sortase recognition motif.

In a case where the transpeptidase is a buterase, examples of the TPR-NS sequence include a sequence represented by $X^D X^E X^F$ ($X^D$ is asparagine or aspartic acid; $X^E$ is any amino acid; $X^F$ is leucine, isoleucine, valine, or cysteine).

In the chimeric protein 101, since the domain of the transpeptidase 20 is located on the C-terminal side of the transpeptidase recognition motif 22, the domain of the transpeptidase 20 is removed by the transpeptidation reaction. As a result, the peptide-nucleic acid complex 102 has a structure in which the peptide 10 is bonded to a nucleic acid 30b via the TPR-NS sequence (see FIG. 1C).

The step (C1) may be carried out under conditions in which the transpeptidase can exhibit transpeptidase activity and generally can be carried out simultaneously with the Step (B1).

[Other Steps]

The producing method of this embodiment may include other steps in addition to the above steps (A1) to (C1). The other steps are not particularly limited, and examples thereof include a step of recovering a nucleic acid, a chimeric protein, or a peptide-nucleic acid complex, a washing step, and a purification step.

According to the producing method of this embodiment, a peptide-nucleic acid complex can be produced without requiring complicated work such as the preparation of a linker. Further, in the peptide-nucleic acid complex obtained by the producing method of this embodiment, the TPR-NS sequence is present between the peptide and the nucleic acid. Since the TPR-NS sequence is generally a short sequence of about 5 to 10 amino acids, the three-dimensional structure or function of the peptide is unlikely to be impaired in the peptide-nucleic acid complex. As a result, the peptide-nucleic acid complex can be suitably used for screening a peptide array for a peptide having a desired function, and the nucleic acid encoding the peptide obtained by screening can be easily identified.

Second Embodiment

Figure 2A:
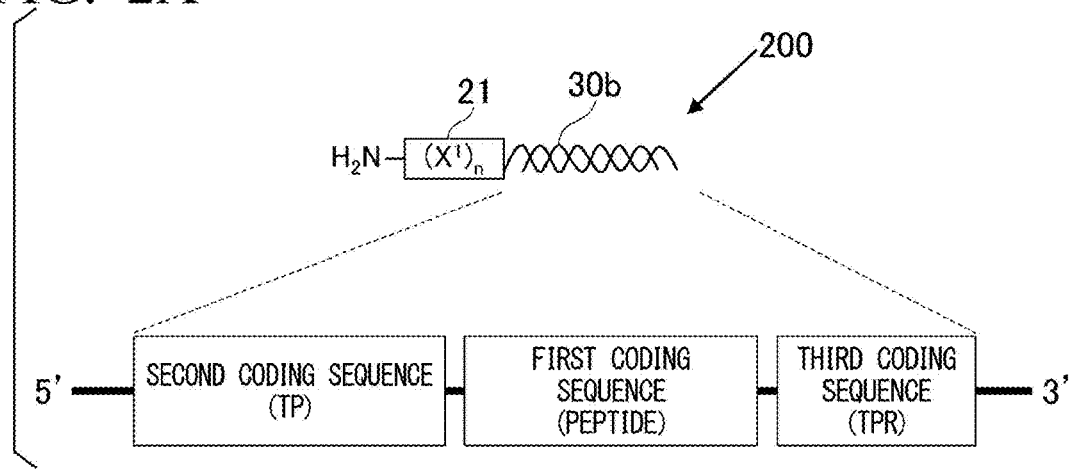
FIG. 2A is a schematic diagram showing an example of a step (A1) in a method for producing a peptide-nucleic acid complex according to the second embodiment of the present invention. An example of a nucleic acid to which a transpeptidase N-terminal substrate motif has been added is shown.

An outline of the second embodiment of the producing method according to this aspect will be described with reference to FIGS. 2A to 2C.

In this embodiment, as the nucleic acid to which the transpeptidase N-terminal substrate motif 21 has been added, a nucleic acid (hereinafter, may be referred to as an "NS-added nucleic acid 200") obtained by adding the transpeptidase N-terminal substrate motif 21 to the nucleic acid 30b in which the second coding sequence encoding a transpeptidase, the first coding sequence encoding a peptide, and a third coding sequence encoding a transpeptidase recognition motif are arranged in order from the 5' side to the 3' side is used (see FIG. 2A).

The NS-added nucleic acid 200 may have a sequence which encodes any spacer between the second coding sequence and the first coding sequence or/and between the first coding sequence and the third coding sequence. For example, the NS-added nucleic acid 200 may have a sequence which encodes any spacer between the second coding sequence and first coding sequence. In a case where a spacer is contained, the transpeptidase 20 is easily bonded to the transpeptidase recognition motif 22 in the chimeric protein 201 which has been expressed from the NS-added nucleic acid 200.

The producing method of this embodiment can be carried out in the same manner as in the first embodiment except that the NS-added nucleic acid 200 is used instead of the NS-added nucleic acid 100 of the first embodiment.

Figure 2B:
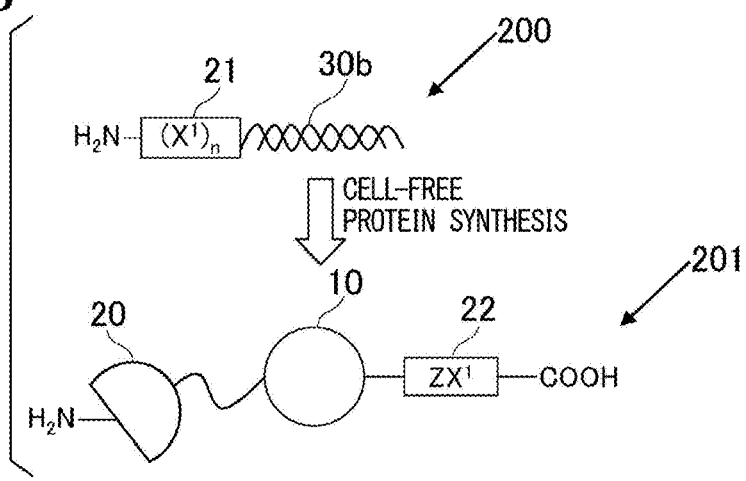
FIG. 2B is a schematic diagram showing an example of a step (B1) in the method for producing a peptide-nucleic acid complex according to the second embodiment of the present invention.
Figure 2C:
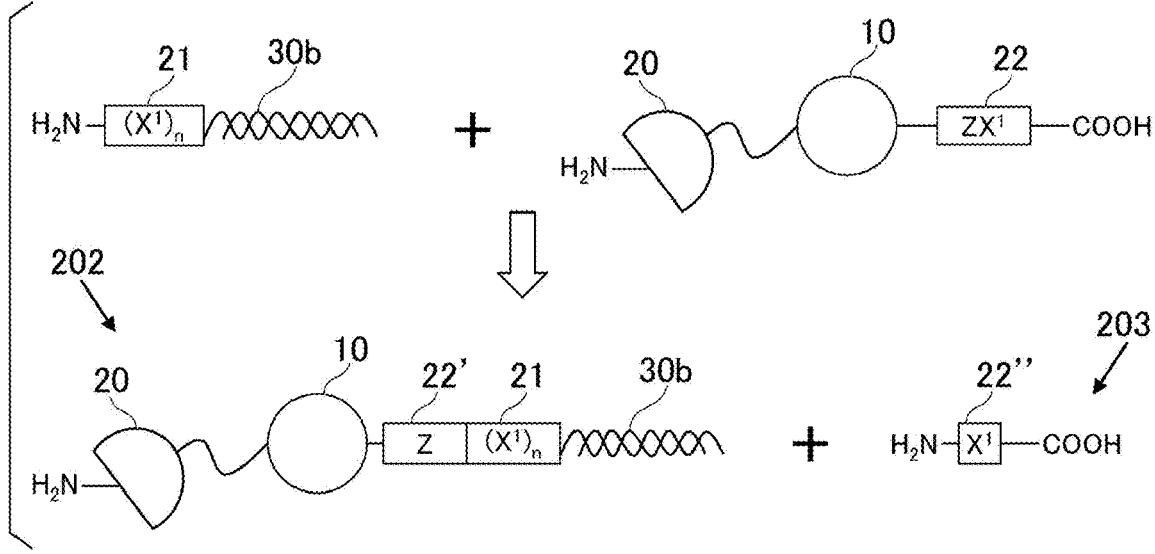
FIG. 2C is a schematic diagram showing an example of a step (C1) in the method for producing a peptide-nucleic acid complex according to the second embodiment of the present invention.

The chimeric protein 201 synthesized from the NS-added nucleic acid 200 using the cell-free protein synthesis system has a configuration in which the domain of the transpeptidase 20, the domain of the peptide 10 domain, and the transpeptidase recognition motif 22 are arranged in order from the N-terminal side to the C-terminal side (see FIG. 2B).

A peptide-nucleic acid complex 202 and a transpeptidation reaction product 203 are generated from the NS-added nucleic acid 200 and the chimeric protein 201 through the transpeptidation reaction by the transpeptidase 20 in the chimeric protein 201.

In the chimeric protein 201, since the domain of the transpeptidase 20 is located on the N-terminal side of the transpeptidase recognition motif 22, the domain of the transpeptidase 20 is not removed by the transpeptidation reaction. As a result, the peptide-nucleic acid complex 202 has a structure in which a chimeric protein containing the transpeptidase 20 and the peptide 10 is bonded to a nucleic acid 30*b* via the TPR-NS sequence (see FIG. 2C).

Third Embodiment

Figure 3A:
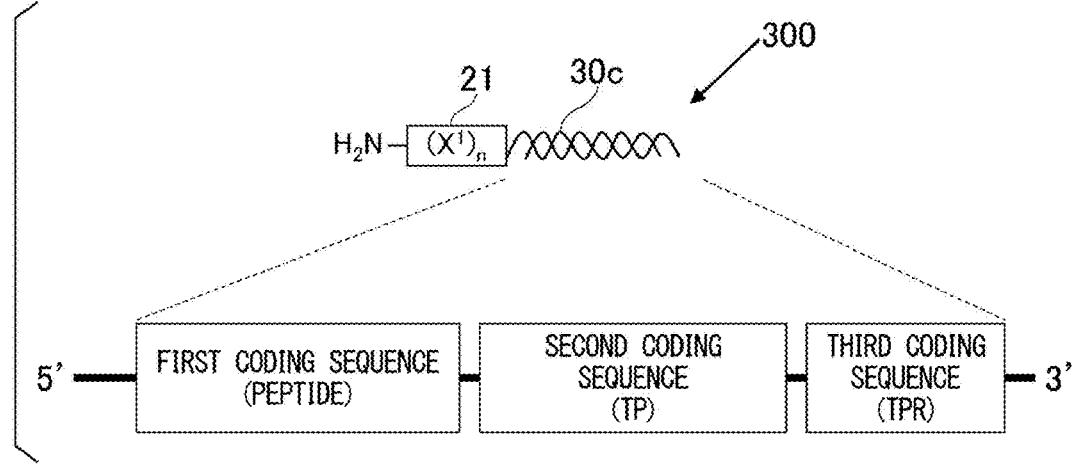
FIG. 3A is a schematic diagram showing an example of a step (A1) in a method for producing a peptide-nucleic acid complex according to the third embodiment of the present invention. An example of a nucleic acid to which a transpeptidase N-terminal substrate motif has been added is shown.

An outline of the third embodiment of the producing method according to this aspect will be described with reference to FIGS. 3A to 3C.

In this embodiment, as the nucleic acid to which the transpeptidase N-terminal substrate motif 21 has been added, a nucleic acid (hereinafter, may be referred to as an "NS-added nucleic acid 300") obtained by adding the transpeptidase N-terminal substrate motif 21 to the nucleic acid 30*c* in which the first coding sequence encoding a peptide, the second coding sequence encoding a transpeptidase, and a third coding sequence encoding a transpeptidase recognition motif are arranged in order from the 5' side to the 3' side is used (see FIG. 3A).

The NS-added nucleic acid 300 may have a sequence which encodes any spacer between the first coding sequence and the second coding sequence or/and between the second coding sequence and the third coding sequence. For example, the NS-added nucleic acid 300 may have a sequence which encodes any spacer between the second coding sequence and the third coding sequence. In a case where a spacer is contained, the transpeptidase 20 is easily bonded to the transpeptidase recognition motif 22 in the chimeric protein 301 which has been expressed from the NS-added nucleic acid 300.

The producing method of this embodiment can be carried out in the same manner as in the first embodiment except that the NS-added nucleic acid 300 is used instead of the NS-added nucleic acid 100 of the first embodiment.

Figure 3B:
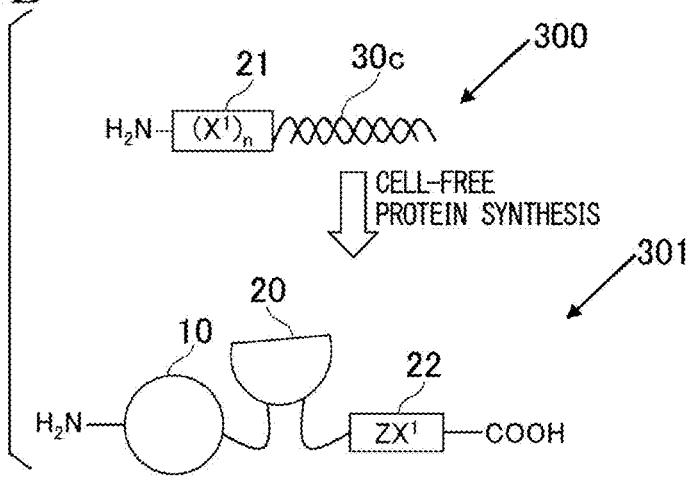
FIG. 3B is a schematic diagram showing an example of a step (B1) in the method for producing a peptide-nucleic acid complex according to the third embodiment of the present invention.
Figure 3C:
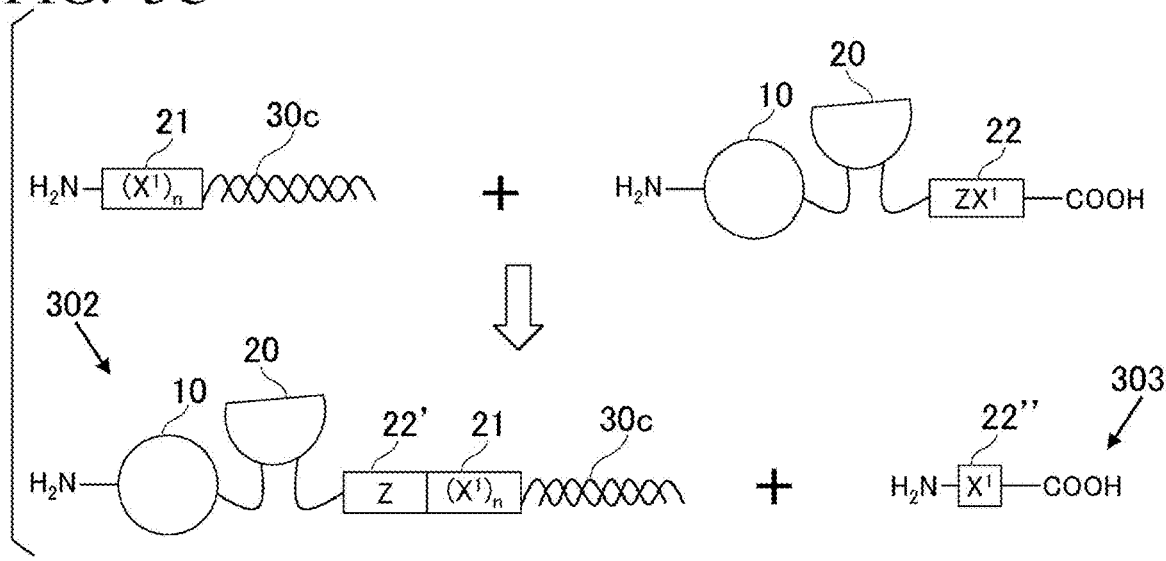
FIG. 3C is a schematic diagram showing an example of a step (C1) in the method for producing a peptide-nucleic acid complex according to the third embodiment of the present invention.

The chimeric protein 301 synthesized from the NS-added nucleic acid 300 using the cell-free protein synthesis system has a configuration in which the domain of the peptide 10 domain, the domain of the transpeptidase 20, and the transpeptidase recognition motif 22 are arranged in order from the N-terminal side to the C-terminal side (see FIG. 3B).

A peptide-nucleic acid complex 302 and a transpeptidation reaction product 303 are generated from the NS-added nucleic acid 300 and the chimeric protein 301 through the transpeptidation reaction by the transpeptidase 20 in the chimeric protein 301.

In the chimeric protein 301, since the domain of the transpeptidase 20 is located on the N-terminal side of the transpeptidase recognition motif 22, the domain of the transpeptidase 20 is not removed by the transpeptidation reaction. As a result, the peptide-nucleic acid complex 302 has a structure in which a chimeric protein containing the peptide 10 and the transpeptidase 20 is bonded to a nucleic acid 30*c* via the TPR-NS sequence (see FIG. 3C).

The fact that the first coding sequence is located on the 5' side of the third coding sequence is common to the nucleic acids 30*a*, 30*b*, and 30*c* according to the first to third embodiments according to this aspect. Further, the fact that the domain of the peptide 10 is located on the N-terminal side of the transpeptidase recognition motif 22 is common to the chimeric proteins 101, 201, and 301, which are respectively expressed from the nucleic acids 30*a*, 30*b*, and 30*c*.

In a case where a transpeptidase (for example, a buterase 1) having high compatibility with the transpeptidase recognition motif located at the C-terminal is used as the transpeptidase, the second embodiment or the third embodiment is preferable.

<<Second Aspect>>

In one embodiment, the present invention provides a method for producing a peptide-nucleic acid complex containing a peptide and a nucleic acid encoding the peptide. The producing method includes (A2) a step of preparing a nucleic acid to which a transpeptidase recognition motif has been added, the nucleic acid containing a first coding sequence encoding the peptide, a second coding sequence encoding a transpeptidase, and a third coding sequence encoding a transpeptidase N-terminal substrate motif; (B2) a step of synthesizing a chimeric protein containing a domain of the peptide, a domain of the transpeptidase, and the transpeptidase N-terminal substrate motif, from the nucleic acid to which the transpeptidase recognition motif has been added, using a cell-free protein synthesis system; and (C2) a step of forming the peptide-nucleic acid complex through a transpeptidation reaction by the transpeptidase domain of the chimeric protein.

Fourth Embodiment

An outline of the fourth embodiment of the producing method according to this aspect will be described with reference to FIGS. 4A to 4C.

First, a nucleic acid 400 (hereinafter, may be referred to as a "TPR-added nucleic acid 400") to which the transpeptidase recognition motif 22 has been added is prepared (FIG. 4A; step (A2)). The TPR-added nucleic acid 400 contains a first coding sequence encoding any peptide; a second coding sequence encoding a transpeptidase; and a third coding sequence encoding the transpeptidase N-terminal substrate motif. In the TPR-added nucleic acid 400, the third coding sequence, the first coding sequence, and the second coding sequence are arranged in order from the 5' side to the 3' side.

Further, in the TPR-added nucleic acid 400, these coding sequences are arranged so that a chimeric protein, which contains a domain of the peptide translated from the first coding sequence, a domain of the transpeptidase translated from the second coding sequence, and the transpeptidase N-terminal substrate motif translated from the third coding sequence, can be expressed.

Figure 4A:
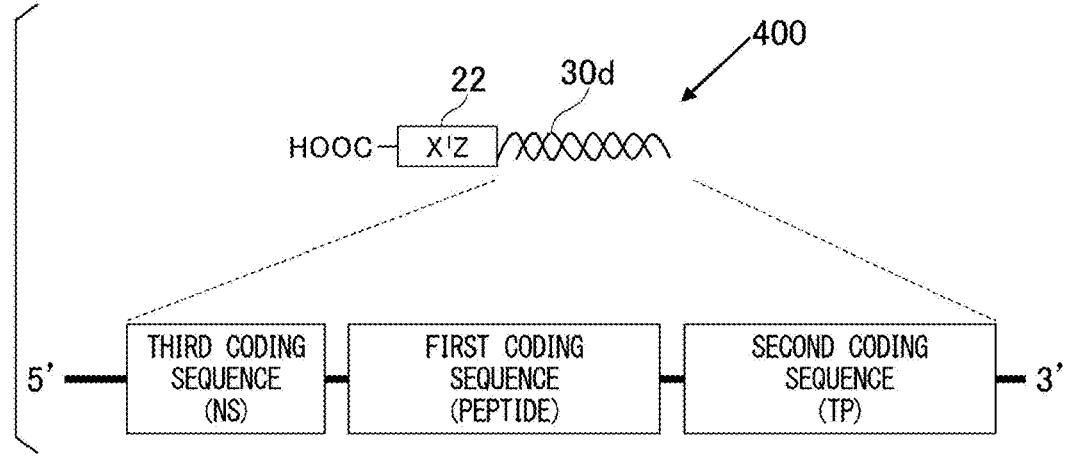
FIG. 4A is a schematic diagram showing an example of a step (A2) in a method for producing a peptide-nucleic acid complex according to the fourth embodiment of the present invention. An example of a nucleic acid to which a transpeptidase recognition motif has been added is shown.
Figure 4B:
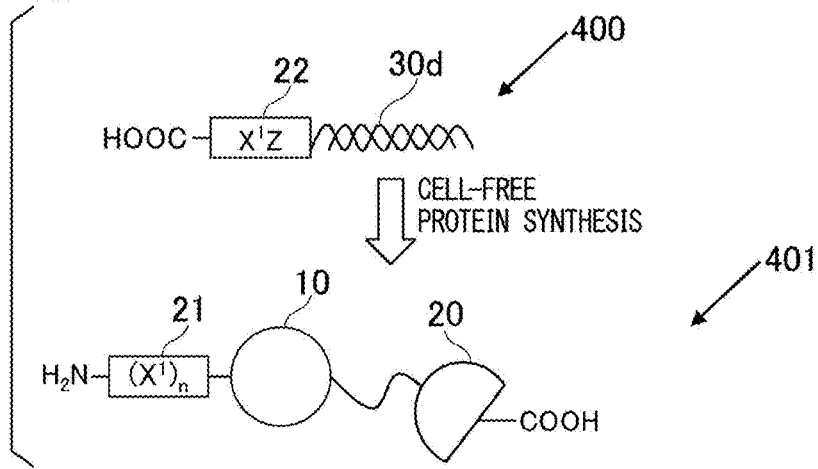
FIG. 4B is a schematic diagram showing an example of a step (B2) in the method for producing a peptide-nucleic acid complex according to the fourth embodiment of the present invention.

Next, a chimeric protein 401 is synthesized from the NS-added nucleic acid 400 using a cell-free protein synthesis system (FIG. 4B; step (B2)). The chimeric protein 401 contains a transpeptidase N-terminal substrate motif 21, a domain of a peptide 10, and a domain of a transpeptidase 20. In the chimeric protein 401, the transpeptidase N-terminal substrate motif 21 is located on the N-terminal side of the domain of the peptide 10. In the chimeric protein 401, the transpeptidase N-terminal substrate motif 21, the peptide 10, and the transpeptidase 20 are arranged in order from the N-terminal side to the C-terminal side.

Figure 4C:
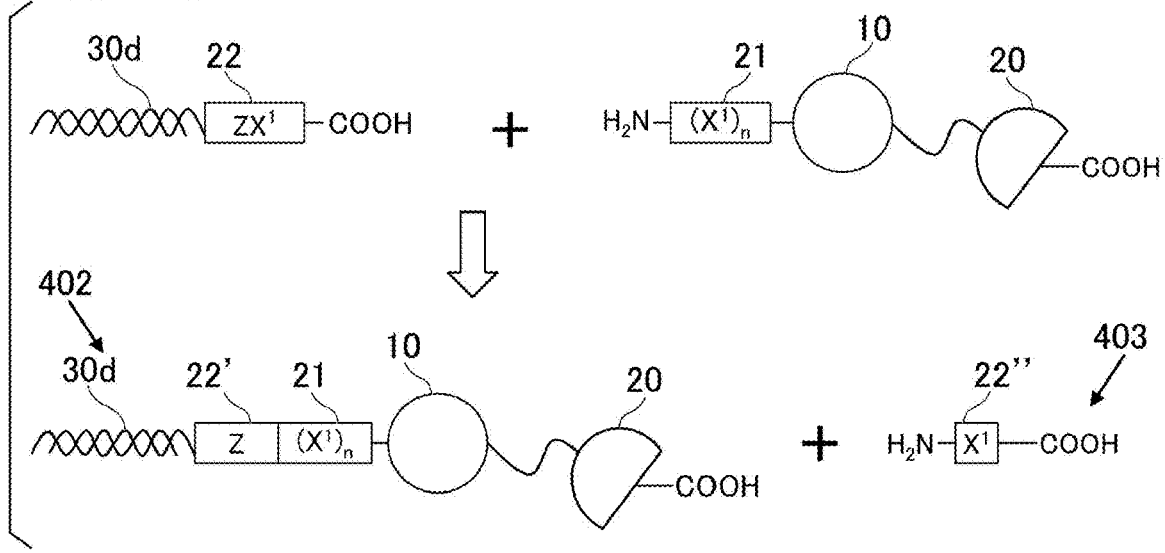
FIG. 4C is a schematic diagram showing an example of a step (C2) in the method for producing a peptide-nucleic acid complex according to the fourth embodiment of the present invention.

Next, the peptide-nucleic acid complex 402 is formed through a transpeptidation reaction by the domain of the transpeptidase 20 of the chimeric protein 401 (FIG. 4C; step (C2)). In this manner, a peptide-nucleic acid complex can be produced.

Hereinafter, each step of the producing method of this embodiment will be described.

[Step (A2)]

The step (A2) is a step of preparing a nucleic acid to which a transpeptidase recognition motif has been added, the nucleic acid containing a first coding sequence encoding the peptide, a second coding sequence encoding a transpeptidase, and a third coding sequence encoding a transpeptidase N-terminal substrate motif.

The step (A2) can be carried out in the same manner as the step (A1) of the first embodiment of the first aspect except that the TPR-added nucleic acid 400 is used instead of the NS-added nucleic acid 100.

A TPR-added nucleic acid is a nucleic acid to which a transpeptidase recognition motif has been added to any one of the 5' terminal and the 3' terminal. In the TPR-added nucleic acid 400 shown in FIG. 4A, the transpeptidase recognition motif 22 is added to the 5' terminal of a nucleic acid 30d. In FIG. 4A, the transpeptidase recognition motif 22 is exemplified as a peptide having an amino acid sequence of ZX$^1$. The description of ZX$^1$ is as described in the first embodiment of the first aspect. Further, in this embodiment, the bond between Z and X$^1$ may be an ester bond (Williamson D J et al., Nat Protoc. 2014 February; 9 (2): 253 to 262). Accordingly, in the TPR-added nucleic acid 400, the transpeptidase recognition motif 22 includes a motif in which Z and X$^1$ are linked by an ester bond. The same applies to a TPR-added nucleic acid 500 in the fifth embodiment that will be described later.

In a case where the transpeptidase is a buterase, the transpeptidase recognition motif 22 may be represented by X$^D$HV (X$^D$ is asparagine or aspartic acid; H is histidine; and V is valine).

The first coding sequence and the second coding sequence are the same as those described in the first embodiment of the first aspect.

The third coding sequence may be a sequence encoding the transpeptidase N-terminal substrate motif 21 and may be a sequence of a wild-type gene, a sequence of a modified gene, or a sequence having a silent mutation.

In the TPR-added nucleic acid 400, the third coding sequence, the first coding sequence, and the second coding sequence are arranged in order from the 5' side to the 3' side (see FIG. 4A). In addition, in the TPR-added nucleic acid 400, these sequences are arranged so that a chimeric protein, which is the chimeric protein 401 that contains a domain of the peptide 10 translated from the first coding sequence, a domain of the transpeptidase 20 translated from the second coding sequence, and the transpeptidase N-terminal substrate motif 21 translated from the third coding sequence and in which the transpeptidase N-terminal substrate motif 21 is located on the N-terminal side of the domain of peptide 10, can be expressed (see FIG. 4B). That is, the third coding sequence, the first coding sequence, and the second coding sequence are linked in-frame in order from the 5' side to the 3' side in one ORF with or without the interposition of any base sequence.

The TPR-added nucleic acid 400 may have another base sequence in addition to the first coding sequence, the second coding sequence, and the third coding sequence. Examples of the other base sequence include a regulatory sequence that regulates transcription and/or translation of an ORF containing the first coding sequence, the second coding sequence, and the third coding sequence. Examples of the regulatory sequence include the same sequences as those mentioned in the step (A1) of the first embodiment of the first aspect.

The TPR-added nucleic acid 400 may have a sequence which encodes any spacer between the first coding sequence and the third coding sequence or/and between the third coding sequence and the second coding sequence. For example, the TPR-added nucleic acid 400 may have a sequence which encodes any spacer between the first coding sequence and second coding sequence. In a case where a spacer is contained, the transpeptidase 20 is easily bonded to the transpeptidase recognition motif 22 in the chimeric protein 401 which has been expressed from the TPR-added nucleic acid 400.

Figure 6A:
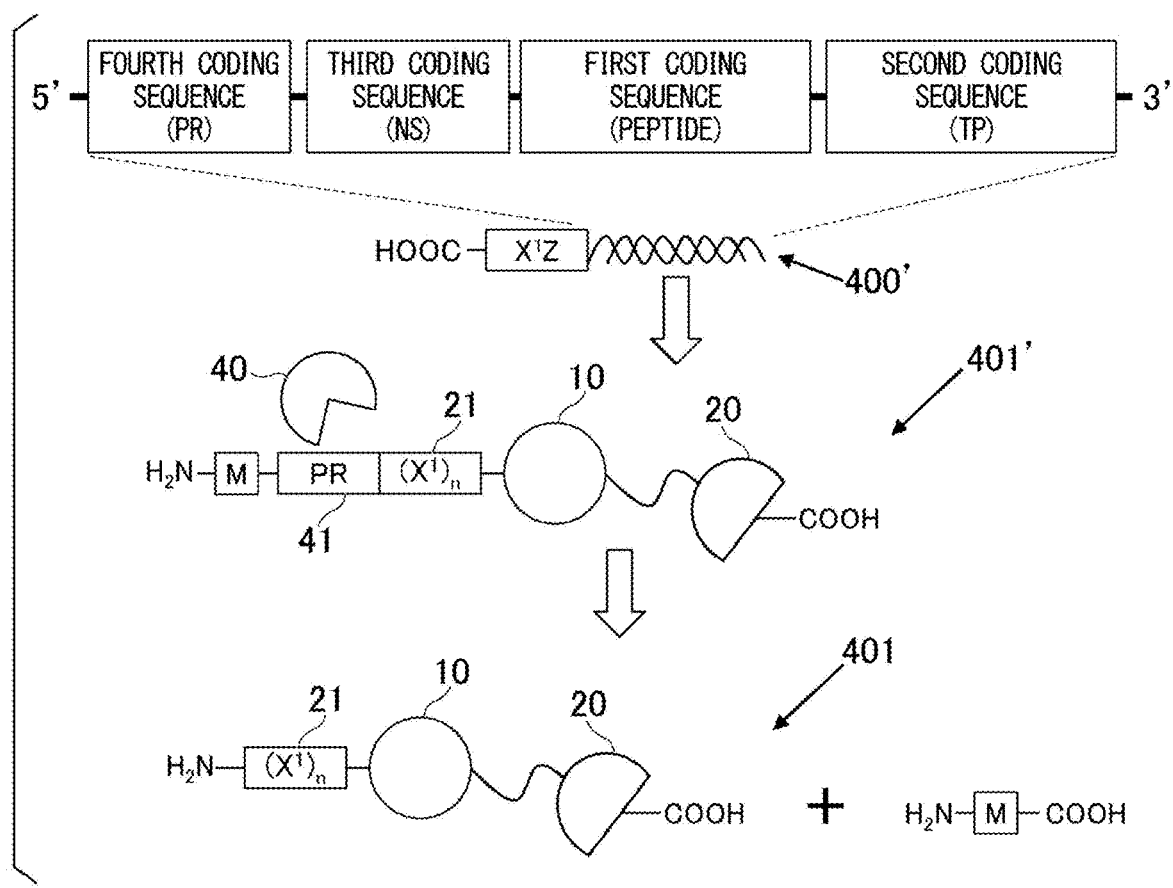
FIG. 6A is a schematic diagram showing an example of a step (D2) in the method for producing a peptide-nucleic acid complex according to the fourth embodiment of the present invention.

The TPR-added nucleic acid 400 may be a TPR-added nucleic acid 400' which contains a fourth coding sequence encoding a protease recognition motif 41, where the fourth coding sequence is adjacent to the 5' terminal of the third coding sequence (see FIG. 6A). As the protease recognition motif 41, a recognition motif for a protease having an activity of cleaving the bond between the protease recognition motif 41 and the transpeptidase N-terminal substrate motif 21 is used. For example, in a case where the transpeptidase N-terminal substrate motif 21 is a sequence represented by (G)$_n$ (n is an integer of 1 or more), a recognition motif (ENLYFQG (SEQ ID NO: 27)) for a TEV protease, a recognition motif (I(E/D)GR (SEQ ID NO: 28)) for Factor Xa protease, or the like can be used as the protease recognition motif 41.

In a case where the TPR-added nucleic acid 400 is the TPR-added nucleic acid 400' having the fourth coding sequence which is adjacent to the 5' terminal of the third coding sequence, the protease recognition motif 41 is arranged adjacent to the N-terminal of the transpeptidase N-terminal substrate motif 21 in a chimeric protein 401' expressed from the TPR-added nucleic acid 400' (see FIG. 6A). As a result, even in a case where an amino acid residue such as methionine (M) which is translated from the starting codon is present on the N-terminal side of the transpeptidase N-terminal substrate motif 21 in the chimeric protein 401', the transpeptidase N-terminal substrate motif 21 can be exposed at the N-terminal of the chimeric protein by the treatment with the protease 40 (see FIG. 6A).

The method for adding the transpeptidase recognition motif 22 to the nucleic acid 30d is not particularly limited, and the same method as the method exemplified as the method for adding the transpeptidase N-terminal substrate motif 21 to the nucleic acid 30a in the step (A1) of the first example of the first embodiment can be used.

The TPR-added nucleic acid 400 prepared in this step may be or may not be immobilized on a solid phase carrier; however, it is preferably immobilized on a solid phase carrier. Examples of the solid phase carrier are not particularly limited and include the same carriers as those exemplified in the step (A1) of the first embodiment of the first aspect. Examples of the method for immobilizing a nucleic acid on the solid phase carrier include the same methods as those exemplified in the step (A1) of the first example of the first aspect.

Also in the producing method of this embodiment, since one kind of TPR-added nucleic acid 400 per one bead is presented in the same manner as in the step (A1) of the first embodiment of the first aspect, the TPR-added nucleic acid 400 is preferably prepared by the emulsion PCR using a primer set in which at least one primer has been immobilized on a bead.

However, the method for presenting one kind of TPR-added nucleic acid 400 per one bead is not limited to the emulsion PCR. For example, a method in which one molecule of nucleic acid 30d and one bead are compartmentalized in one reaction chamber and a PCR reaction is carried out may be used.

Also in a case where the primer is not immobilized on the bead, one molecule of a template DNA may be compartmentalized in one emulsion, and then the emulsion PCR may be performed.

[Step (B2)]

The step (B2) is a step of synthesizing a chimeric protein containing a domain of the peptide, a domain of the transpeptidase, and the transpeptidase N-terminal substrate motif, from the nucleic acid to which the transpeptidase recognition motif has been added, using a cell-free protein synthesis system.

The step (B2) can be carried out in the same manner as in the step (B1) of the first embodiment of the first aspect except that the TPR-added nucleic acid 400 is used instead of the NS-added nucleic acid 100.

In this embodiment, the chimeric protein 401 is a protein that is transcribed and translated from the nucleic acid 30d. The chimeric protein 401 contains the transpeptidase N-terminal substrate motif 21, the domain of the peptide 10, and the domain of the transpeptidase 20. In the chimeric protein 401, the transpeptidase N-terminal substrate motif 21, the domain of the peptide 10, and the domain of the transpeptidase 20 are arranged in order from the N-terminal side to the C-terminal side (see FIG. 4B).

In a cell-free synthesis system, a protein having any amino acid at the N-terminal thereof can be synthesized by using a starting tRNA to which any amino acid is bonded. For example, a protein in which the N-terminal protein is glycine can be synthesized by using a starting tRNA to which glycine is bonded (for example, Goto Y and Suga H, J Am Chem Soc. 2009 Apr. 15; 131 (14): 5040 to 5041; PCT International Publication No. WO2007/058376).

[Step (C2)]

The step (C2) is a step of forming a peptide-nucleic acid complex through a transpeptidation reaction by the transpeptidase domain of the chimeric protein synthesized in the step (B2).

The step (C2) can be carried out in the same manner as the step (C1) of the first embodiment of the first aspect except that the TPR-added nucleic acid 400 is used instead of the NS-added nucleic acid 100 and the chimeric protein 401 is used instead of the chimeric protein 101.

In the step (B2), the chimeric protein 401 synthesized from the TPR-added nucleic acid 400 contains the domain of the transpeptidase 20 and the transpeptidase N-terminal substrate motif 21. On the other hand, the TPR-added nucleic acid 400 contains the transpeptidase recognition motif 22. As a result, the transpeptidase recognition motif 22 in the TPR-added nucleic acid 400 is recognized by the domain of the transpeptidase 20 and cleaved at a predetermined position in the motif. As a result, the transpeptidase recognition motif 22 is divided into the sequence 22' and the sequence 22", and the C-terminal of the sequence 22' is linked to a cysteine residue in the domain of the transpeptidase 20 by a thioester bond. As a result, a nucleic acid A containing the sequence 22' and the chimeric protein 401 are linked by a thioester bond. In addition, a transpeptidation reaction product 403 containing the sequence 22" is generated.

Next, the N-terminal of the transpeptidase N-terminal substrate motif 21 of the chimeric protein 401 is bonded to the C-terminal of the sequence 22' in the nucleic acid A. As a result, the peptide-nucleic acid complex 402 containing the peptide 10 and the nucleic acid 30d encoding the peptide is formed.

In a case where transpeptidase is a buterase, the transpeptidase recognition motif 22 may be represented by $X^D HV$ ($X^D$ is asparagine or aspartic acid; H is histidine; and V is valine). In a case where the transpeptidase is the buterase 1, the transpeptidase N-terminal substrate motif 21 may be represented by $X^E X^F$ ($X^E$ is any amino acid, and $X^F$ is leucine, isoleucine, valine, or cysteine).

In this case, first, the peptide bond between $X^D$ and H in the transpeptidase recognition motif 22 of the TPR-added nucleic acid 400 is cleaved by the transpeptidase activity of the domain of the transpeptidase 20 in the chimeric protein 101. As a result, the transpeptidase recognition motif 22 is divided into $X^D$ (corresponding to the above sequence 22') and HV (corresponding to the above sequence 22"). Next, a novel peptide bond is formed between the C-terminal amino acid residue ($X^D$) of the cleaved transpeptidase recognition motif 22 and the N-terminal amino acid sequence $X^E X^F$ of the transpeptidase N-terminal substrate motif 21 of the chimeric protein 401. As a result, the peptide-nucleic acid complex 102 and the transpeptidation reaction product 103 are generated.

The peptide-nucleic acid complex 402 obtained by this step has a structure in which a chimeric protein containing the transpeptidase 20 and the peptide 10 is bonded to a nucleic acid 30d via the TPR-NS sequence (see FIG. 4C).

[Other Steps]

The producing method of this embodiment may include other steps in addition to the above steps (A2) to (C2). The other steps are not particularly limited, and examples thereof include a step of recovering a nucleic acid, a chimeric protein, or a peptide-nucleic acid complex, a washing step, and a purification step. In a case where the nucleic acid 30d contains the fourth coding sequence encoding the protease recognition motif, it is preferable to include the following step (D2).

(Step (D2))

The step (D2) is a step of cleaving a bond between the protease recognition motif and the transpeptidase N-terminal substrate motif by using the above protease. The step (D2) is performed after the step (B2) and before the step (C2).

In a case where the nucleic acid 30d contains the fourth coding sequence encoding the protease recognition motif, where the fourth coding sequence is adjacent to the 5' terminal of the third coding sequence, the chimeric protein 401' expressed from the nucleic acid 30d contains the protease recognition motif 41 translated from the fourth coding sequence, where the protease recognition motif 41 is adjacent to the N-terminal side of the transpeptidase N-terminal substrate motif 21 translated from the third coding sequence (see FIG. 6A). As a result, in a case where the chimeric protein 401' is treated with the protease 40 having the activity of cleaving the peptide bond between the C-terminal amino acid residue of the protease recognition motif 41 and the N-terminal amino acid residue of the transpeptidase N-terminal substrate motif 21, the above peptide bond can be cleaved.

Accordingly, even in a case where an amino acid residue such as methionine (M) which is translated from the starting codon is present on the N-terminal side of the transpeptidase N-terminal substrate motif 21 in the chimeric protein 401', the chimeric protein 401 in which the transpeptidase N-terminal substrate motif 21 is exposed at the N-terminal can be obtained by the treatment with the protease 40 (see FIG. 6A).

The protease 40 may be added externally in the step (D2), or a coding sequence encoding the protease 40 may be incorporated in the nucleic acid 30d and expressed in the step (B2) as a protein separated from the chimeric protein 401'.

According to the producing method of this embodiment, a peptide-nucleic acid complex can be produced without requiring complicated work such as the preparation of a linker. The peptide-nucleic acid complex obtained by the producing method of this embodiment can be suitably used for screening a peptide array for a peptide having a desired function, and the nucleic acid encoding the peptide obtained by screening can be easily identified.

Fifth Embodiment

Figure 5A:
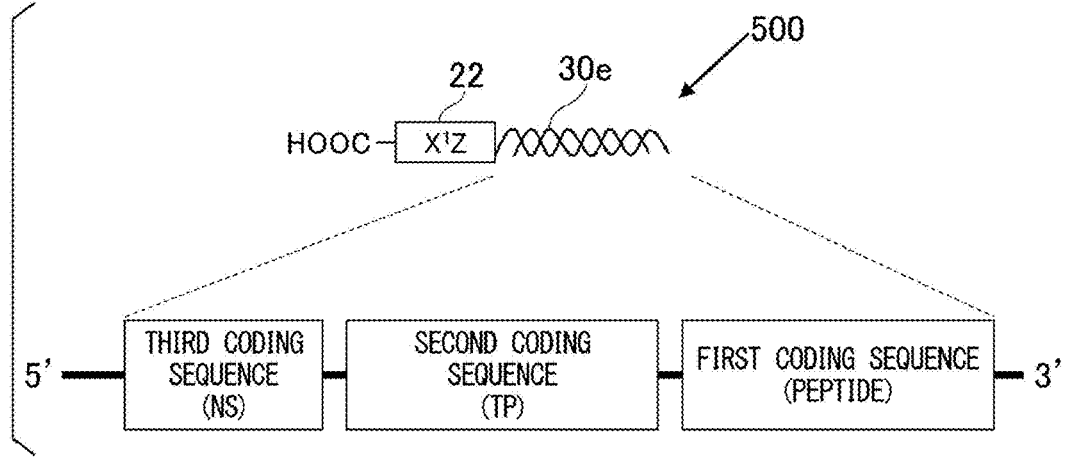
FIG. 5A is a schematic diagram showing an example of a step (A2) in a method for producing a peptide-nucleic acid complex according to the fifth embodiment of the present invention. An example of a nucleic acid to which a transpeptidase recognition motif has been added is shown.

An outline of the fifth embodiment of the producing method according to this aspect will be described with reference to FIGS. 5A to 5C.

In this embodiment, as the nucleic acid to which the transpeptidase recognition motif 22 has been added, a nucleic acid (hereinafter, may be referred to as an "TPR-added nucleic acid 500") obtained by attaching the transpeptidase recognition motif 22 to the nucleic acid 30e in which the third coding sequence encoding the transpeptidase N-terminal substrate motif 21, the second coding sequence encoding a transpeptidase, and a first coding sequence coding a peptide are arranged in order from the 5' side to the 3' side is used (see FIG. 5A).

The TPR-added nucleic acid 500 may have a sequence which encodes any spacer between the third coding sequence and the second coding sequence or/and between the second coding sequence and the first coding sequence. For example, the TPR-added nucleic acid 500 may have a sequence which encodes any spacer between the third coding sequence and second coding sequence. In a case where a spacer is contained, the transpeptidase 20 is easily bonded to the transpeptidase recognition motif 22 in the chimeric protein 501 which has been expressed from the TPR-added nucleic acid 500.

The producing method of this embodiment can be carried out in the same manner as in the fourth embodiment except that the TPR-added nucleic acid 500 is used instead of the TPR-added nucleic acid 400 of the fourth embodiment.

Figure 5B:
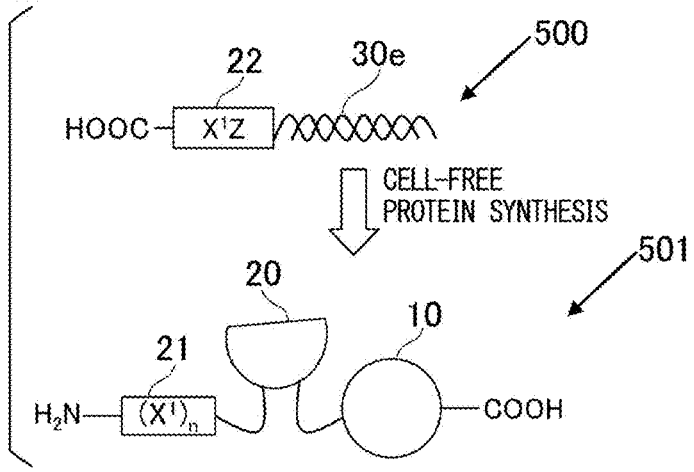
FIG. 5B is a schematic diagram showing an example of a step (B2) in the method for producing a peptide-nucleic acid complex according to the fifth embodiment of the present invention.

The chimeric protein 501 synthesized from the TPR-added nucleic acid 500 using the cell-free protein synthesis system has a configuration in which the transpeptidase N-terminal substrate motif 21, the domain of the transpeptidase 20, and the domain of the peptide 10 are arranged in order from the N-terminal side to the C-terminal side (see FIG. 5B).

A peptide-nucleic acid complex 502 and a transpeptidation reaction product 503 are generated from the TPR-added nucleic acid 500 and the chimeric protein 501 through the transpeptidation reaction by transpeptidase 20 in the chimeric protein 501.

Figure 5C:
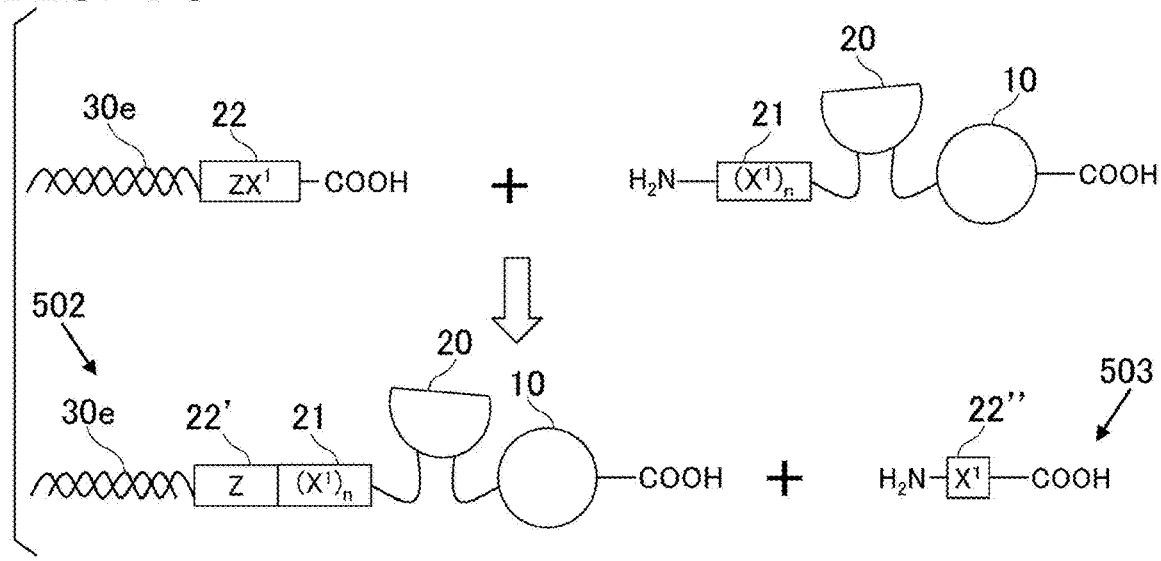
FIG. 5C is a schematic diagram showing an example of a step (C2) in the method for producing a peptide-nucleic acid complex according to the fifth embodiment of the present invention.

The peptide-nucleic acid complex 502 has a structure in which a chimeric protein containing the peptide 10 and the transpeptidase 20 is bonded to a nucleic acid 30e via the TPR-NS sequence (see FIG. 5C).

Figure 6B:
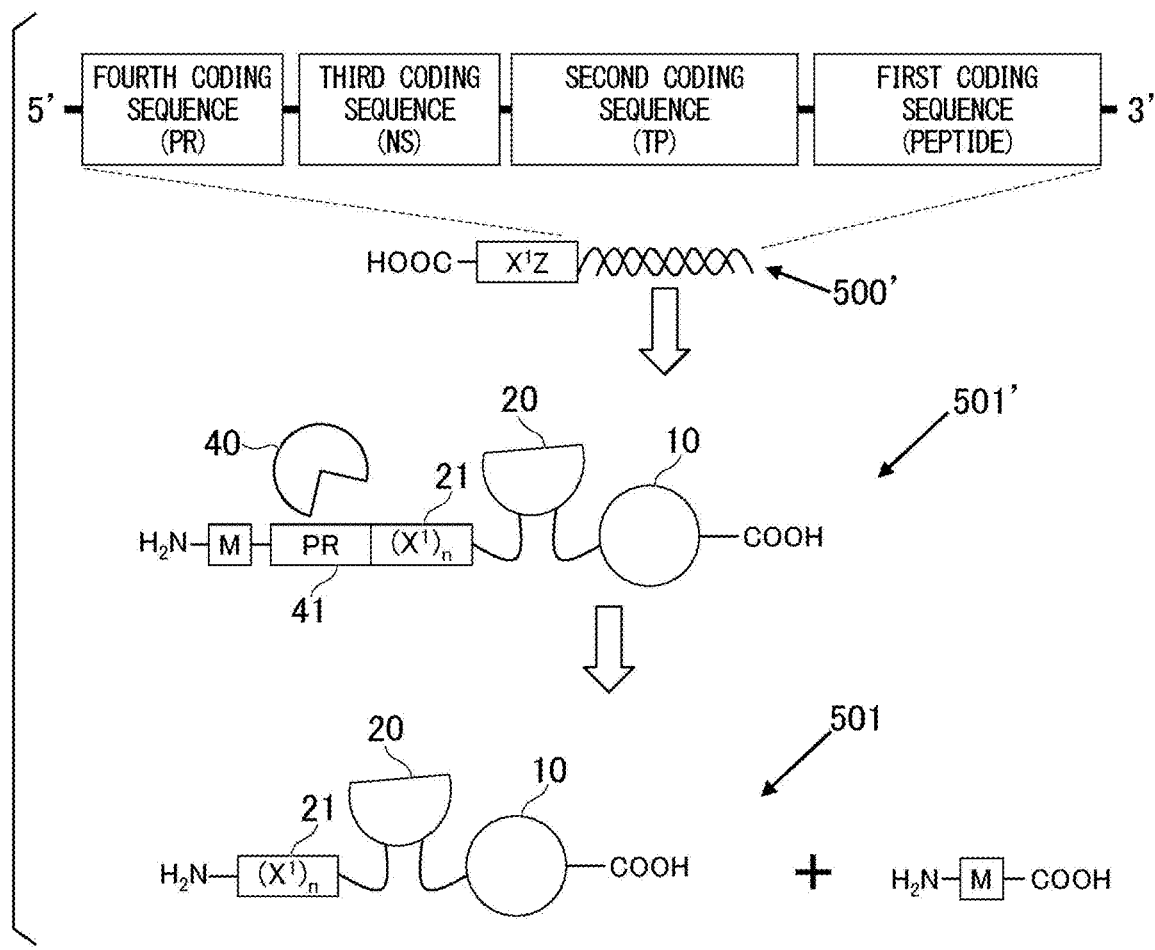
FIG. 6B is a schematic diagram showing an example of a step (D2) in the method for producing a peptide-nucleic acid complex according to the fifth embodiment of the present invention.

Similar to the fourth embodiment, the producing method of this embodiment may further include the step (D2) after the step (B2) and before the step (C2). That is, the nucleic acid 30e may contain a fourth coding sequence encoding a protease recognition motif 41, where the fourth coding sequence is adjacent to the 5' terminal of the third coding sequence (see FIG. 6B). In this case, in a chimeric protein 501' expressed from the TPR-added nucleic acid 500', the protease recognition motif 41 is arranged adjacent to the N-terminal of the transpeptidase N-terminal substrate motif 21 (see FIG. 6B). As a result, even in a case where an amino acid residue such as methionine (M) which is translated from the starting codon is present on the N-terminal side of the transpeptidase N-terminal substrate motif 21, the chimeric protein 501 in which the transpeptidase N-terminal substrate motif 21 is exposed at the N-terminal can be obtained by treating the protease 40 on the chimeric protein 501' (see FIG. 6B).

The fact that the third coding sequence is located on the 5' side of the first coding sequence and the second coding sequence is common to the nucleic acids 30d and 30e according to the fourth and fifth embodiments according to the second aspect. Further, the fact that the transpeptidase N-terminal substrate motif 21 is located on the N-terminal side of the peptide 10 and the transpeptidase 20 is common to the chimeric proteins 401 and 501, which are respectively expressed from the nucleic acids 30d and 30e.

<Peptide-Nucleic Acid Complex>

In one embodiment, the present invention provides a peptide-nucleic acid complex containing (a) a peptide; (b) a nucleic acid containing a coding sequence of the peptide; and (c) a sequence generated by bonding a transpeptidase recognition motif and a transpeptidase N-terminal substrate motif through a transpeptidation reaction by the transpeptidase, the sequence of (c) being located between the peptide of (a) and the nucleic acid of (b). The peptide-nucleic acid complex can contain a transpeptidase on the N-terminal side or C-terminal side of the peptide of (a) or between the sequence of (c) and the peptide of (a).

This will be described in more detail.

[(a) Peptide]

The peptide is not particularly limited and may be any peptide. The peptide is a peptide encoded by the nucleic acid of (b). Examples of the peptide include the same peptides as those exemplified in the first embodiment of the first aspect of "<Method for producing peptide-nucleic acid complex>" described above. The peptide of (a) may be a domain of a peptide contained in a chimeric protein. The chimeric protein may contain domains other than the peptide. The chimeric protein may contain, for example, a domain of a transpeptidase. Examples of the chimeric protein include a chimeric protein having a configuration in which a domain of a peptide and a domain of a transpeptidase are arranged in order from the N-terminal side to the C-terminal side; and a chimeric protein having a configuration in which a domain of a transpeptidase and a domain of a peptide are arranged in order from the N-terminal side to the C-terminal side. The transpeptidase is preferably a sortase or a buterase, more preferably the sortase A or the buterase 1, and still more preferably the sortase A.

[(b) Nucleic Acid]

The nucleic acid is a nucleic acid encoding the above peptide of (a). The nucleic acid may be a wild-type gene, a modified gene, or a nucleic acid having a silent mutation as long as the nucleic acid encodes the peptide of (a). Further, the nucleic acid may be derived from a mixture of a plurality of kinds of DNA such as a DNA library, as exemplified in "<Method for producing peptide-nucleic acid complex>" described above.

The nucleic acid may contain other sequences in addition to the peptide coding sequence. Examples of the other sequences include a sequence encoding a transpeptidase, a sequence encoding a transpeptidase N-terminal substrate motif, and a sequence encoding a transpeptidase recognition motif. Examples of the nucleic acid include a nucleic acid (1) having a configuration in which the a first coding sequence encoding any peptide, a third coding sequence encoding a transpeptidase recognition motif, and a second coding sequence encoding the transpeptidase are arranged in order from the 5' side to the 3' side; a nucleic acid (2) having a configuration in which the second coding sequence, the first coding sequence, and the third coding sequence are arranged in order from the 5' side to the 3' side; and a nucleic acid (3) having a configuration in which the first coding sequence, the second coding sequence, and the third coding sequence are arranged in order from the 5' side to the 3' side.

In addition, examples of the nucleic acid include a nucleic acid (4) having a configuration in which the a third coding sequence encoding a transpeptidase N-terminal substrate motif, a first coding sequence encoding any peptide, and a second coding sequence encoding the transpeptidase are arranged in order from the 5' side to the 3' side; and a nucleic acid (5) having a configuration in which the third coding sequence, the second coding sequence, and the first coding sequence are arranged in order from the 5' side to the 3' side. In these cases, the nucleic acid may further include a fourth coding sequence encoding a protease recognition motif, which is adjacent to the 5' terminal of the third coding sequence encoding the transpeptidase N-terminal substrate motif.

In a case where the nucleic acid encodes a sortase as the transpeptidase, the nucleic acid may be any one of the nucleic acids (1) to (5) exemplified above; however, it is preferably the nucleic acid (1). In a case where the nucleic acid encodes a buterase as the transpeptidase, the nucleic acids (2) to (5) are preferable among the nucleic acids exemplified above.

The nucleic acid may further contain other sequences. Examples of the other sequences include the same sequences as those mentioned in "<Method for producing peptide-nucleic acid complex>" described above. For example, the nucleic acid may contain a sequence encoding any spacer between each of the coding sequences. Further, a regulatory sequence such as a promoter sequence that regulates the expression of the coding sequence may be included.

Specific examples of the nucleic acid include nucleic acids 30a, 30b, 30c, 30d, and 30e, which are exemplified in "<Method for producing peptide-nucleic acid complex>" described above (see FIGS. 1 to 5).

[(c) TPR-Ns Sequence]

The sequence of (c) is a sequence (a TPR-NS sequence) generated by bonding a transpeptidase recognition motif and a transpeptidase N-terminal substrate motif and is the same as the sequence described above in "<Method for producing peptide-nucleic acid complex>". The transpeptidase is preferably a sortase or a buterase, more preferably the sortase A or the buterase 1, and still more preferably the sortase A. The TPR-NS sequence can be appropriately selected depending on the kind of transpeptidase. For example, in a case where the transpeptidase is a sortase, preferred specific examples of the TPR-NS sequence include $LPXT(G)_n$ (n is an integer of 1 or more). n is preferably 1 to 10, more preferably 1 to 8, and still more preferably 1 to 6 or 1 to 5. Alternatively, the same sequence as the sortase recognition motif described above can be mentioned.

In a case where the transpeptidase is a buterase, examples of the TPR-NS sequence include a sequence represented by $X^D X^E X^F$ ($X^D$ is asparagine or aspartic acid; $X^E$ is any amino acid; $X^F$ is leucine, isoleucine, valine, or cysteine).

The peptide-nucleic acid complex of this embodiment is characterized by the fact that the sequence of (c) is located between the peptide of (a) and the nucleic acid of (b). The peptide-nucleic acid complex of this embodiment can be produced by the method described above in "<Method for producing peptide-nucleic acid complex>". Specific examples of the peptide-nucleic acid complex of this embodiment include the peptide-nucleic acid complexes 102, 202, 302, 402, and 502, which are exemplified in "<Method for producing peptide-nucleic acid complex>" described above (see FIGS. 1 to 5).

In the peptide-nucleic acid complex of this embodiment, since the peptide and the nucleic acid encoding the peptide form a complex, the nucleic acid encoding the peptide can be easily acquired after identifying the peptide having a desired function.

<Solid Phase Carrier on which Peptide-Nucleic Acid Complex has been immobilized>

In one embodiment, the present invention provides a solid phase carrier on which the peptide-nucleic acid complex of the embodiment has been immobilized.

The solid phase carrier is not particularly limited, and examples thereof include the same carriers as those mentioned in "<Method for producing peptide-nucleic acid complex>" described above. Among them, the solid phase carrier is preferably a bead and more preferably a magnetic bead. In a case where the solid phase carrier is a bead, it is preferable that one kind of peptide-nucleic acid complex be immobilized on one bead.

The method for immobilizing the peptide-nucleic acid complex on the solid phase carrier is not particularly limited, and a known method can be used. In the peptide-nucleic acid complex, it is preferable that the 5' terminal or 3' terminal of the nucleic acid be immobilized on the solid phase carrier. Examples of the immobilization method include the same methods as those mentioned in "<Method for producing peptide-nucleic acid complex>" described above. Among them, a method of utilizing an avidin-biotin binding is suitably used.

Example of Use

The solid phase carrier of this embodiment may be arranged in a reaction chamber for use as will be described later, or the solid phase carrier itself may be used as a peptide array. Hereinafter, specific examples of identifying a nucleic acid encoding a desired peptide by using the peptide-nucleic acid complex of this embodiment will be described; however, the present invention is not limited thereto.

Screening Example for Peptide Having High Bonding Affinity to Specific Substance The peptide-nucleic acid complex is brought into contact with a specific substance to which a labeling substance has been bonded. For example, the specific substance to which a labeling substance has been bonded is added to a solution containing the peptide-nucleic acid complex and stirred. As the labeling substance, a known substance can be used without particular limitation, and for example, the following substances can be used: a fluorescent dye such as fluorescein, rhodamine, Texas Red, or Oregon Green; an enzyme such as horseradish peroxidase, microperoxidase, alkaline phosphatase, or β-D-galactosidase; a chemical or bioluminescent compound such as luminol or an Acridine dye; and a radioisotope such as $^{32}P$, $^{131}I$, or $^{125}I$.

Next, the binding between the peptide and the specific substance is detected based on the labeling substance, and the peptide-nucleic acid complex containing the peptide having a high binding affinity is recovered. In a case where the solid phase carrier is a bead, flow cytometry can be suitably used for the detection of the labeling substance and the recovery of the peptide-nucleic acid complex.

Screening Example for Peptide Having Specific Enzyme Activity

An emulsion containing a peptide-nucleic acid complex immobilized on a bead as a solid phase carrier and containing an enzyme substrate is prepared. The emulsion can be, for example, a water-in-oil-in-water (W/O/W) type emulsion having an internal aqueous phase. The size of the emulsion particle is adjusted so that one emulsion particle encloses one or less beads on average. Next, an enzymatic reaction is carried out in the emulsion, an emulsion in which the enzymatic reaction is observed is identified, and then the peptide-nucleic acid complex enclosed in the emulsion is recovered. In a case where a reaction system in which fluorescence is generated through the enzymatic reaction is adopted, flow cytometry can be suitably used for the detection of the enzymatic reaction and recovery of the peptide-nucleic acid complex.

<Peptide Array>

In one embodiment, the present invention provides a peptide array which includes a reaction chamber containing the solid phase carrier of the above embodiment.

In this embodiment, for example, the solid phase carrier may be a bead, or a bead on which a peptide-nucleic acid complex has been immobilized may be arranged in a reaction chamber. Alternatively, the solid phase carrier may be the wall surface of the reaction chamber. It is preferable that one kind of peptide-nucleic acid complex be arranged in each reaction chamber. For example, in a case where the solid phase carrier is a bead, it is preferable to arrange one bead on which one kind of peptide-nucleic acid complex has been immobilized in one reaction chamber.

The reaction chamber in which the bead is arranged may be, for example, a substrate for bead arrangement such as a micro well plate having a reaction chamber for bead arrangement. In a case where the bead is a magnetic bead, it is preferable that the substrate for bead arrangement be a substrate for magnetic bead arrangement, and it is more preferable that a magnetic substance plate be disposed under a substrate material used for the substrate for magnetic bead arrangement. In a case where the substrate for magnetic bead arrangement which has the above structure is used, the magnetic bead can be easily and highly precisely arranged in the reaction chamber. Specifically, a magnet is disposed under the substrate for bead arrangement, and a dispersion solution in which magnetic beads having DNA fixed on the substrate thereof are dispersed is added dropwise. Due to the action of the magnetic force of the magnetic bead and the thin magnetic substance film, the magnetic bead is attracted into the reaction chamber and thus is easily arranged. Further, in a case where the magnet is appropriately moved in the direction parallel to the substrate, the magnetic beads are dispersed and the filling rate in the reaction chamber is improved. The strength of the magnetic field applied to the substrate for bead arrangement by the magnet is preferably 100 to 10,000 gausses in terms of obtaining a desired effect.

Further, since the magnetization of the magnetic substance plate is retained even after the magnet is removed, the magnetic beads can be continuously maintained in a stable arrangement.

As a material for such a magnetic substance material, a metal such as nickel, a nickel alloy, iron, or an iron alloy can be suitably used.

From the viewpoint of arranging one bead per one reaction chamber, it is preferable that the diameter of the reaction chamber be substantially the same as the diameter of the bead. However, since the filling rate of the bead in the micro reaction chamber depends on the diameter of the micro reaction chamber, the filling rate is higher in a case where the diameter of the reaction chamber is slightly larger than the diameter of the bead. Further, the diameter of the reaction chamber is preferably 1 to 2 times the diameter of the bead. Further, from the viewpoint of arranging one bead per one reaction chamber, the depth of the reaction chamber is preferably 1 to 2 times the diameter of the bead. The reaction chamber is preferably hydrophilized. For example, in a case where the reaction chamber is hydrophilized by being irradiated with oxygen plasma or the like, the inside of the reaction chamber becomes easily filled with a solution in which the beads are dispersed, and thus the filling rate is improved.

The peptide array of this embodiment can be suitably used for identifying a peptide having a desired function and isolating the nucleic acid encoding the peptide. The identification of a peptide having a desired function can be performed by carrying out a desired reaction in reaction chambers and identifying a reaction chamber showing a desired reaction result. After identifying the reaction chamber, the nucleic acid encoding the peptide having a desired function can be acquired by recovering the peptide-nucleic acid complex from the reaction chamber.

<Nucleic Acid>

<<First Aspect>>

In one embodiment, the present invention provides a nucleic acid to which a transpeptidase N-terminal substrate motif has been added, the nucleic acid containing a first coding sequence encoding a peptide, a second coding sequence encoding a transpeptidase, and a third coding sequence encoding a transpeptidase recognition motif.

The nucleic acid of this embodiment is a nucleic acid to which a transpeptidase N-terminal substrate motif has been added, the nucleic acid containing a first coding sequence encoding a peptide; a second coding sequence encoding the transpeptidase; and a third coding sequence encoding a transpeptidase recognition motif. These coding sequences are the same as those described above in "<Method for producing peptide-nucleic acid complex>".

The nucleic acid of this embodiment may further contain other sequences. Examples of the other sequences include the same sequences as those mentioned in "<Method for producing peptide-nucleic acid complex>" described above. For example, the nucleic acid may contain a sequence encoding any spacer between each of the coding sequences. Further, a regulatory sequence such as a promoter sequence that regulates the expression of the coding sequence may be included.

In the nucleic acid of this embodiment, a chimeric protein which contains a peptide domain translated from the first coding sequence and a transpeptidase recognition motif translated from the third coding sequence and in which the transpeptidase recognition motif is located on the C-terminal side of the peptide domain can be expressed. That is, the first coding sequence and the third coding sequence are arranged in the same ORF, and the third coding sequence is arranged on the 3' side of the first coding sequence.

The second coding sequence may be or may not be arranged in the same ORF as the first coding sequence and the third coding sequence; however, it is preferably arranged in the same ORF. That is, in the nucleic acid of this embodiment, it is preferable that a chimeric protein containing a peptide domain translated from the first coding sequence, a transpeptidase domain translated from the second coding sequence, and a transpeptidase recognition motif translated from the third coding sequence can be expressed.

In a case where the second coding sequence is not arranged in the same ORF as the first coding sequence and the third coding sequence, it is preferable that each ORF have regulatory sequences that regulate transcription and translation.

Examples of the nucleic acid of this embodiment include the following nucleic acids (1) to (4) to which a transpeptidase N-terminal substrate motif has been added:

the nucleic acid (1) having a configuration in which the first coding sequence, the third coding sequence, and the second coding sequence are arranged in order from the 5' side to the 3' side;

the nucleic acid (2) having a configuration in which the second coding sequence, the first coding sequence, and the third coding sequence are arranged in order from the 5' side to the 3' side; and the nucleic acid (3) having a configuration in which the first coding sequence, the second coding sequence, and the third coding sequence are arranged in order from the 5' side to the 3' side.

In a case where the nucleic acid encodes a sortase as the transpeptidase, the nucleic acid may be any one of the nucleic acids (1) to (3) exemplified above; however, it is preferably the nucleic acid (1). In a case where the nucleic acid encodes a buterase as the transpeptidase, the nucleic acid (2) or the nucleic acid (3) is preferable among the nucleic acids exemplified above.

Suitable specific examples of the nucleic acid of this embodiment include the NS-added nucleic acid 100, the NS-added nucleic acid 200, and the NS-added nucleic acid 300, which are exemplified in "<Method for producing peptide-nucleic acid complex>" described above.

<<Second Aspect>>

In one embodiment, the present invention provides a nucleic acid to which a transpeptidase recognition motif has been added, the nucleic acid containing a first coding sequence encoding a peptide, a second coding sequence encoding a transpeptidase, and a third coding sequence encoding a transpeptidase N-terminal substrate motif.

The nucleic acid of this embodiment is a nucleic acid to which a transpeptidase recognition motif has been added, which contains a first coding sequence encoding a peptide; a second coding sequence encoding the transpeptidase; and a third coding sequence encoding a transpeptidase N-terminal substrate motif. These coding sequences are the same as those described above in "<Method for producing peptide-nucleic acid complex>".

The nucleic acid of this embodiment may further contain other sequences. Examples of the other sequences include the same sequences as those mentioned in "<Method for producing peptide-nucleic acid complex>" described above. For example, the nucleic acid may contain a sequence encoding any spacer between each of the coding sequences. Further, a regulatory sequence such as a promoter sequence that regulates the expression of the coding sequence may be included.

In the nucleic acid of this embodiment, a chimeric protein which contains a peptide domain translated from the first coding sequence and a transpeptidase N-terminal substrate motif translated from the third coding sequence and in which the transpeptidase N-terminal substrate motif is located on the N-terminal side of the peptide domain can be expressed. That is, the first coding sequence and the third coding sequence are arranged in the same ORF, and the third coding sequence is arranged on the 5' side of the first coding sequence.

The second coding sequence may be or may not be arranged in the same ORF as the first coding sequence and the third coding sequence; however, it is preferably arranged in the same ORF. That is, in the nucleic acid of this embodiment, it is preferable that a chimeric protein containing a peptide domain translated from the first coding sequence, a transpeptidase domain translated from the second coding sequence, and a transpeptidase N-terminal substrate motif translated from the third coding sequence can be expressed. In the chimeric protein, the domain of the transpeptidase is preferably located on the C-terminal side of the transpeptidase N-terminal substrate motif.

In a case where the second coding sequence is not arranged in the same ORF as the first coding sequence and the third coding sequence, it is preferable that each ORF have regulatory sequences that regulate transcription and translation.

Examples of the nucleic acid of this embodiment include the following nucleic acids (4) and (5) to which a transpeptidase recognition motif has been added:

the nucleic acid (4) having a configuration in which the third coding sequence, the first coding sequence, and the second coding sequence are arranged in order from the 5' side to the 3' side, and the nucleic acid (5) having a configuration in which the third coding sequence, the second coding sequence, and the first coding sequence are arranged in order from the 5' side to the 3' side.

In a case where the nucleic acid encodes a sortase or a buterase as the transpeptidase, the nucleic acid may be any one of the nucleic acid (4) and the nucleic acid (5) exemplified above.

The nucleic acid of this embodiment may further contain a fourth coding sequence encoding a protease recognition motif, where the fourth coding sequence is adjacent to the 5' terminal of the third coding sequence. In this case, in the chimeric protein, the protease recognition motif translated from the fourth coding sequence is adjacent to the N-terminal side of the transpeptidase N-terminal substrate motif. As the protease recognition motif, a recognition motif for a protease having an activity of cleaving the bond between the protease recognition motif and the transpeptidase N-terminal substrate motif can be used.

Suitable specific examples of the nucleic acid of this embodiment include the TPR-added nucleic acid 400, the TPR-added nucleic acid 400', the TPR-added nucleic acid 500, and the TPR-added nucleic acid 500', which are exemplified in "<Method for producing peptide-nucleic acid complex>" described above.

In the above embodiment, the nucleic acid to which the transpeptidase N-terminal substrate motif has been added or the nucleic acid to which the transpeptidase recognition motif has been added may be immobilized on a solid phase carrier. As a result, in one embodiment, the present invention also provides a solid phase carrier on which the nucleic acid of the above-described embodiment has been immobilized.

The nucleic acid of this embodiment or the solid phase carrier on which the above-described nucleic acid has been immobilized can be suitably used for producing a peptide-nucleic acid complex.

<Kit>

<<First Aspect>>

In one embodiment, the present invention provides a kit for preparing a peptide-nucleic acid complex, where the kit contains the following (a) to (d);
(a) a nucleic acid which contains a first coding sequence encoding any peptide or a cloning site into which a nucleic acid fragment containing the first coding sequence can be inserted, a second coding sequence encoding a transpeptidase, and a third coding sequence encoding a transpeptidase recognition motif,
(b) a primer set with which a region in the nucleic acid of (a), the region of the nucleic acid including the first coding sequence or the cloning site, the second coding sequence, and the third coding sequence, can be amplified and in which a transpeptidase N-terminal substrate motif is added to any one of a forward primer or a reverse primer,
(c) a nucleic acid amplification reagent, and
(d) a cell-free protein synthesis reaction solution.

((a) Nucleic Acid)

The nucleic acid of (a) is a nucleic acid which contains a first coding sequence encoding any peptide or a cloning site into which a nucleic acid fragment containing the first coding sequence can be inserted, a second coding sequence encoding a transpeptidase, and a third coding sequence encoding a transpeptidase recognition motif. These coding sequences are the same as those described above in "<Method for producing peptide-nucleic acid complex>".

The cloning site into which the nucleic acid fragment containing the first coding sequence can be inserted is not particularly limited and may be any restriction enzyme site. In a case where the nucleic acid fragment containing the first coding sequence is inserted into the above cloning site, the cloning site is arranged so that a chimeric protein, which is the protein that contains a domain of the peptide translated from the first coding sequence and a transpeptidase recognition motif, the recognition motif being translated from the third coding sequence, and in which the transpeptidase recognition motif is located on the C-terminal side of the domain of the peptide, can be expressed. That is, the cloning site and the third coding sequence are arranged in the same ORF, and the cloning site is arranged on the 5' side of the third coding sequence.

The nucleic acid of (a) may further contain other sequences. Examples of the other sequences include the same sequences as those mentioned in "<Method for producing peptide-nucleic acid complex>" described above. For example, the nucleic acid of (a) may contain a sequence encoding any spacer between each of the coding sequences. Further, a regulatory sequence such as a promoter sequence that regulates the expression of the coding sequence may be included.

Examples of the nucleic acid of (a) include a nucleic acid having a configuration in which the first coding sequence or the cloning site, the third coding sequence, and the second coding sequence are arranged in order from the 5' side to the 3' side; a nucleic acid having a configuration in which the second coding sequence, the first coding sequence, and the third coding sequence are arranged in order from the 5' side to the 3' side; and a nucleic acid having a configuration in which the first coding sequence or the cloning site, the second coding sequence, and the third coding sequence are arranged in order from the 5' side to the 3' side.

Preferred specific examples of the nucleic acid of (a) include the nucleic acids 30*a*, 30*b*, and 30*c*, which are exemplified in "<Method for producing peptide-nucleic acid complex>" described above, and a nucleic acid obtained by substituting the first coding sequence in any one of the nucleic acids 30*a*, 30*b*, and 30*c* with a cloning site.

The nucleic acid of (a) may be a plasmid. For example, a plasmid (a pBI-based plasmid, a pPZP-based plasmid, a pSMA-based plasmid, a pUC-based, a pBR-based plasmid, a pBluescript-based plasmid, or the like) derived from *Escherichia coli*, a plasmid (pUB110, pTP5, or the like) derived from *Bacillus subtilis*, a plasmid (Yep13, Yep24, YCp50, or the like) derived from yeast, or the like can be suitably used.

((b) Primer Set)

The primer set of (b) is a primer set capable of amplifying a region (hereinafter may be referred to as a "coding sequence region") containing the first coding sequence or the cloning site, the second coding sequence, and the third coding sequence in the nucleic acid of (a). The transpeptidase N-terminal substrate motif is added to any one of a forward primer or a reverse primer of the primer.

It is preferable that the primer set of (b) be capable of amplifying a coding sequence region in the nucleic acid of (a) and a region including a regulatory sequence that regulates transcription and/or translation of the corresponding coding sequence. A primer set capable of amplifying the above region can be designed based on a known method. The transpeptidase N-terminal substrate motif can be added to the primer in the same manner as in the method described above in "<Method for producing peptide-nucleic acid complex>".

In the primer set of (b) of the kit of this embodiment, any one of the forward primer or the reverse primer may be immobilized on a solid phase carrier. In this case, the primer set of (b) may be any of the following (i) to (iv);
(i) a set of a forward primer having a 5' terminal to which a transpeptidase N-terminal substrate motif has been added and a reverse primer having a 5' terminal which has been immobilized on a solid phase carrier,
(ii) a set of a forward primer having a 5' terminal to which a transpeptidase N-terminal substrate motif has been added and a reverse primer having a 5' terminal to which a substance having a binding affinity to a solid phase carrier has been added,
(iii) a set of a forward primer having a 5' terminal which has been immobilized on a solid phase carrier and a reverse primer having a 5' terminal to which a transpeptidase N-terminal substrate motif has been added, and
(iv) a set of a forward primer having a 5' terminal to which a substance having a binding affinity to a solid phase carrier has been added and a reverse primer having a 5' terminal to which a transpeptidase N-terminal substrate motif has been added.

Regarding the above (i) and (iii), examples of the method for producing immobilizing the primer on a solid phase carrier include the method mentioned in "<Method for producing peptide-nucleic acid complex>" described above. Regarding the above (ii) and (iv), the substance having a binding affinity to a solid phase carrier is not particularly limited and can be appropriately selected depending on the kind of the solid phase carrier. For example, in a case where an avidin-biotin binding is used, the solid phase carrier may be modified with streptavidin, and biotin may be bonded to the primer. Further, the primer may be modified with a functional group such as an amino group, a formyl group or an SH group, and the solid phase carrier may be subjected to a surface treatment with a silane coupling agent having an amino group, a formyl group, an epoxy group, or the like.

((c) Nucleic Acid Amplification Reagent)

The nucleic acid amplification reagent of (c) is a reagent used for a nucleic acid amplification reaction such as PCR and is preferably a reagent used for PCR. Specific examples thereof include dNTP and a DNA polymerase. As the DNA polymerase, it is preferable to use a thermostable DNA polymerase such as Taq DNA polymerase, Tth DNA polymerase, or Vent DNA polymerase, and it is more preferable to use a DNA polymerase having a hot start function for preventing elongation before the start of the test, or a proofreading (correcting) function. These reagents are commercially available and easily available.

((d) Cell-Free Protein Synthesis Reaction Solution)

The cell-free protein synthesis reaction solution of (d) is a reaction solution that is used in a cell-free protein synthesis system. Specific examples thereof include a cell extract containing components necessary for protein synthesis. Examples of the components required for protein synthesis include various factors such as ribosomes; initiation factors; tRNAs; and various enzymes such as RNA polymerases and aminoacyl tRNA synthases. Suitable examples thereof include an *Escherichia coli* S30 extract system (a prokaryotic cell system), a wheat germ extract system (a eukaryotic cell system), and a rabbit reticulocyte lysate system (a eukaryotic cell system). The reagents required for these cell-free protein synthesis systems are also commercially available as a kit and are easily available.

<<Second Aspect>>

In one embodiment, the present invention provides a kit for preparing a peptide-nucleic acid complex, where the kit contains the following (a) to (d);
  (a) a nucleic acid which contains a first coding sequence encoding any peptide or a cloning site into which a nucleic acid fragment containing the first coding sequence can be inserted, a second coding sequence encoding the transpeptidase, and a third coding sequence encoding a transpeptidase N-terminal substrate motif,
  (b) a primer set with which a region in the nucleic acid of (a), the region including the first coding sequence or the cloning site, the second coding sequence, and the third coding sequence, can be amplified and in which a transpeptidase recognition motif is added to any one of a forward primer or a reverse primer,
  (c) a nucleic acid amplification reagent, and
  (d) a cell-free protein synthesis reaction solution.

((a) Nucleic Acid)

The nucleic acid of (a) is a nucleic acid which contains a first coding sequence encoding any peptide or a cloning site into which a nucleic acid fragment containing the first coding sequence can be inserted, a second coding sequence encoding a transpeptidase, and a third coding sequence encoding a transpeptidase N-terminal substrate motif. These coding sequences are the same as those described above in "<Method for producing peptide-nucleic acid complex>".

The cloning site into which the nucleic acid fragment containing the first coding sequence can be inserted is not particularly limited and may be any restriction enzyme site. In a case where the nucleic acid fragment containing the first coding sequence is inserted into the above cloning site, the cloning site is arranged so that a chimeric protein, which is the protein that contains a domain of the peptide translated from the first coding sequence and the transpeptidase N-terminal substrate motif translated from the third coding sequence, and in which the transpeptidase N-terminal substrate motif is located on the N-terminal side of the domain of peptide, can be expressed. That is, the cloning site and the third coding sequence are arranged in the same ORF, and the cloning site is arranged on the 3' side of the third coding sequence.

The nucleic acid of (a) may further contain other sequences. Examples of the other sequences include the same sequences as those mentioned in "<Method for producing peptide-nucleic acid complex>" described above. For example, the nucleic acid of (a) may contain a sequence encoding any spacer between each of the coding sequences. Further, a regulatory sequence such as a promoter sequence that regulates the expression of the coding sequence may be included.

Examples of the nucleic acid of (a) include a nucleic acid having a configuration in which the third coding sequence, the first coding sequence or the cloning site, and the second coding sequence are arranged in order from the 5' side to the 3' side; and a nucleic acid having a configuration in which the third coding sequence, the second coding sequence, and the first coding sequence are arranged in order from the 5' side to the 3' side.

Preferred specific examples of the nucleic acid of (a) include the nucleic acids 30*d* and 30*e*, which are exemplified in "<Method for producing peptide-nucleic acid complex>" described above, and a nucleic acid obtained by substituting the first coding sequence in any one of the nucleic acids 30*d* and 30*e* with a cloning site.

The nucleic acid of (a) may further contain a fourth coding sequence encoding a protease recognition motif, where the fourth coding sequence is adjacent to the 5' terminal of the third coding sequence. The protease recognition motif is the same as that described in "<Method for producing peptide-nucleic acid complex>" described above.

The nucleic acid of this embodiment may be a plasmid as in the nucleic acid of (a) in the first aspect. Examples of the plasmid include the same plasmids as those mentioned in the first aspect.

((b) Primer Set)

The primer set of (b) is a primer set capable of amplifying a region (a coding sequence region) containing the first coding sequence or the cloning site, the second coding sequence, and the third coding sequence in the nucleic acid of (a). The transpeptidase recognition motif is added to any one of a forward primer or a reverse primer of the primer.

It is preferable that the primer set of (b) be capable of amplifying a coding sequence region in (a) and a region including a regulatory sequence that regulates transcription or translation of the corresponding coding sequence. A primer set capable of amplifying the region can be designed based on a known method. The transpeptidase recognition motif can be added to the primer in the same manner as in the method described above in "<Method for producing peptide-nucleic acid complex>".

In the primer set of (b) of the kit of this embodiment, any one of the forward primer or the reverse primer may be immobilized on a solid phase carrier. In this case, the primer set of (b) may be any of the following (i) to (iv);
  (i) a set of a forward primer having a 5' terminal to which a transpeptidase recognition motif has been added and a reverse primer having a 5' terminal which has been immobilized on a solid phase carrier, (ii) a set of a forward primer having a 5' terminal to which a transpeptidase recognition motif has been added and a reverse primer having a 5' terminal to which a substance having a binding affinity to a solid phase carrier has been added, (iii) a set of a forward primer having a 5' terminal which has been immobilized on a solid phase carrier and a reverse primer having a 5' terminal to which a transpeptidase recognition motif has been added, and (iv) a set of a forward primer having a 5' terminal to which a substance having a binding affinity to a solid phase carrier has been added and a reverse primer having a 5' terminal to which a transpeptidase recognition motif has been added.

In the above (i) to (iv), examples of the method for immobilizing the primer on the solid phase carrier and the substance having the binding affinity to the solid phase carrier include the same methods and the substances as those mentioned in the first aspect.

((c) Nucleic Acid Amplification Reagent and (d) Cell-Free Protein Synthesis Reaction Solution)

The nucleic acid amplification reagent of (c) and the cell-free protein synthesis reaction solution of (d) are the same as those in the first aspect.

The kit of this embodiment can be suitably used for producing a peptide-nucleic acid complex.

EXAMPLES

The present invention will be described with reference to Examples.

However, the embodiments of the present invention are not limited to the descriptions of these Examples.

1. Nucleic Acid-Peptide Complex Containing Polyphosphate Kinase

[Synthesis Example 1] Synthesis of DNA Primer to which Pentaglycine is Added

Figure 7:
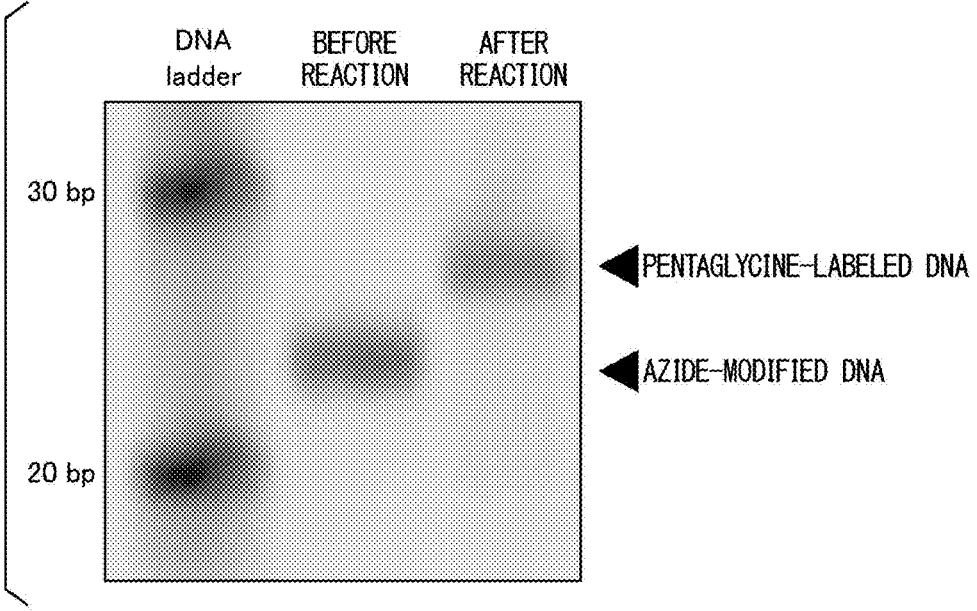
FIG. 7 is a photograph taken after polyacrylamide gel electrophoresis of a DNA primer to which pentaglycine has been added, where the DNA primer was synthesized in Synthesis Example 1.

A reaction solution having the following composition was prepared for a reaction, and after the reaction at room temperature for 10 minutes, purification by gel filtration was carried out using Micro Bio-Spin™ 6 (Promega Corporation). The purified product was subjected to polyacrylamide gel electrophoresis, and a band of the DNA (the pentaglycine-labeled DNA) to which pentaglycine had been added was confirmed (FIG. 7).
(Composition of Reaction Solution)
2 µM of azide-modified DNA
200 µM of alkyne modified pentaglycine
100 µM of sodium ascorbate
20 µM of copper sulfate (II)
50% of tert-butyl alcohol

```
Azide-modified DNA:
                                (SEQ ID NO: 29)
5'-[azide]-CGCCAATCCGGATATAGTTC-3'

Alkyne-modified pentaglycine:
                                (SEQ ID NO: 43)
(N)-Gly-Gly-Gly-Gly-Gly-Gly(propargyl)-(C)
```

[Synthesis Example 2] Synthesis of DNA to which Pentaglycine is Added

PCR reaction solutions 1 and 2 having the following compositions were prepared, and PCR was performed for 30 cycles (98° C., 10 seconds; 55° C., 5 seconds; 72° C., 2 minutes). The PCR product was purified using a QIAquick (registered trademark) PCR purification column (QIAGEN). PCR was carried out using the PCR reaction solution 1, whereby a DNA to which a pentaglycine was added (hereinafter referred to as a "pentaglycine-added DNA") was obtained. PCR was carried out using the PCR reaction solution 2, whereby a DNA to which a pentaglycine was not added (hereinafter referred to as a "pentaglycine-non-added DNA") was obtained.

Figure 8:
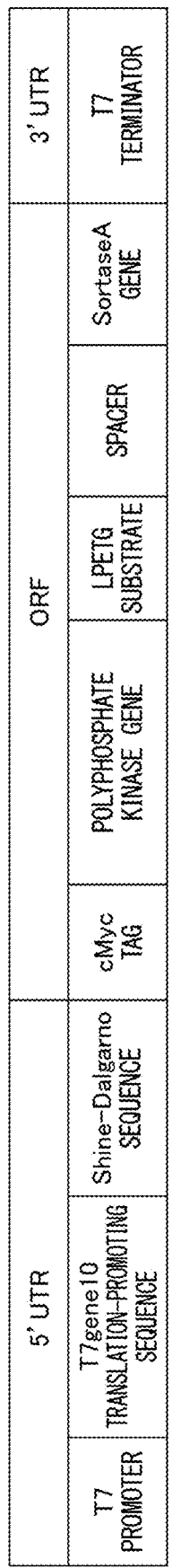
FIG. 8 shows a structure of a template DNA used in PCR in Synthesis Example 2.
Figure 9:
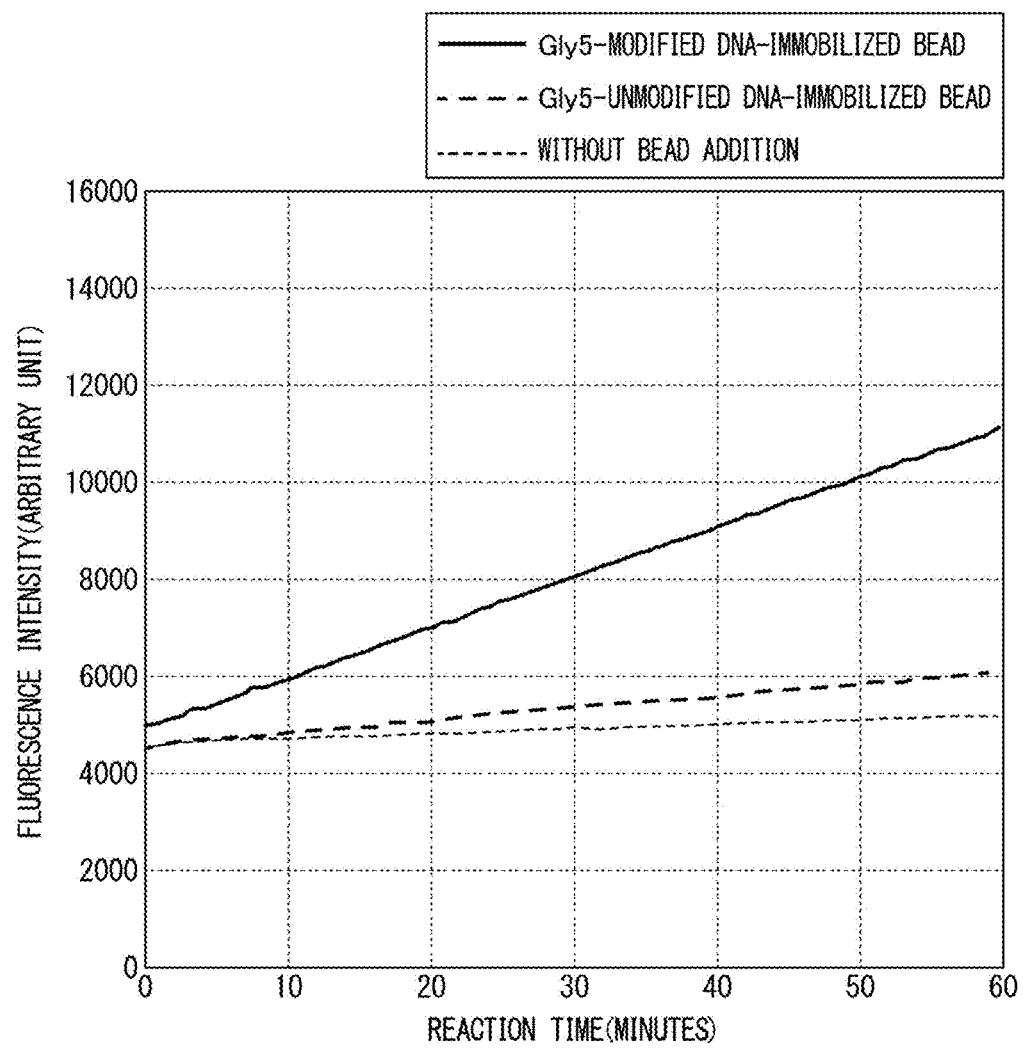
FIG. 9 is a graph showing measurement results of polyphosphate kinase activity of a magnetic bead on which a pentaglycine-added DNA is immobilized, after being subjected to cell-free protein translation in Experimental Example 2.

The configuration of the template DNA (SEQ ID NO: 44) used in the following PCR reaction solution is shown in FIG. 8. As shown in FIG. 8, the template DNA has an ORF containing coding sequences of the polyphosphate kinase gene, the sortase A gene, and the sortase A recognition motif (LPETG (SEQ ID NO: 14)). In the template DNA, the sortase A recognition motif (LPETG (SEQ ID NO: 14)) coding sequence is located on the 3' side of the polyphosphate kinase gene. The base sequence of the sortase gene A contained in the template DNA is shown in SEQ ID NO: 30.

<Composition of PCR Reaction Solution 1>
20 pg/µL of template DNA
0.3 µM of pentaglycine-added DNA primer
0.3 µM of biotin-labeled DNA primer
0.2 µM of each dNTP Mix
0.025 U/µL of PrimeSTAR (registered trademark) HS polymerase (Takara Bio Inc.)
1× PrimeSTAR (registered trademark) buffer (Takara Bio Inc.)

<Composition of PCR Reaction Solution 2>
20 pg/µL of template DNA
0.3 µM of pentaglycine-non-added DNA primer
0.3 µM of biotin-labeled DNA primer
0.2 µM of each dNTP Mix
0.025 U/µL of PrimeSTAR (registered trademark) HS polymerase (Takara Bio Inc.)
1× PrimeSTAR (registered trademark) buffer (Takara Bio Inc.)

[Experimental Example 1] Preparation of Magnetic Bead on which Pentaglycine-Added DNA is Immobilized The supernatant was removed from 15 µL of streptavidin-modified magnetic beads (MS300/streptavidin, JSR Corporation) and the beads were washed with 30 µL of a binding buffer (10 mM Tris-HCl, 1 mM EDTA, 1 M NaCl, 0.05% (w/v) Tween 20, pH 7.4). The washed magnetic beads were suspended in 30 µL of a binding buffer in which 1 pmol of the pentaglycine-added DNA or pentaglycine-non-added DNA was dissolved and were stirred at room temperature for 30 minutes. Next, the magnetic beads were washed 3 times with 100 µL of the binding buffer and then suspended in 30 µL of the binding buffer.

[Experimental Example 2] Cell-Free Protein Translation from Pentaglycine-Added DNA The supernatant was removed from 10 µL of the magnetic beads on which a pentaglycine-added DNA or pentaglycine-non-added DNA was immobilized and the beads were suspended in 10 µL of a cell-free protein translation reaction solution (PUREfrex (registered trademark) 1.0, GeneFrontier Corporation). After stirring at 37° C. for 3 hours, the magnetic beads were washed 3 times with 100 µL of the binding buffer. The magnetic beads were then washed 3 times with 100 μL of 50 mM Tris-HCl (pH 7.5) and then suspended in 10 μL of 50 mM Tris-HCl (pH 7.5).

[Experimental Example 3] Measurement of Polyphosphate Kinase Activity

A mixture of 10 μL of the magnetic beads subjected to the cell-free protein translation treatment, 25 μL of an enzyme reaction solution (1 mM hexametaphosphoric acid, 0.1 mM ADP, 5 mM MgSO$_4$, 50 mM Tris-HCl, pH 7.5), and 25 μL of an ATP fluorescence detection reagent (ATP Colorimetric/Fluorometric Assay Kit, BioVision, Inc.) was subjected to a measurement over time to measure the fluorescence signal derived from ATP generated as a result of the catalytic reaction of the polyphosphate kinase by using a fluorescence plate reader.

The results are shown in Table 9. The polyphosphate kinase activity was confirmed in the case of the magnetic bead on which a pentaglycine-added DNA had been immobilized. This result indicates that a polyphosphate kinase obtained by cell-free translation from a pentaglycine-added DNA is immobilized on the bead in the case of the magnetic bead on which a pentaglycine-added DNA has been immobilized. On the other hand only a slight polyphosphate kinase activity, which was considered to be due to the non-specific adsorption of the polyphosphate kinase to the bead, was confirmed in the case of the magnetic bead on which a pentaglycine-non-added DNA had been immobilized.

Based on the above results, it has been demonstrated that in a case where the DNA (containing any gene, the sortase A gene, and the sortase A recognition motif) to which the N-terminal substrate motif for the sortase A has been added is subjected to cell-free protein translation, a protein translated from any gene can be linked to the gene encoding the protein.

2. Nucleic Acid-Peptide Complex Containing CP05 or Protein Kinase Inhibitor (PKI)

[Synthesis Example 3] Synthesis of DNA (CP05 Gene) to which Pentaglycine is Added As a template, a template DNA containing a DNA (a Xa motif-CP05) in which a coding sequence of a protease recognition motif (SEQ ID NO: 28) for Factor Xa was linked to the 5' terminal of a CP05 peptide gene (SEQ ID NO: 45 or 46) was used. The template DNA (SEQ ID NO: 47) has the Xa motif-CP05 instead of the polyphosphate kinase gene in the template DNA shown in FIG. 8A. A pentaglycine-added DNA was synthesized in the same manner as in Synthesis Example 1 and Synthesis Example 2, except that the CP05 peptide gene was used as the template DNA.

[Synthesis Example 4] Synthesis of DNA to which Pentaglycine is Added (PKI Gene)

As a template, a template DNA containing a DNA (a Xa motif-PKI) in which a coding sequence of a protease recognition motif (SEQ ID NO: 28) for Factor Xa was linked to the 5' terminal of a PKI gene (SEQ ID NO: 48 or 49) was used. The template DNA (SEQ ID NO: 50) has the Xa motif-PKI instead of the polyphosphate kinase gene in the template DNA shown in FIG. 8A.

A pentaglycine-added DNA was synthesized in the same manner as in Synthesis Example 1 and Synthesis Example 2, except that the above template DNA was used.

[Experimental Example 4] Preparation of Magnetic Bead on which Pentaglycine-Added DNA is Immobilized Magnetic beads on which a pentaglycine-added DNA was immobilized and magnetic beads on which a pentaglycine-non-added DNA was immobilized were prepared in the same manner as in the Experimental Example 2, except that the pentaglycine-added DNA synthesized in Synthesis Example 3 or Synthesis Example 4 was used.

[Experimental Example 5] Cell-Free Protein Translation from Pentaglycine-Added DNA The supernatant was removed from 15 μL of the magnetic beads on which a pentaglycine-added DNA or pentaglycine-non-added DNA was immobilized and the beads were suspended in 15 μL of a cell-free protein translation reaction solution (PUREfrex (registered trademark) 1.0, GeneFrontier Corporation). After stirring at 37° C. for 3 hours, the magnetic beads were washed 5 times with 100 μL of PBS-T. Next, the magnetic beads were suspended in 100 μL of PBS-T.

[Experimental Example 6] Antibody Staining

A dispersion medium of 25 μL of the magnetic bead suspension was removed, and the magnetic beads were suspended in any of the following solutions (a) to (c).
(a) 15 μL of FITC-labeled anti-cMyc antibody solution (abcam #ab117599) diluted with PBS-T.
(b) 15 μL of FITC-labeled anti-Isotype Control antibody solution (abcam #ab91356) diluted with PBS-T.
(c) 15 μL of PBS-T alone.

After suspending the magnetic beads, the suspension was stirred at room temperature for 1 hour with light shielding. Next, the magnetic beads were washed 3 times with 100 μL of PBS-T. Next, the magnetic beads were washed once with 100 μL of PBS. Next, the magnetic beads were suspended in 15 μL of PBS and observed under a fluorescence microscope (Eclipse Ti-E, Nikon Corporation; an EM-CCD camera, a B-2A filter, a xenon lamp, Hamamatsu Photonics K.K.). The fluorescence intensity of the magnetic bead was analyzed by ImageJ from the captured image taken under the fluorescence microscope.

Figure 10:
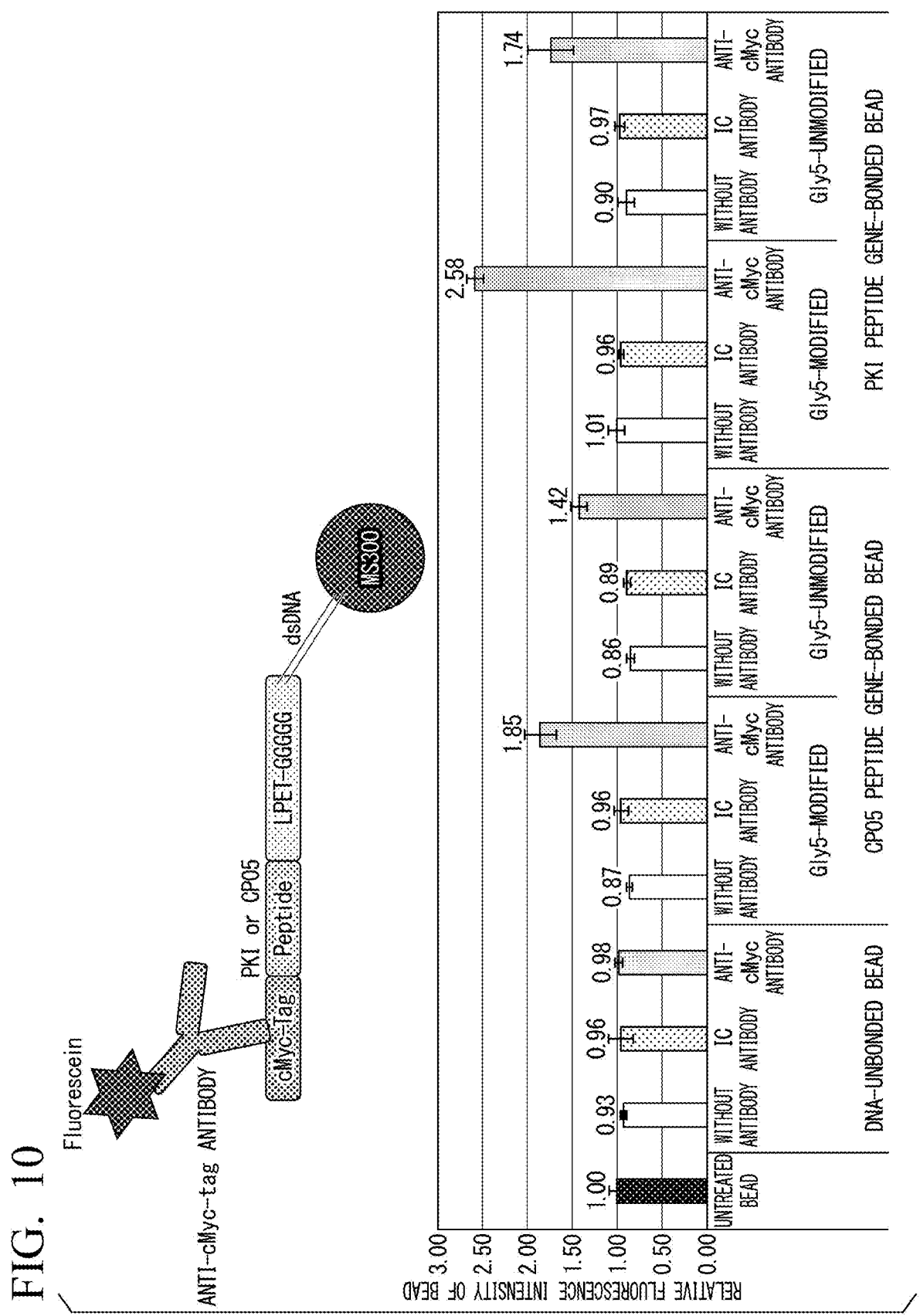
FIG. 10 is a graph showing results of antibody staining of the magnetic bead on which a pentaglycine-added DNA is immobilized in Experimental Example 6.
Figure 11:
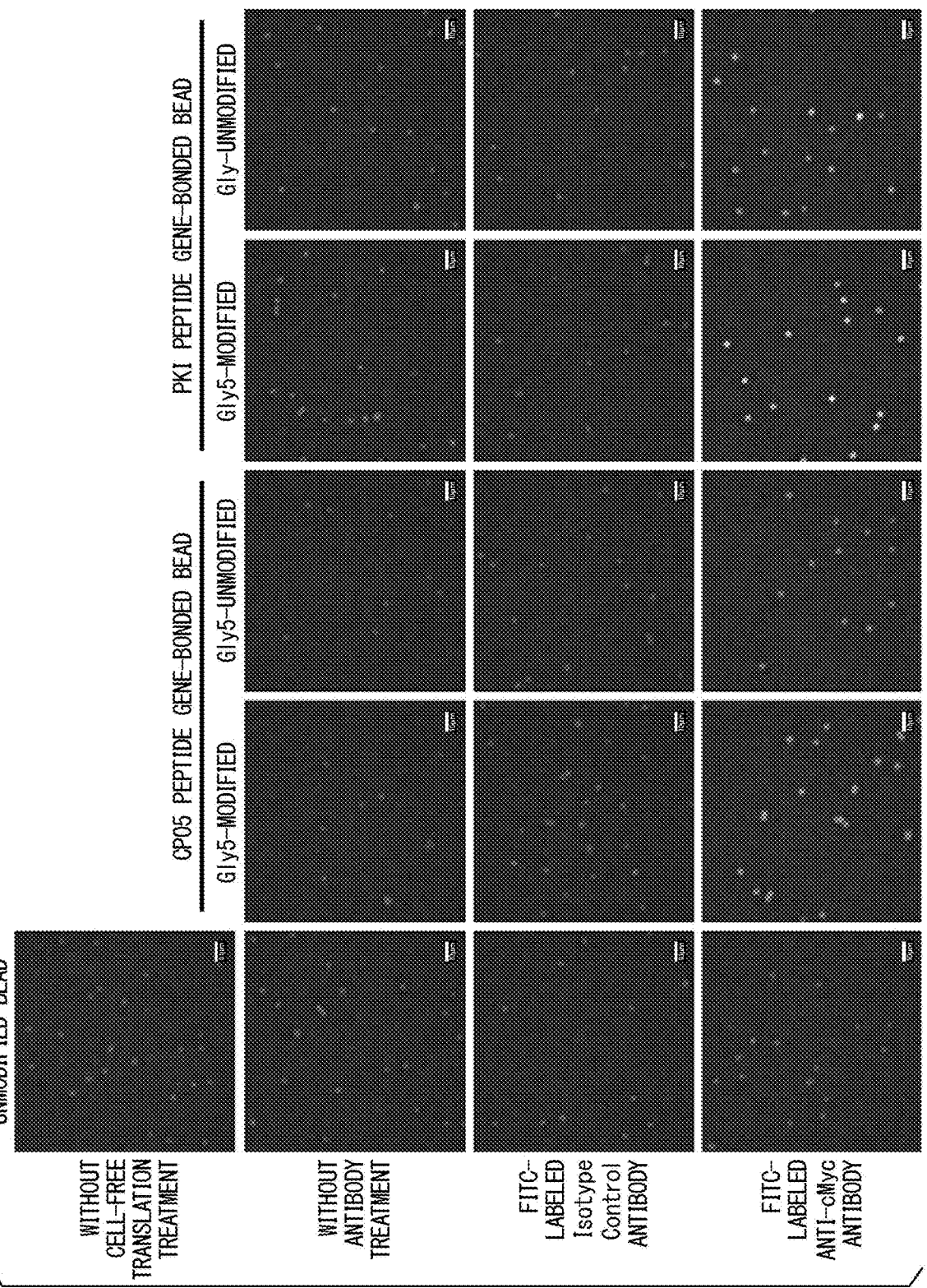
FIG. 11 shows fluorescence photomicrographs which show the results of antibody staining of the magnetic bead on which a pentaglycine-added DNA is immobilized in Experimental Example 6.

The results are shown in FIGS. 10 and 11. As shown in FIG. 10, in the case of the bead on which a pentaglycine-added DNA was immobilized, the fluorescence intensity was enhanced in a case where the FITC-labeled anti-cMyc antibody was treated for reaction. On the other hand, even in the case of the bead on which a pentaglycine-non-added DNA was immobilized, the fluorescence intensity was slightly enhanced in a case where the FITC-labeled anti-cMyc antibody was treated for reaction; however, the degree of enhancement was small as compared with the case of the bead on which a pentaglycine-added DNA was immobilized. FIG. 11 shows fluorescence photomicrographs of each magnetic bead.

From the results of FIGS. 10 and 11, it was presumed that in the case of the bead on which a pentaglycine-added DNA was immobilized, the protein containing a cMyc tag was linked to the DNA immobilized on the bead and containing a cMyc tag coding sequence. As a result, it was presumed that the fluorescence intensity was greatly enhanced by treating the FITC-labeled anti-cMyc antibody for reaction.

3. Preparation of Peptide Array

A peptide array was prepared using the magnetic bead on which a nucleic acid-peptide complex was immobilized, which was prepared in Experimental Example 2. 5 µL of the magnetic beads subjected to the cell-free protein translation treatment in Experimental Example 2 was mixed with 9 µL of an enzyme reaction solution (3.3 mM hexametaphosphoric acid, 0.33 mM ADP, 16. 7 mM $MgSO_4$) and 15 µL of an ATP fluorescence detection reagent (ATP Colorimetric/Fluorometric Assay Kit, BioVision, Inc.).

The magnetic bead suspension prepared as described above was added dropwise onto a quartz glass chip in which one million holes having a diameter of 4 µm and a depth of 4 µm were formed in a 1 cm×1 cm square, and each well was filled with the magnetic beads and a bead dispersion medium. The surface of the chip was coated with silicone oil (Shin-Etsu Chemical Co., Ltd., KF96-100cs) to seal each well. Thereafter, time-lapse imaging was performed with a fluorescence microscope (Eclipse Ti-E, Nikon Corporation; an EM-CCD camera, a Cy3 filter, xenon lamp, Hamamatsu Photonics K.K.), and an increase in the fluorescence brightness of each well was observed. ImageJ was used to carry out the analysis of the change in the fluorescence brightness of each well.

Figure 12A:
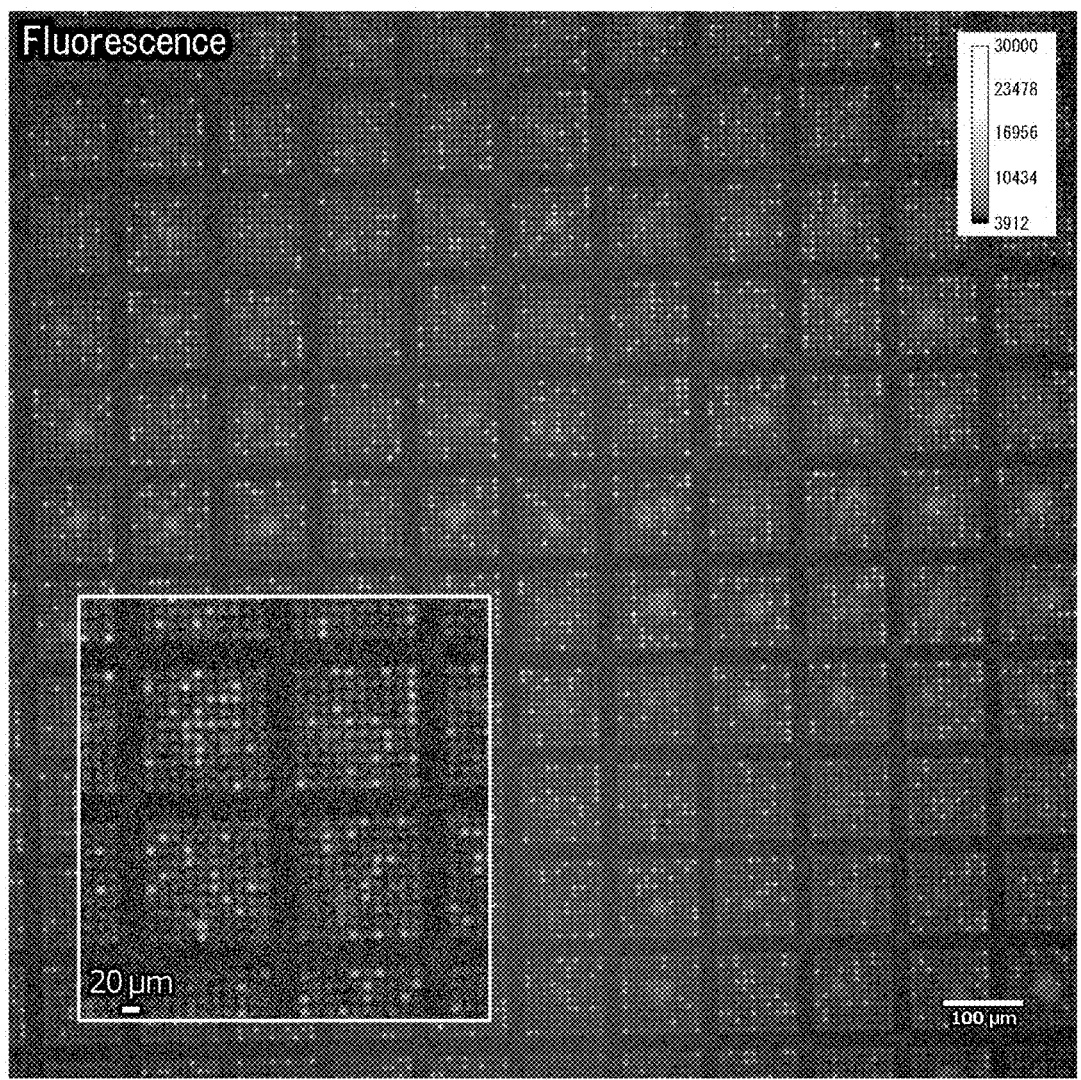
FIG. 12A shows a fluorescence photomicrograph of a peptide array prepared in Examples.
Figure 12B:
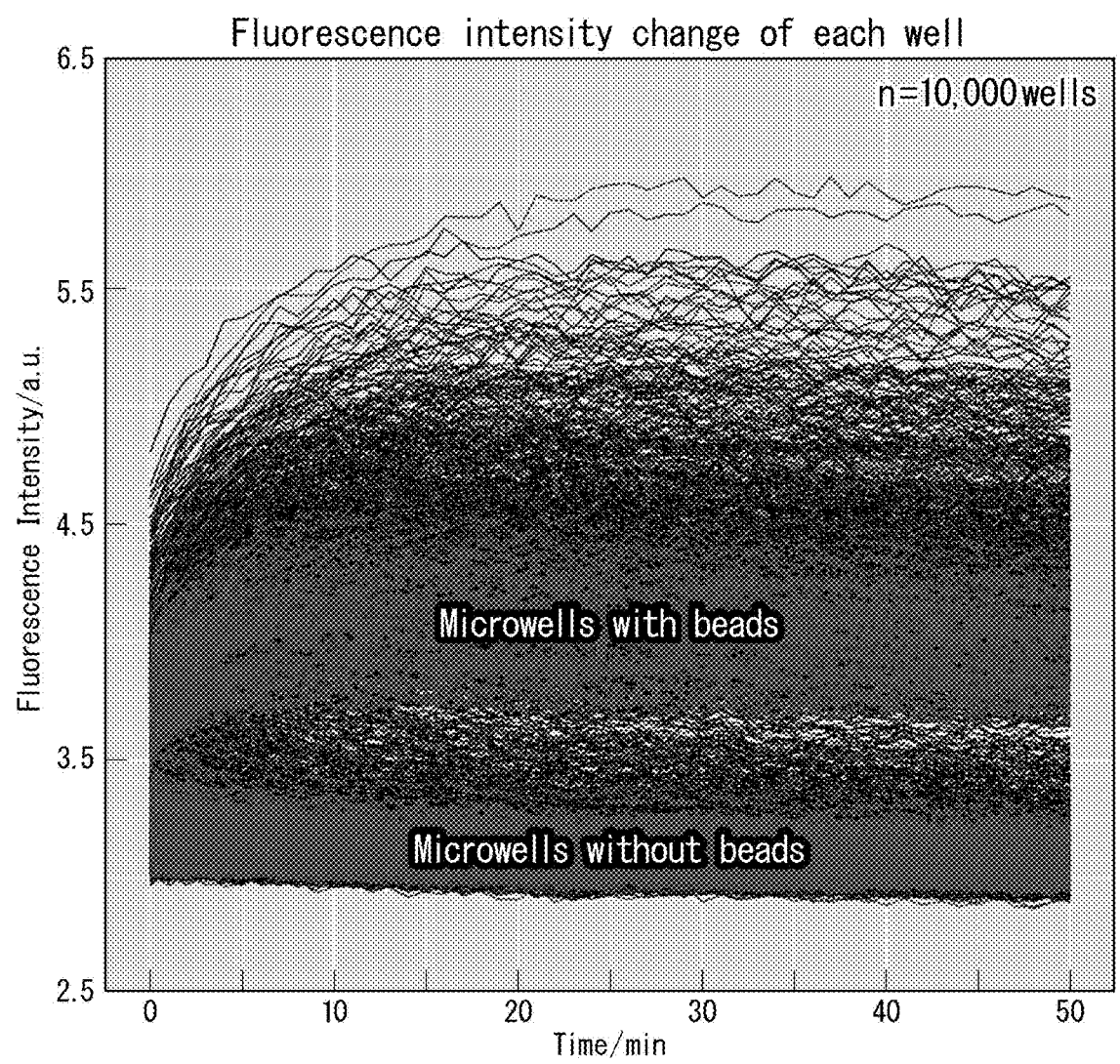
FIG. 12B is a graph showing the transition of the fluorescence intensity in each well of the peptide array prepared in Examples.
Figure 13:
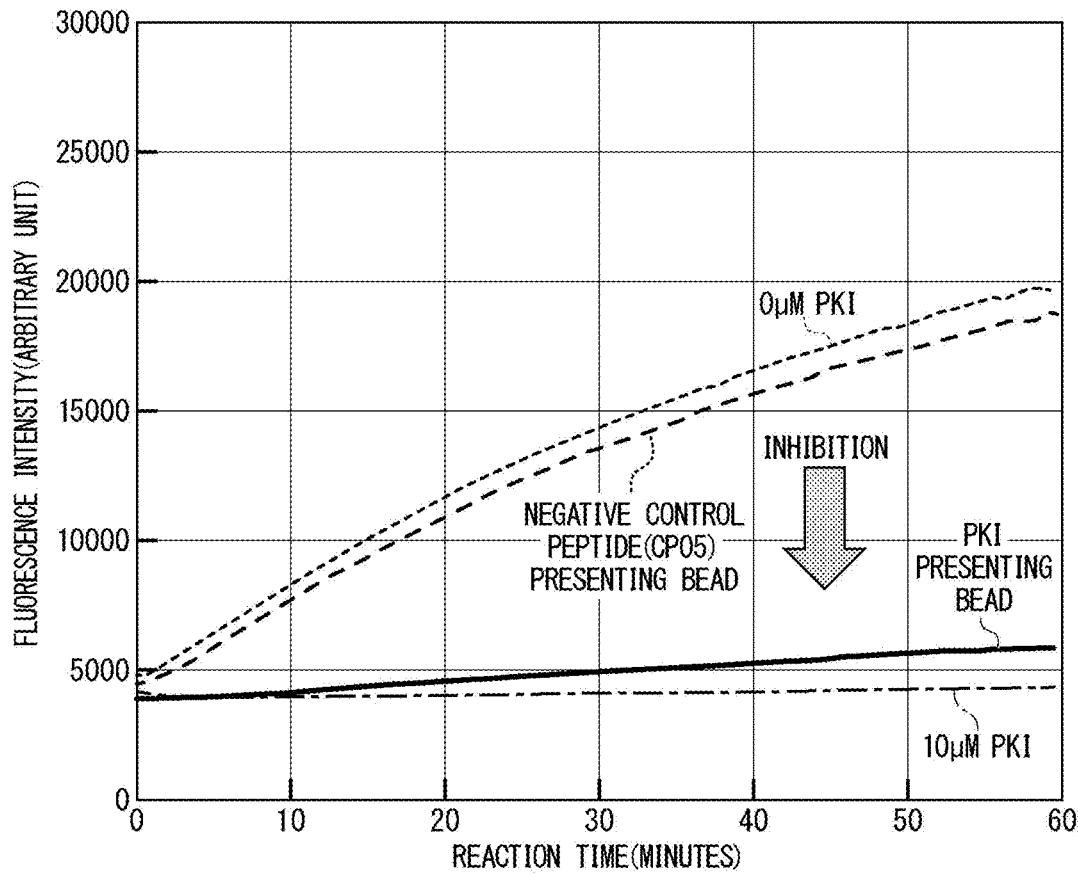
FIG. 13 a graph showing results obtained by measuring the inhibitory effect on protein kinase A (PKA) activity by the magnetic bead on which a pentaglycine-added DNA is immobilized in Experimental Example 9.

The results are shown in FIG. 12A and FIG. 12B. The increase in fluorescence brightness was observed only in the well filled with the magnetic bead on which a nucleic acid-peptide complex was immobilized. From these results, it has been confirmed that a peptide array can be prepared by using the magnetic bead on which a nucleic acid-peptide complex is immobilized, which is prepared in the present method.

4. Protein Kinase A (PKA) Inhibitory Activity of Nucleic Acid-Peptide Complex Containing PKI

[Experimental Example 7] Preparation of Magnetic Bead on which Pentaglycine-Added DNA is Immobilized Magnetic beads on which a pentaglycine-added DNA was immobilized were prepared in the same manner as in the Experimental Example 2, except that the pentaglycine-added DNA (containing the PKI gene) synthesized in Synthesis Example 4 was used. As the negative control magnetic bead, magnetic beads on which a pentaglycine-added DNA was immobilized were prepared in the same manner as in the Experimental Example 2, using the pentaglycine-added DNA (containing the CD05 gene) synthesized in Synthesis Example 3.

[Experimental Example 8] Cell-Free Protein Translation of Pentaglycine-Added DNA The supernatant was removed from 15 µL of the magnetic beads on which a pentaglycine-added DNA (containing the PKI gene) was immobilized or 15 µL of the magnetic beads on which a pentaglycine-added DNA (containing the CD05 gene) was immobilized, and the beads were suspended in 15 µL of a cell-free protein translation reaction solution (PUREfrex (registered trademark) 1.0, GeneFrontier Corporation). After stirring at 37° C. for 3 hours, the magnetic beads were washed 5 times with 100 µL of the binding buffer. Next, the magnetic beads were washed 5 times with 100 µL of a 1×PKA buffer (40 mM Tris-HCl (pH 7.5), 20 mM MgCl2, 0.1 mg/ml BSA). Next, the magnetic beads were suspended in 3 µL of the 1×PKA buffer.

[Experimental Example 9] Measurement of PKA Inhibitory Activity

3 µL of magnetic beads which had been subjected to a cell-free protein translation treatment, 7 µL of a kinase reaction solution, and 15 µL of a 2×RT detection solution (Fluorospark (registered trademark), FUJIFILM Wako Pure Chemical Corporation) were mixed. Next, the fluorescence signal derived from ADP generated as a result of the catalytic reaction of protein kinase A was measured using a fluorescence plate reader.

The composition of the kinase reaction solution is shown below.
<Kinase Reaction Solution>
0.06 mU/µL of Protein kinase A (SignalChem Biotech Inc., #p51-10G)
5 µM of ATP
100 µM of Kemptide (Promega Corporation, V5601)
3.6×PKA buffer The measurement conditions for the fluorescence signal are shown below.
30° C., 60 minutes
Excitation: 540 BP 20 nm
Fluorescence: 590 BP 20 nm The results are shown in Table 13. In the case of the bead on which a nucleic acid-peptide complex containing PKI was immobilized, the fluorescence intensity was maintained at a low level. In the case of the bead on which a nucleic acid-peptide complex containing PKI was immobilized, the fluorescence intensity was maintained at almost the same level as in a case where 10 µM PKI was added to the PKA reaction solution as a positive control.

On the other hand, the fluorescence intensity increased with the lapse of reaction time in the case of the negative control magnetic bead. The negative control magnetic bead exhibited almost the same fluorescence intensity increase as the PKA reaction solution to which PKI was not added.

From these results, it has been confirmed that a PKI nucleic acid-PKI peptide complex is formed in the case of the bead on which a nucleic acid-peptide complex containing PKI is immobilized.

5. Exosome Bonding Activity of Nucleic Acid-Peptide Complex Containing CP05

[Experimental Example 10] Preparation of Magnetic Bead on which Pentaglycine-Added DNA is Immobilized Magnetic beads on which a pentaglycine-added DNA was immobilized and magnetic beads on which a pentaglycine-non-added DNA was immobilized were prepared in the same manner as in the Experimental Example 2, except that the pentaglycine-added DNA (containing the CP05 gene) synthesized in Synthesis Example 3 was used.

[Experimental Example 11] Cell-Free Protein Translation of Pentaglycine-Added DNA The supernatant was removed from 15 µL of the magnetic beads on which a pentaglycine-added DNA was immobilized, and the beads were suspended in 15 µL of a cell-free protein translation reaction solution (PUREfrex (registered trademark) 1.0, GeneFrontier Corporation). After stirring at 37° C. for 3 hours, the magnetic beads were washed 5 times with 100 µL of the binding buffer. Next, the magnetic beads were washed once with 100 µL of a Factor Xa buffer (20 mM Tris-HCl (pH 7.5), 100 mM NaCl). Next, the magnetic beads were suspended in the Factor Xa buffer.

[Experimental Example 12] Factor Xa Protease Treatment

1 µL of Factor Xa protease (Promega Corporation) was added to 30 µL of a magnetic bead suspension, and the mixture was stirred at 25° C. for 17 hours.

By the cell-free protein translation treatment of Experimental Example 11, a chimeric protein of a cMyc tag-Factor Xa protease recognition motif-CP05-LPETG-sortase A is translated from a pentaglycine-added DNA encoding the chimeric protein. Next, through the transpeptidation reaction by the sortase A, a cMyc tag-Factor Xa protease recognition motif-CP05-LPETG is linked to a pentaglycine-added DNA to form a peptide-nucleic acid complex. In a case where Factor Xa protease is allowed to act on this peptide-nucleic acid complex, the peptide-nucleic acid complex is cleaved at the Factor Xa protease recognition motif. As a result, the cMyc tag is cleaved from the peptide-nucleic acid complex.

[Experimental Example 13] Preparation of Fluorescently Labeled Extracellular Vesicles (EV)

150 µL of human plasma was centrifuged (1,500×g, 10 minutes, 25° C.), and the supernatant was recovered. The recovered supernatant was centrifuged (3,000×g, 10 minutes, 25° C.), and the supernatant was recovered. The recovered supernatant was further centrifuged (3,000×g, 10 minutes, 25° C.), and the supernatant was recovered. Next, the recovered supernatant was purified by Exosome Spin Column (Thermo Fisher Scientific, Inc.). Next, the purified sample was concentrated to 100 µL using an ultrafiltration column (MWCO: 100K). PKH67 (Sigma-Aldrich Co., LLC) was added thereto (final concentration: 2 µM), and the mixture was allowed to react at room temperature for 10 minutes with light shielding. After the reaction, the reaction solution was purified by Exosome Spin Column (Thermo Fisher Scientific, Inc.). The purified sample was used as the fluorescently labeled EV.

[Experimental Example 14] Reaction with a Fluorescently Labeled EV Sample and Observation Under Fluorescence Microscope The magnetic beads treated with Factor Xa protease in Experimental Example 12 were washed 5 times with 100 µL PBS-T. Next, the magnetic beads were suspended in 15 µL of PBS-T. 7.5 µL of the dispersion medium was removed from the magnetic bead suspension, and the magnetic bead suspension was suspended in 50 µL of a sample of the fluorescently labeled EV prepared in Experimental Example 13. Next, the suspension was stirred at room temperature for 1 hour with light shielding. Next, the magnetic beads were washed 4 times with 100 µL of PBS. Next, the magnetic beads were suspended in 15 µL of PBS.

The magnetic bead suspension prepared as described above was observed under a fluorescence microscope (Eclipse Ti-E, Nikon Corporation; an EM-CCD camera, a B-2A filter, xenon lamp, Hamamatsu Photonics K.K.). The fluorescence intensity of the magnetic bead was analyzed by ImageJ from the captured image.

Figure 14A:
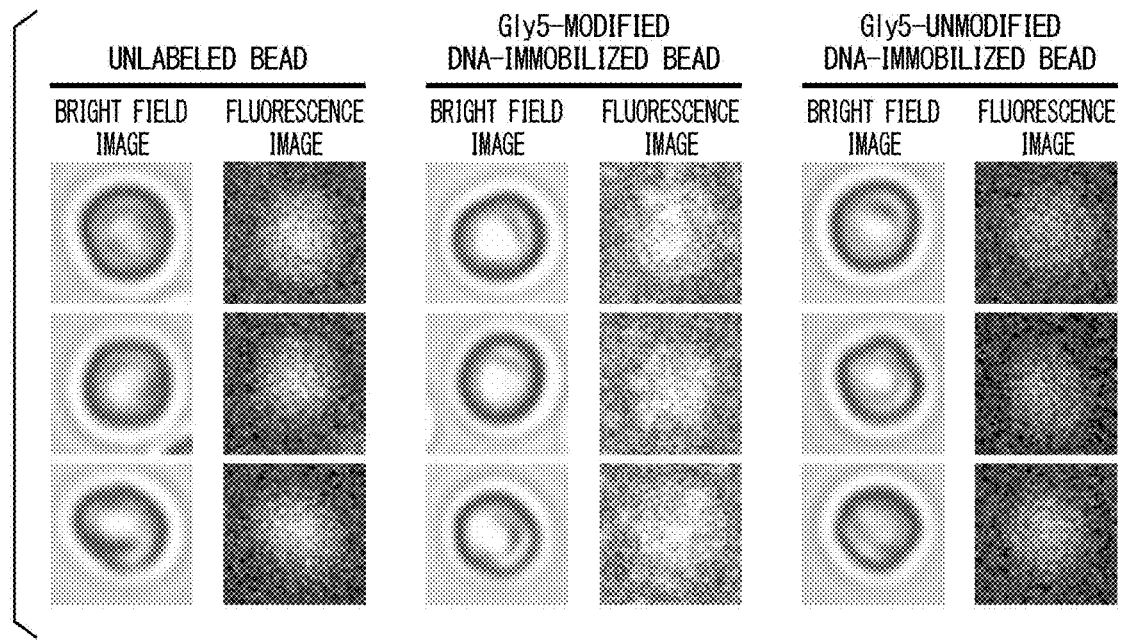
FIG. 14A shows results obtained by reacting the magnetic beads on which a pentaglycine-added DNA is immobilized with fluorescently labeled extracellular vesicles, and observing the magnetic beads under a fluorescence microscope in Experimental Example 14.
Figure 14B:
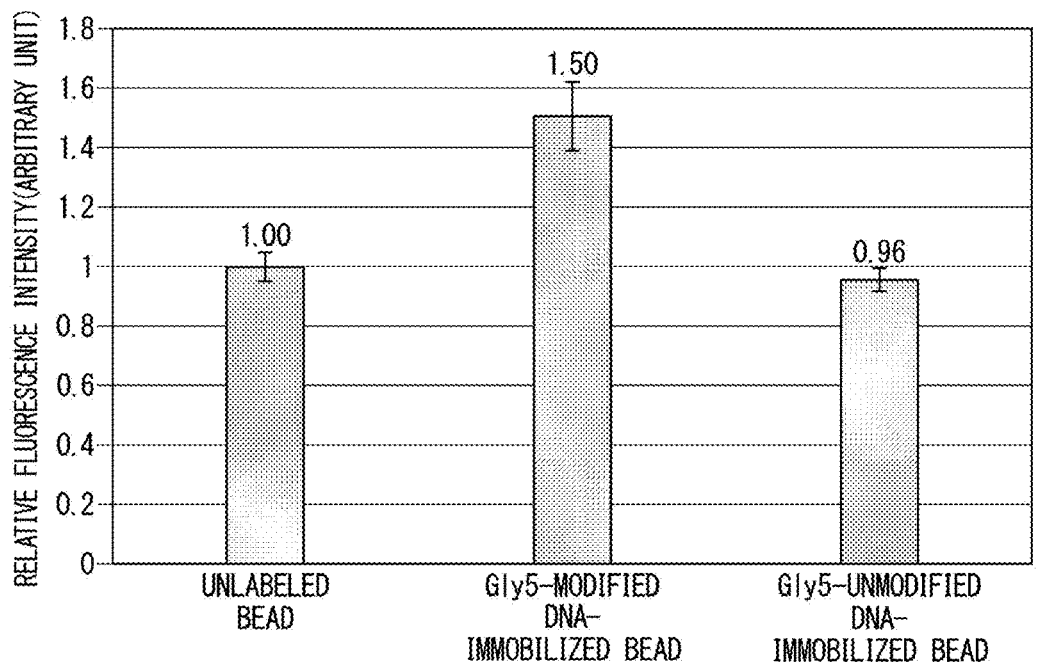
FIG. 14B is a graph showing results obtained by reacting the magnetic beads on which a pentaglycine-added DNA is immobilized with fluorescently labeled extracellular vesicles, and detecting fluorescence intensity in Experimental Example 14.
Figure 15:
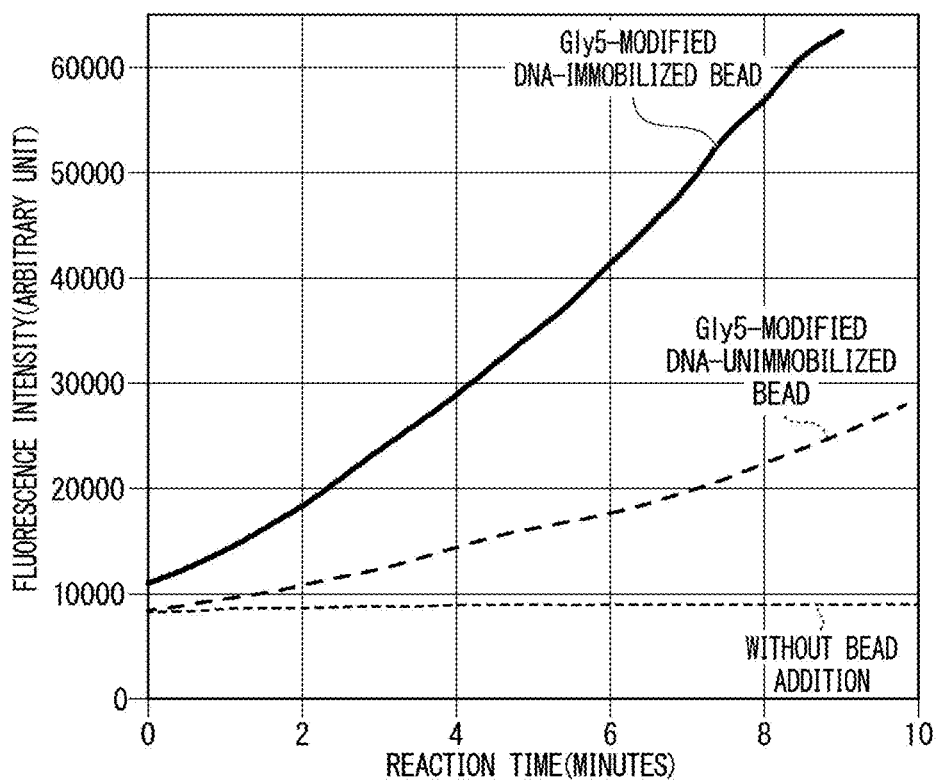
FIG. 15 is a graph showing results obtained by measuring polyphosphate kinase activity in Experimental Example 18, after carrying out emulsion PCR and emulsion cell-free protein translation.

The results are shown in FIG. 14A and FIG. 14B. CP05 has a binding affinity to CD63, which is a surface antigen of EV. As a result, in a case where a peptide-nucleic acid complex that presents CP05 is formed, the fluorescently labeled EV should bind to CP05 of the complex and fluorescence should be observed.

As shown in FIG. 14A and FIG. 14B, in the case of the magnetic bead on which a pentaglycine-added DNA was immobilized, a high fluorescence intensity was exhibited as compared with the magnetic bead on which a DNA was not immobilized and the magnetic bead on which a pentaglycine-non-added DNA was immobilized. This result indicates that a peptide-nucleic acid complex that presents CP05 is formed in the case of the magnetic bead on which a pentaglycine-added DNA is immobilized.

6. Preparation of Peptide-Nucleic Acid Complex by Emulsion PCR

[Experimental Example 15] Preparation of Bead on which Primer is Immobilized

The supernatant was removed from 240 µL of streptavidin-modified magnetic beads (MS300/streptavidin, JSR Corporation) and the beads were washed with 1,200 µL of a binding buffer (10 mM Tris-HCl, 1 mM EDTA, 1 M NaCl, 0.05% (w/v) Tween 20, pH 7.4). The magnetic beads were suspended in 480 µL of a binding buffer in which 48 pmol of a biotin-labeled DNA primer was dissolved, and the suspension was stirred at room temperature for 1 hour. Next, the magnetic beads were washed once with 1,200 µL of the binding buffer. The magnetic beads were then washed twice with 240 µL of a 1× buffer for KOD Plus polymerase (TOYOBO Co., Ltd.). The magnetic beads were then suspended in 240 µL of the 1× buffer for KOD Plus polymerase (TOYOBO Co., Ltd.).

[Experimental Example 16] Emulsion PCR

A PCR reaction solution 3 having the following composition and an oil mixture 1 were mixed and stirred to form an emulsion. This emulsion was aliquoted to 50 µL, and then PCR was performed. PCR was carried out under the conditions of 95° C. for 5 minutes (94° C., 30 seconds; 55° C., 1 minute; 68° C., 6 minutes) and 30 cycles, and the reaction sample was maintained at 10° C. after the PCR reaction. The same template DNA as in Synthesis Example 2 was used.
<Composition of PCR Reaction Solution 3>
2.4e8 particles of primer-bound magnetic bead
1.2e8 molecules of template DNA
180 pmol of pentaglycine-added DNA primer
180 pmol of DNA primer
30 µL of 2 mM dNTP Mix
18 µL of 25 mM of $MgSO_4$
30 µL of 10×KOD plus buffer (TOYOBO Co., Ltd.)
12 µL of 1 U/µL KOD plus polymerase (TOYOBO Co., Ltd.)
Up to 300 µL with nuclease Free Water
300 µL in total
<Oil Mixture 1>
540 µL of TEGOSOFT DEC (Evonik Industries AG)
204 µL of mineral oil (Nacalai Tesque, Inc.)
756 µL of ABIL WE09 (Evonik Industries AG)
1,500 µL in total After PCR, 7.6 mL of a disruption buffer (80% isopropanol, 0.6 M sodium acetate (pH 5.2), 1% Tween 20) was added and mixed. Magnetic beads were collected using a magnet and the supernatant was removed. Next, the magnetic beads were washed 5 times with 4 mL of a TK buffer (10 mM Tris-HCl (pH 7.5), 50 mM KCl, 0.01% Tween 20). The PCR product on the magnetic bead was stained with SYBR Green I, and the double-stranded DNA-bound magnetic beads were sorted by FACS (using BD, FACSArea).

[Experimental Example 17] Emulsion Cell-Free Protein Translation

A cell-free protein translation solution having the following composition and an oil mixture 2 were mixed and stirred to form an emulsion. Using the emulsion, cell-free translation reaction was carried out at 37° C. for 3 hours. As a negative control experiment, magnetic beads on which a DNA was not immobilized were subjected to the same treatment as above.

<Cell-Free Protein Translation Solution>

5e6 particles of the magnetic beads which had been subjected to the emulsion PCR were suspended in 63 µL of a PUREfrex 1.0 reaction solution, and the resultant suspension was used as the cell-free protein translation solution.

<Oil Mixture 2>

113 µL of TEGOSOFT DEC (Evonik Industries AG)
43 µL of mineral oil (Nacalai Tesque, Inc.)
159 µL of ABIL WE09 (Evonik Industries AG)
315 µL in total After the cell-free protein translation reaction, 750 µL of the disruption buffer was added and mixed. Magnetic beads were collected using a magnet and the supernatant was removed. The magnetic beads were washed 3 times with 1.9 mL of the disruption buffer. Next, the magnetic beads were washed 5 times with 250 µL of the wash buffer. Next, the magnetic beads were washed once with 250 µL of Tris-HCl (pH 7.5). Next, the magnetic beads were suspended in 6 µL of Tris-HCl (pH 7.5).

[Experimental Example 18] Measurement of Polyphosphate Kinase Activity

A mixture of 6 µL of the magnetic beads subjected to the cell-free protein translation treatment, 9 µL of an enzyme reaction solution (3.3 mM hexametaphosphoric acid, 0.33 mM ADP, 16.7 mM $MgSO_4$), and 15 µL of an ATP fluorescence detection reagent (ATP Colorimetric/Fluorometric Assay Kit, BioVision, Inc.) was subjected to a measurement over time to measure the fluorescence signal derived from ATP generated as a result of the catalytic reaction of the polyphosphate kinase by using a fluorescence plate reader.

The results are shown in Table 15. The polyphosphate kinase activity was confirmed in the case of the magnetic bead on which a pentaglycine-added DNA had been immobilized. This result indicates that a polyphosphate kinase obtained by cell-free translation from a pentaglycine-added DNA is immobilized on the bead in the case of the magnetic bead on which a pentaglycine-added DNA has been immobilized. On the other hand only a slight polyphosphate kinase activity, which was considered to be due to the non-specific adsorption of the polyphosphate kinase to the bead, was confirmed in the case of the magnetic bead on which a pentaglycine-non-added DNA had been immobilized.

From the above results, it has been demonstrated that even in a case where the emulsion PCR and the emulsion cell-free protein translation are used, a protein translated from any gene can be linked to the gene encoding the protein as in the case of Experimental Example 1 and Experimental Example 2.

REFERENCE SIGNS LIST

10: Peptide
20: Transpeptidase
21: Transpeptidase N-terminal substrate motif
22: Transpeptidase recognition motif
22': Sequence generated by cleavage of transpeptidase recognition motif
22': Sequence generated by cleavage of transpeptidase recognition motif
30a, 30b, 30c, 30d, 30e: Nucleic acid
40: Protease
100, 200, 300: Nucleic acid to which transpeptidase N-terminal substrate motif has been added (NS-added nucleic acid)
101, 201, 301, 401, 401', 501, 501': Chimeric protein
102, 202, 302, 402, 502: Peptide-nucleic acid complex
103, 203, 303, 403, 503: Transpeptidation reaction product
400, 400', 500, 500': Nucleic acid to which transpeptidase recognition motif has been added (TPR-added nucleic acid)

---

What is claimed is:

1. A peptide-nucleic acid complex comprising:
   (a) a peptide;
   (b) a nucleic acid containing a coding sequence of the peptide; and
   (c) a sequence generated by bonding a transpeptidase recognition motif and a transpeptidase N-terminal substrate motif through a transpeptidation reaction by the transpeptidase, the sequence of (c) being located between the peptide of (a) and the nucleic acid of (b).

2. The peptide nucleic acid complex according to claim 1, wherein the nucleic acid of (b) contains a first coding sequence encoding the peptide of (a), a second coding sequence encoding the transpeptidase, and a third coding sequence encoding the transpeptidase recognition motif or the transpeptidase N-terminal substrate motif.

3. The peptide nucleic acid complex according to claim 2, wherein the third coding sequence is a sequence encoding the transpeptidase recognition motif, and
the first coding sequence, the third coding sequence, and the second coding sequence are arranged in order from a 5' side to a 3' side in the nucleic acid of (b).

4. The peptide nucleic acid complex according to claim 2, wherein the third coding sequence is a sequence encoding the transpeptidase recognition motif, and
the second coding sequence, the first coding sequence, and the third coding sequence are arranged in order from a 5' side to a 3' side in the nucleic acid of (b).

5. The peptide nucleic acid complex according to claim 2, wherein the third coding sequence is a sequence encoding the transpeptidase recognition motif, and
the first coding sequence, the second coding sequence, and the third coding sequence are arranged in order from a 5' side to a 3' side in the nucleic acid of (b).

6. The peptide nucleic acid complex according to claim 2, wherein the third coding sequence is a sequence encoding the transpeptidase N-terminal substrate motif, and
the third coding sequence, the first coding sequence, and the second coding sequence are arranged in order from a 5' side to a 3' side in the nucleic acid of (b).

7. The peptide nucleic acid complex according to claim 2, wherein the third coding sequence is a sequence encoding the transpeptidase N-terminal substrate motif, and
the third coding sequence, the second coding sequence, and the first coding sequence are arranged in order from a 5' side to a 3' side in the nucleic acid of (b).

8. The peptide nucleic acid complex according to claim 2, wherein the nucleic acid of (b) further contains a fourth coding sequence encoding a protease recognition motif.

9. A solid phase carrier on which the peptide-nucleic acid complex according to claim 1 has been immobilized.

10. A peptide array comprising a reaction chamber containing the solid phase carrier according to claim 9.

11. The peptide array according to claim 10, wherein each reaction chamber contains one kind of the peptide-nucleic acid complex.

* * * * *

SEQUENCE LISTING

```
<160> NUMBER OF SEQ ID NOS: 50

<210> SEQ ID NO 1
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Leu Pro Xaa Thr Gly
1               5

<210> SEQ ID NO 2
<211> LENGTH: 5
```

```
<212> TYPE: PRT
<213> ORGANISM: Artificial sequence
<220> FEATURE:
<223> OTHER INFORMATION: recognition motif of Sortase

<400> SEQUENCE: 2

Leu Pro Ala Thr Gly
1               5

<210> SEQ ID NO 3
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 3

Leu Pro Asn Thr Gly
1               5

<210> SEQ ID NO 4
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Leu Pro Xaa Ala Gly
1               5

<210> SEQ ID NO 5
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 5

Leu Pro Asn Ala Gly
1               5

<210> SEQ ID NO 6
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 6

Leu Pro Xaa Thr Ala
1               5

<210> SEQ ID NO 7
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 7
```

Leu Pro Asn Thr Ala
1               5

<210> SEQ ID NO 8
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 8

Leu Gly Xaa Thr Gly
1               5

<210> SEQ ID NO 9
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 9

Leu Gly Ala Thr Gly
1               5

<210> SEQ ID NO 10
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 10

Ile Pro Xaa Thr Gly
1               5

<210> SEQ ID NO 11
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 11

Ile Pro Asn Thr Gly
1               5

<210> SEQ ID NO 12
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 12

Ile Pro Glu Thr Gly
1               5

<210> SEQ ID NO 13

```
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Thr Leu Xaa Thr Cys
1               5

<210> SEQ ID NO 14
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 14

Leu Pro Glu Thr Gly
1               5

<210> SEQ ID NO 15
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Xaa Pro Xaa Thr Gly
1               5

<210> SEQ ID NO 16
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 16

Leu Ala Xaa Thr Gly
1               5

<210> SEQ ID NO 17
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 17
```

```
Leu Pro Xaa Ser Gly
1               5

<210> SEQ ID NO 18
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 18

Asn Pro Gln Thr Asn
1               5

<210> SEQ ID NO 19
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 19

Asn Pro Lys Thr Gly
1               5

<210> SEQ ID NO 20
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 20

Asn Ser Lys Thr Ala
1               5

<210> SEQ ID NO 21
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 21

Asn Pro Gln Thr Gly
1               5

<210> SEQ ID NO 22
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 22

Asn Ala Lys Thr Asn
1               5

<210> SEQ ID NO 23
<211> LENGTH: 5
<212> TYPE: PRT
<213> ORGANISM: Artificial sequence
<220> FEATURE:
<223> OTHER INFORMATION: recognition motif of Sortase

<400> SEQUENCE: 23
```

Asn Pro Gln Ser Ser
1               5

<210> SEQ ID NO 24
<211> LENGTH: 5
<212> TYPE: PRT
<213> ORGANISM: Artificial sequence
<220> FEATURE:
<223> OTHER INFORMATION: recognition motif of Sortase
<220> FEATURE:
<221> NAME/KEY: misc_feature
<222> LOCATION: (3)..(3)
<223> OTHER INFORMATION: Glu, Ala, Ser or His

<400> SEQUENCE: 24

Asn Ala Xaa Thr Gly
1               5

<210> SEQ ID NO 25
<211> LENGTH: 6
<212> TYPE: PRT
<213> ORGANISM: Artificial sequence
<220> FEATURE:
<223> OTHER INFORMATION: recognition motif of Sortase

<400> SEQUENCE: 25

Gln Val Pro Thr Gly Val
1               5

<210> SEQ ID NO 26
<211> LENGTH: 4
<212> TYPE: PRT
<213> ORGANISM: Artificial sequence
<220> FEATURE:
<223> OTHER INFORMATION: intermediate sequence in transpeptidation
      reaction
<220> FEATURE:
<221> NAME/KEY: misc_feature
<222> LOCATION: (3)..(3)
<223> OTHER INFORMATION: Xaa can be any naturally occurring amino acid

<400> SEQUENCE: 26

Leu Pro Xaa Thr
1

<210> SEQ ID NO 27
<211> LENGTH: 7
<212> TYPE: PRT
<213> ORGANISM: Artificial sequence
<220> FEATURE:
<223> OTHER INFORMATION: recognition motif of TEV protease

<400> SEQUENCE: 27

Glu Asn Leu Tyr Phe Gln Gly
1               5

<210> SEQ ID NO 28
<211> LENGTH: 4
<212> TYPE: PRT
<213> ORGANISM: Artificial sequence
<220> FEATURE:
<223> OTHER INFORMATION: recognition motif of Xa protease
<220> FEATURE:
<221> NAME/KEY: misc_feature
<222> LOCATION: (2)..(2)
<223> OTHER INFORMATION: Glu or Asp

<400> SEQUENCE: 28

Ile Xaa Gly Arg
1

<210> SEQ ID NO 29
<211> LENGTH: 20
<212> TYPE: DNA
<213> ORGANISM: Artificial sequence
<220> FEATURE:
<223> OTHER INFORMATION: primer for PCR

<400> SEQUENCE: 29
cgccaatccg gatatagttc                                                 20

<210> SEQ ID NO 30
<211> LENGTH: 447
<212> TYPE: DNA
<213> ORGANISM: Artificial sequence
<220> FEATURE:
<223> OTHER INFORMATION: modified sortase A derived from Staphylococcus
      aureus

<400> SEQUENCE: 30
atgcaagcta aacctcaaat tccgaaagac aagagcaagg ttgctgggta tatcgagatt      60
ccggatgcgg acatcaagga gccagtgtat ccaggaccag cgacttctga gcaactgaat     120 cgtgggggttt cgtttgccga agagaatgag agtctcgatg accagaacat ctccatagca    180
ggtcacacct tcatcgacag acccaactac cagttcacga acctcaaagc tgccaagaag     240
ggctcaatgg tgtacttcaa ggtcggcaat gagaccagga agtacaagat gacctccatt     300
cgcaacgtga acccacagc agtaggcgtc ttggatgagc aaaagggcaa ggacaagcag      360
cttacgctga tcacctgcga tgactacaac gagaaaaccg gagtctggga aactcggaag     420
atctttgtcg ccacagaagt gaagtga                                        447

<210> SEQ ID NO 31
<211> LENGTH: 4
<212> TYPE: PRT
<213> ORGANISM: Artificial sequence
<220> FEATURE:
<223> OTHER INFORMATION: a part of recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 31

Leu Pro Xaa Thr
1

<210> SEQ ID NO 32
<211> LENGTH: 4
<212> TYPE: PRT
<213> ORGANISM: Artificial sequence
<220> FEATURE:
<223> OTHER INFORMATION: a part of recognition motif of Sortase

<400> SEQUENCE: 32

Leu Pro Ala Thr
1

<210> SEQ ID NO 33
<211> LENGTH: 4
<212> TYPE: PRT
<213> ORGANISM: Artificial sequence
<220> FEATURE:
<223> OTHER INFORMATION: a part of recognition motif of Sortase

```
<400> SEQUENCE: 33

Leu Pro Asn Thr
1

<210> SEQ ID NO 34
<211> LENGTH: 4
<212> TYPE: PRT
<213> ORGANISM: Artificial sequence
<220> FEATURE:
<223> OTHER INFORMATION: a part of recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 34

Leu Pro Xaa Ala
1

<210> SEQ ID NO 35
<211> LENGTH: 4
<212> TYPE: PRT
<213> ORGANISM: Artificial sequence
<220> FEATURE:
<223> OTHER INFORMATION: a part of recognition motif of Sortase

<400> SEQUENCE: 35

Leu Pro Asn Ala
1

<210> SEQ ID NO 36
<211> LENGTH: 4
<212> TYPE: PRT
<213> ORGANISM: Artificial sequence
<220> FEATURE:
<223> OTHER INFORMATION: a part of recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 36

Leu Pro Xaa Thr
1

<210> SEQ ID NO 37
<211> LENGTH: 4
<212> TYPE: PRT
<213> ORGANISM: Artificial sequence
<220> FEATURE:
<223> OTHER INFORMATION: a part of recognition motif of Sortase

<400> SEQUENCE: 37

Leu Pro Asn Thr
1

<210> SEQ ID NO 38
<211> LENGTH: 4
<212> TYPE: PRT
<213> ORGANISM: Artificial sequence
<220> FEATURE:
<223> OTHER INFORMATION: a part of recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 38
```

```
Leu Gly Xaa Thr
1

<210> SEQ ID NO 39
<211> LENGTH: 4
<212> TYPE: PRT
<213> ORGANISM: Artificial sequence
<220> FEATURE:
<223> OTHER INFORMATION: a part of recognition motif of Sortase

<400> SEQUENCE: 39

Leu Gly Ala Thr
1

<210> SEQ ID NO 40
<211> LENGTH: 4
<212> TYPE: PRT
<213> ORGANISM: Artificial sequence
<220> FEATURE:
<223> OTHER INFORMATION: a part of recognition motif of Sortase
<220> FEATURE:
<221> NAME/KEY: misc_feature
<222> LOCATION: (3)..(3)
<223> OTHER INFORMATION: Xaa can be any naturally occurring amino acid

<400> SEQUENCE: 40

Ile Pro Xaa Thr
1

<210> SEQ ID NO 41
<211> LENGTH: 4
<212> TYPE: PRT
<213> ORGANISM: Artificial sequence
<220> FEATURE:
<223> OTHER INFORMATION: a part of recognition motif of Sortase

<400> SEQUENCE: 41

Ile Pro Asn Thr
1

<210> SEQ ID NO 42
<211> LENGTH: 4
<212> TYPE: PRT
<213> ORGANISM: Artificial sequence
<220> FEATURE:
<223> OTHER INFORMATION: a part of recognition motif of Sortase

<400> SEQUENCE: 42

Ile Pro Glu Thr
1

<210> SEQ ID NO 43
<211> LENGTH: 6
<212> TYPE: PRT
<213> ORGANISM: Artificial Sequence
<220> FEATURE:
<223> OTHER INFORMATION: pentaglycine
<220> FEATURE:
<221> NAME/KEY: MISC_FEATURE
<222> LOCATION: (6)..(6)
<223> OTHER INFORMATION: propargylglycine

<400> SEQUENCE: 43

Gly Gly Gly Gly Gly Xaa
1               5

<210> SEQ ID NO 44
<211> LENGTH: 1795
```

<212> TYPE: DNA
<213> ORGANISM: Artificial Sequence
<220> FEATURE:
<223> OTHER INFORMATION: template DNA containing PPK

<400> SEQUENCE: 44

```
cgccaatccg gatatagttc gtaaaacgac ggccagtgag ctagtgtaat acgactcact      60
atagggaat tgtgagcgga taacaattcc cctctagaaa taattttgtt taactttaag     120
aaggagatat accatggaac agaaactgat ttcggaagag gatttagcct tagatgaagc     180
tccagcagag gcgcgtccag gtagccgtgc agtggaactg gaaattgatg gccgttcgcg     240
tattttcgac attgacgatc cggatctgcc gaaatggatc gatgaagaag cctttcgcag     300
tgatgattat ccgtacaaga agaaactgga tcgtgaggaa tacgaggaaa cgttgaccaa     360
actccagatt gagctggtca agtccagtt tggatgcaa gcgactggga aacgcgtcat      420
ggcggtattt gagggccgtg atgctgctgg taaaggaggt gccatccatg cgactacagc     480
gaacatgaat cctcgtagcg cacgtgtggt tgcccttacc aagccgaccg aaacggaacg     540
gggccaatgg tacttccaac ggtatgttgc gacgtttccc acagccgggg agttcgtgct     600
gtttgaccgc agctggtata atcgcgctgg cgtagagccg gttatgggct tttgcacccc     660
tgaccagtat gaacagtttc tgaaagaagc cccgcgcttt gaagaaatga tcgcgaatga     720
aggcatccac cttttcaagt tctggattaa cattgggcgc gaaatgcagt taaaacggtt     780
ccatgatcgc cgtcatgatc cgctgaaaat ctggaaatta tcgccgatgg atattgcagc     840
attgtccaaa tgggatgact acaccggtaa acgcgatcgt atgctgaagg aaacgcacac     900
cgaacatggc ccatgggccg tgattcgcgg caacgacaaa cgccgctctc gcatcaacgt     960
gattcgccac atgctgacca aactggacta tgacggcaaa gatgaagcgg cgattggtga    1020
agttgacgag aaaatcctcg gttcaggacc cggttttctg cgcattgagg gcagaagtgg    1080
actgccggaa accggtggcc atggcggtgg gtccggtggg agcggaggct cgggtggcag    1140
tggcggctcc atgcaagcta aacctcaaat tccgaaagac aagagcaagg ttgctgggta    1200
tatcgagatt ccggatgcgg acatcaagga gccagtgtat ccaggaccag cgacttctga    1260
gcaactgaat cgtggggttt cgtttgccga agagaatgag agtctcgatg accagaacat    1320
ctccatagca ggtcacacct tcatcgacag acccaactac cagttcacga acctcaaagc    1380
tgccaagaag ggctcaatgg tgtacttcaa ggtcggcaat gagaccagga agtacaagat    1440
gacctccatt cgcaacgtga aacccacagc agtaggcgtc ttggatgagc aaaagggcaa    1500
ggacaagcag cttacgctga tcacctgcga tgactacaac gagaaaaccg gagtctggga    1560
aactcggaag atctttgtcg ccacagaagt gaagtgataa ccgctgagca ataactagca    1620
taaccccttg gggcctctaa acgggtcttg aggggttttt tgctgaaagg aggaactata    1680
tccggaaatt gtggatccgc tctagagtcg acctgcaggc atgcaagctt gcggccgcgt    1740
attctatagt gtcacctaaa tagcatggcg taatcatggt catagctgtt tcctg          1795
```

<210> SEQ ID NO 45
<211> LENGTH: 36
<212> TYPE: DNA
<213> ORGANISM: Homo sapiens

<400> SEQUENCE: 45

```
tgccgccata gccagatgac cgtgacgtcg cgtctg                                36
```

<210> SEQ ID NO 46

<211> LENGTH: 12
<212> TYPE: PRT
<213> ORGANISM: Homo sapiens

<400> SEQUENCE: 46

Cys Arg His Ser Gln Met Thr Val Thr Ser Arg Leu
1               5                   10

<210> SEQ ID NO 47
<211> LENGTH: 917
<212> TYPE: DNA
<213> ORGANISM: Artificial Sequence
<220> FEATURE:
<223> OTHER INFORMATION: template DNA containing CP05

<400> SEQUENCE: 47
gtaaaacgac ggccagtgag ctagtgtaat acgactcact atagggggaat tgtgagcgga      60
taacaattcc cctctagaaa taattttgtt aactttaag aaggagatat accatggaac      120
agaaactgat tcggaagag gatttaattg agggcagatg ccgccatagc agatgaccg       180
tgacgtcgcg tctgggtagt ggactgccgg aaaccggtgg ccatggcggt gggtccggtg     240
ggagcggagg ctcgggtggc agtggcggct ccatgcaagc taaacctcaa attccgaaag    300
acaagagcaa ggttgctggg tatatcgaga ttccggatgc ggacatcaag gagccagtgt    360
atccaggacc agcgacttct gagcaactga atcgtggggt ttcgttttgcc gaagagaatg   420
agagtctcga tgaccagaac atctccatag caggtcacac cttcatcgac agacccaact   480
accagttcac gaacctcaaa gctgccaaga agggctcaat ggtgtacttc aaggtcggca   540
atgagaccag gaagtacaag atgacctcca ttcgcaacgt gaaacccaca gcagtaggcg   600
tcttggatga gcaaaagggc aaggacaagc agcttacgct gatcacctgc gatgactaca   660
acgagaaaac cggagtctgg gaaactcgga agatctttgt cgccacagaa gtgaagtgat   720
aaccgctgag caataactag cataacccct tggggcctct aaacgggtct tgagggggttt  780
tttgctgaaa ggaggaacta tatccggaaa ttgtggatcc gctctagagt cgacctgcag  840
gcatgcaagc ttgcggccgc gtattctata gtgtcaccta aatagcatgg cgtaatcatg  900
gtcatagctg tttcctg                                                   917

<210> SEQ ID NO 48
<211> LENGTH: 51
<212> TYPE: DNA
<213> ORGANISM: Homo sapiens

<400> SEQUENCE: 48
acctatgccg atttcattgc aagcgggcgt acgggtcgcc ggaacgcgat c             51

<210> SEQ ID NO 49
<211> LENGTH: 17
<212> TYPE: PRT
<213> ORGANISM: Homo sapiens

<400> SEQUENCE: 49

Thr Tyr Ala Asp Phe Ile Ala Ser Gly Arg Thr Gly Arg Arg Asn Ala
1               5                   10                  15
Ile

<210> SEQ ID NO 50
<211> LENGTH: 956
<212> TYPE: DNA
<213> ORGANISM: Artificial Sequence
<220> FEATURE:
<223> OTHER INFORMATION: template DNA containing PKI

<400> SEQUENCE: 50

```
gtaaaacgac ggccagtgag ctagtgtaat acgactcact atagggggaat tgtgagcgga      60 taacaattcc cctctagaaa taattttgtt taactttaag aaggagatat accatggaac     120
agaaactgat ttcggaagag gatttaattg agggcagaac ctatgccgat ttcattgcaa     180
gcgggcgtac gggtcgccgg aacgcgatct tagaagtgct gtttcagggc ccgggtagtg     240
gactgccgga aaccggtggc catggcggtg ggtccggtgg gagcggaggc tcgggtggca     300
gtggcggctc catgcaagct aaacctcaaa ttccgaaaga caagagcaag gttgctgggt     360
atatcgagat tccggatgcg gacatcaagg agccagtgta tccaggacca gcgacttctg     420
agcaactgaa tcgtggggtt tcgtttgccg aagagaatga gagtctcgat gaccagaaca     480
tctccatagc aggtcacacc ttcatcgaca gacccaacta ccagttcacg aacctcaaag     540
ctgccaagaa gggctcaatg gtgtacttca aggtcggcaa tgagaccagg aagtacaaga     600
tgacctccat tcgcaacgtg aaacccacag cagtaggcgt cttggatgag caaaagggca     660
aggacaagca gcttacgctg atcacctgcg atgactacaa cgagaaaacc ggagtctggg     720
aaactcggaa gatctttgtc gccacagaag tgaagtgata accgctgagc aataactagc     780
ataacccctt ggggcctcta aacgggtctt gaggggtttt ttgctgaaag gaggaactat     840
atccggaaat tgtggatccg ctctagagtc gacctgcagg catgcaagct tgcggccgcg     900
tattctatag tgtcacctaa atagcatggc gtaatcatgg tcatagctgt ttcctg        956
```